US007807881B2

(12) United States Patent
Hammer et al.

(10) Patent No.: US 7,807,881 B2
(45) Date of Patent: *Oct. 5, 2010

(54) METHODS TO CONFER HERBICIDE RESISTANCE

(75) Inventors: Philip E. Hammer, Cary, NC (US);
Todd K. Hinson, Rougemont, NC (US);
Nicholas B. Duck, Apex, NC (US);
Michael G. Koziel, Raleigh, NC (US)

(73) Assignee: Athenix Corp., Research Triangle Park, NC (US)

( * ) Notice: Subject to any disclaimer, the term of this patent is extended or adjusted under 35 U.S.C. 154(b) by 769 days.

This patent is subject to a terminal disclaimer.

(21) Appl. No.: 11/588,811

(22) Filed: Oct. 27, 2006

(65) Prior Publication Data
US 2007/0107078 A1 May 10, 2007

Related U.S. Application Data

(63) Continuation-in-part of application No. 10/797,270, filed on Mar. 10, 2004, now abandoned.

(60) Provisional application No. 60/453,148, filed on Mar. 10, 2003.

(51) Int. Cl.
C12N 15/82 (2006.01)
A01H 5/00 (2006.01)
A01H 5/10 (2006.01)

(52) U.S. Cl. .................. 800/300; 435/419; 800/288; 800/298

(58) Field of Classification Search .................. None
See application file for complete search history.

(56) References Cited

U.S. PATENT DOCUMENTS

| 4,535,060 A | 8/1985 | Comai |
| 4,769,061 A | 9/1988 | Comai |
| 5,094,945 A | 3/1992 | Comai |
| 5,188,642 A | 2/1993 | Shah et al. |
| 5,378,824 A | 1/1995 | Bedbrook et al. |
| 5,463,175 A | 10/1995 | Barry et al. |
| 5,928,937 A * | 7/1999 | Kakefuda et al. ........ 435/320.1 |
| 6,448,476 B1 | 9/2002 | Barry |
| 7,504,561 B2 * | 3/2009 | Hammer et al. ............ 800/300 |
| 7,538,262 B2 * | 5/2009 | Hammer et al. ............ 800/300 |

FOREIGN PATENT DOCUMENTS

| WO | WO 99/43833 A1 | 9/1999 |
| WO | WO 00/32789 A1 | 6/2000 |
| WO | WO 00/77185 A1 | 12/2000 |
| WO | WO 02/36782 A2 | 5/2002 |
| WO | WO 02/36787 A2 | 5/2002 |

OTHER PUBLICATIONS

Arjunan, P., et al., "Crystal Structure of the Thiamin Diphosphate-dependent Enzyme Pyruvate Decarboxylase from the Yeast *Saccharomyces cerevisiae* at 2.3 A Resolution," *J. Mol Biol.*, 1996, pp. 590-660, vol. 256.
Bar-Ilan, A., et al., "Binding and Activation of Thiamin Diphosphate in Acetohydroxyacid Synthase," *Biochemistry* 2001, pp. 11946-11954, vol. 40.
Hawkins, C.F., et al., "A Common Structural Motif in Thiamin Pyrophosphate-binding Enzymes," *FEBS Letters*, Sep. 1989, pp. 77-82, vol. 255, No. 1.
Hohmann, S., & Meacock, P.A., "Thiamin Metabolism and Thiamin Diphosphate-dependent Enzymes in the Yeast *Saccharomyces cerevisiae*: Genetic Regulation," *Biochemica et Biophysica Acta*, 1998, pp. 201-219, vol. 1385.
Jordan, F., "Interplay of Organic and Biological Chemistry in Understanding Coenzyme Mechanisms: Example of Thiamin Diphosphate-dependent Decarboxylations of 2-oxo Acids," *FEBS Letters*, 1999, pp. 298-301, vol. 457.
Kishore, G.M., and Jacob, G.S., "Degradation of Glyphosate by *Pseudomonas* sp. PG2982 via a Sarcosine Intermediate," *J. Biol. Chem.*, Sep. 5, 1987, pp. 12164-12168, vol. 262, No. 25.
Ohta, H. and Sugai, T., "Enzyme-Mediated Decarboxylation Reactions in Organic Synthesis," *Stereoselective Biocatalysis* 2000, pp. 487-526, R. N. Patel, Ed., Marcel Deckker, Inc., Publisher.
Pohl, M., "Protein Design on Pyruvate Decarboxylase (PDC) by Site-Directed Mutagenesis," *Advances in Biochemical Engineering/Biotechnology*, 1997, pp. 15-43, vol. 58, Springer-Verlag, Berlin Heidelberg.
Saari, L.L., et al., "Resistance to Acetolactate Synthase Inhibiting Herbicides," *Herbicide Resistance in Plants*, 1994, pp. 83-139, CRC Press, Inc.
Shiao, T-L., et al., "Overexpression of Alcohol Dehydrogenase or Pyruvate Decarboxylast Improves Growth of Hairy Roots at Reduced Oxygen Concentrations," *Biotechnology and Bioengineering*, Feb. 15, 2002, pp. 455-461, vol. 77, No. 4.
Shinabarger, D.L. and Braymer, H.D., "Glyphosate Catabolism by *Pseudomonas* sp. Strain PG2982," *J. Bacteriol.*, Nov. 1986, pp. 702-707, vol. 168, No. 2.
Stock, M., et al., "Degradation of Glyphosate in Excised Leaves of Tobacco and Sugar Beet," *J. Plant Physiol.*, 1991, pp. 171-174, vol. 139.
Tadege, M., et al., "Anoxia Tolerance in Tobacco Roots: Effect of Overexpression of Pyruvate Decarboxylase," *The Plant Journal*, 1998, pp. 327-335, vol. 14, No. 3.
Wackett, L.P., et al., "Bacterial Carbon-Phosphorus Lyase: Products, Rates, and Regulation of Phosphonic and Phosphinic Acid Metabolism," *J. Bacteriol.*, Feb. 1987, pp. 710-717, vol. 169, No. 2.

(Continued)

*Primary Examiner*—David H Kruse
(74) *Attorney, Agent, or Firm*—Destiny M. Davenport

(57) ABSTRACT

Compositions and methods for conferring herbicide resistance to plant cells and bacterial cells are provided. The methods comprise transforming the cells with nucleotide sequences encoding herbicide resistance genes. In particular, herbicide resistance is conferred by expression of proteins with homology to decarboxylase enzymes. Compositions comprise transformed plants, plant tissues, and seeds, as well as transformed bacterial cells.

8 Claims, 5 Drawing Sheets

OTHER PUBLICATIONS

Ward, O.P. and Singh, A., "Enzymatic Asymmetric Synthesis by Decarboxylases," *Current Opinion in Biotechnology*, 2000, pp. 520-526, vol. 11.

NCBI Database Report for Accession No. AF098293, Direct Submission on Oct. 13, 1998.

* cited by examiner

```
                    *         20         *         40         *         60         *         80
GDC-1(full  : ---------------------------------------------------------------------------MASIN :   5
GDC-2       : -MLRSRQASKALRALGQARHFTSTTQPAAVQAPRKVASGQRNQATAATATSAAPNVRATPSPAFNAEEQQQQKHSHVQPLVNPQK :  84
S_cerevisa  : -------------------------------------------------------------------------------------- :   -
SAlmonella  : -------------------------------------------------------------------------------------- :   -
Z_mobilis_  : -------------------------------------------------------------------------------------- :   -
S_cer-_ILV  : MIRQSTLKNFAIKRCFQHIAYRNTPAMRSVALAQRFYS---SSSRYYSASPLPASKRPEPAPSFNVDPLEQPAEPSKLAKKLRAE :  82
Pyr_oryzae  : -MLR-TVGRKALRGSSKGCSRTISTLKPATATIAKPGS--RTLSTPATATATAP--RTKPSASFNARRDP-------QPLVNPRS :  72

*        100         *        120         *        140         *        160         *
GDC-1(full  : IRVQNLEQPMDYAEYLFRELHEIGTRSHHLGDYNVLALDYLPSCG-LRSGSVEDLNAYAADGYARVKQ-MGASITTTSLPGE    :  88
GDC-2       : SDMDESFIGKGGQIFHEMLRQGMKHYYGGAILPYFDAIYNSKHFDLPRHEQGGHMASGYARLSSKPGVLVTSSPGA          : 169
S_cerevisa  : ------MSEILGKYLFERLKQVNVNTLLGDFMDSLLDKIYEVEGMRLAGNADELNPIAADGYARIK-MSCLTTTPGE          :  78
SAlmonella  : -----MQNPYVADYILDRLAGCGIGHYYGGAILQFIDHVIDHPTLRSGCANDLNAYAADGYARM-AGALTTTPGE            :  79
Z_mobilis_  : -------MSYVGTYLAERLVQIGLKHHAVAGDYMLVLLDNLLNKNMEQYCCMDLNCQPSASGYARAK--AAAAVTYSVGA      :  77
S_cer-_ILV  : PDMDTSFVGLGGQIFNEMLSRQNVDTYYGGAILPYFDAIHNSDKFNLPKHEQGGHMASGYARKSKPGVLVTSSPGA          : 167
Pyr_oryzae  : GEADESFIGKGGEIFHEMALRQNVKHYYGGAILPYFDAIYMSKHIDLPKHEQGGHMASGYARASKPGVLVTSSPGA          : 157
                              t       6       6     fg pG    *    D 6             E   a  A GYAR  g      6 T g G
```

FIG. 1A

```
              180         *         200         *         220         *         240         *
GDC-1(full : LSANGVAGAFSEHVVVHIVGCRSTASQ-RNGMLLHHTLGNGDFNIFAMMSAQIECEVAKETSPAEIATQIDHALRVCFIRSRP : 172
GDC-2      : TNVSTPMQDALSDGTSLVVFCEQVPTSAIGSDAFQEADVVGISRACTKMMMVKNVAELPRRIREAFEIATSGRPGPVIVDLPKD : 254
S_cerevisa : LSANGIAGSYAEHVCVLHVGVSISSQ-AKQLLLHHTLGNGDFTVFHRMSANISETTAMKTLICTAPAEIDNCIRTTYVTQRP : 162
SAlmonella : LSANGIAGSYAEYVVVLHIVGAPCSAAQ-QRGELLHHTLGDGDFRHFYRMSQAIEAAS-AILEQNACFEIDRVLGEMLAARR : 162
Z_mobilis_ : HSAFDALGKATAENLSVIELSGAGNNNDH-AAGHVLHHALGKIDVHYQLEMAKNIIAAAEASYTPEEAPAKIDHVIKTALAKKKK : 161
S_cer-_ILV : TNVSTPMADAFADGISMVVFTEQVPTSAIGTEAFQEADVVGISRSCTKMMVKSVEELPLFIEEAFEITSGRPGPVIVDLPKD : 252
Pyr_oryzae : TNVSTPMADALADGTSLVVFSEQVVTSDIGSDAFQEADVIGISRSCTKMMVKSADELPRRIEEAFEIATSGRPGPVIVDPARD : 242
              6          p66 G       *          6G       6                                  4

260         *         280         *         300         *         320         *         340
GDC-1(full : XIMLPTRMVQAKVEGARLKEPIDLSEPPNDPEKEAYVSDVVLKYLRAAMNP.SVDACAIHR-VLDEVHDLIEKTNLPVFVTP : 256
GDC-2      : QTAGILRRAIPTETALPALPSAASRAAMESSRKHLEHTIKRVADLVNKAQPFSYAGQGIIQSEGGPELLKELAMKASIPVTTTL : 339
S_cerevisa : VLGIPANLVDLNVPAKLEQTPIDMSLKPNDAESEKEVIDTLVLAKDAKNPSSKDACCSEHD-VKAETKKEIDLTQFRAFVIP : 246
SAlmonella : GXIMLPADVAKKTAIPPTQALALPVHEAQSG--VETAFRYHARQCLMNSERIASEADFLAGRFG-LRPLLQRWMAETPIAHAILL : 244
Z_mobilis_ : VLEIACNLASMPCAASGPASALFMDEASDEASLNAAVDETIKFIAN--RDKSAMLVGSKLAAGAEEAAVKFIDALGGAVATMA : 244
S_cer-_ILV : QTAALRNPIPTKTTLESNA--LNQLTSRAQDEFVMQSINKAADLIMLAAKFSYVGAGIENHADGPRLLKELSDAQIPVTTTL : 335
Pyr_oryzae : QTASVLRRAIPTETSIESIS-AAARAVQEAGRKQLEHSIKRVADLVNIAMKFSYAGQGVILSEGGVELLKALAMKASIPVTTTL : 326
              v   6          P            6                                4    v
```

FIG. 1B

```
              *         360         *         380         *         400         *         420
GDC-1(full : MKKAVUDEHPTYGNYAGDGHPPQVKDMWSSDIIDIALKSDFMIAGESYRTSQLNTIDLHSDHCIVKYSTV--PGVQMCG : 339
GDC-2      : QQLSGHDLDEKSLHMLGMHQAY--ANMAVEDIIDLARHDDRVTLNVAKFAPGANAAAEKRGGIVHEEVM--PKNINAV : 420
S_cerevisa : MKKSISDHPPYGNYVGTLKP-EVKEAVSEDIILSVALLSDFMTGSEYSYKTKNIVEFHSDHMKIRNATF--PGVQMCF : 328
SAlmonella : MKKLIDEHPNEYGTYSAGASK-EVRQAIDEDRVICVCTKEVDTEIAGFTQQLPAERTLEIQPYASRIGETWFNLDMAQAVS : 328
Z_mobilis_ : AAKSFFPENPHYIGTSWGEVYP-GVEKTMKEEDAVIALAPVTMDYSITGMIDIPDPKKLVLAEPRSVVVRRIRE--PSVHLTD : 326
S_cer_ILV  : QQLSHIDEDPRSLDMLGMHQCAT--ANLAVNDIIIAVARHDDRVGNISKFAPEARAAAEGRGGIVHEEVS--PKNIMAV : 416
Pyr_oryzae : HQLGAFDELDEKALHMLGMHQAY--ANMSWEEDIIDALGREDDRVGSIPKFAPAAKLAAAEGRGGIVHEEIM--PKNINAV : 407
              g g       2                 s      6   aD 66 6g   D   T                6         P

*         440         *         460         *         480         *         500         *
GDC-1(full : VLRQVIKGLDASEINAQPAPVVEN---------------------EVAKMRD-MSPVITAAFFWPRVGEFLKKNDIVITEKGTA : 401
GDC-2      : YQATEAVKEGNVGSNLKLLIPEVQAKTMDDRKEWFGKINEWKKKWPLSHYERAERHGLIKPETLEEELSKLTADRKRKTYIARGVG : 505
S_cerevisa : VLQKELTNIADAAKGYKPVAVPAR---------------------TPANAAVPASTPLREWMWNQLGNFLQEGDVVIAEKGTS : 391
SAlmonella : TLRELCIECAFAPPPTRSAGQPVR---------------------IDKGEITRESFWQTIQQYLKPGILILVDQGTA : 384
Z_mobilis_ : YLTREIAQKVSKKTGSLDFFKSINAG-------------------ELKKAAPADPSAPLVNAEIARQVEALITPNTTVVIAEFGDS : 391
S_cer_ILV  : VQTQIAVEGDATINLGKMUSKIFP--VKERSEWFAQIMKWKEEYPYAYMEETPGS-KIKPETVIKKLSKVANDTGRHVITAGVG : 498
Pyr_oryzae : YQATEAIEGDVASNLKLLLPKIEQRSMTDRKEWFDQIKEWKEKWPLSHYERAERSGLIKPETLEEELSNLTADRKDKTYITAGVG : 492
                                                                 q                          tG
```

FIG. 1C

```
                520         *         540         *         560         *         580         *
GDC-1(full : NFGIWDTKFFSGVTALSQSLWGSTGWSWGACQGAVIAAADDNSDRRTSLFYGDGSFQLTAGELSMIRLKLKPIIFVICNDG--- : 483
GDC-2      : QHQMWTAQHFRWRHPRSMSTSGGLG-IWGFGSPASIGKVAQSRALVFDIDGDASFGWTRTELASAAQFNIGVKVIVLSNEEQGM : 589
S_cerevisa : AFGINQTTFFNNTYGISSSLWGSIGFTTDATSGAFASEEIDSKRRVSLFYGDGSLGLTSREISSMIRWGLKPYLFVLSNDG--- : 473
SAlmonella : AFGAAALSLSDGAEVVLQPLWGSTG---YS-SPASFGSQTACSRRRVSLISGDGAAQLTISMGSMRDGQAPVISLLINDG--- : 462
Z_mobilis_ : WFNAQRMKLSNGARVEYSSQWGHIG---WS-SPASFGYAWGASFRRNSLNWGDGSFTAGEVAQMVRLKSPWIIFLISNYG--- : 469
S_cer-_ILV : QHQMWAAQHWTWRNPHIFSTSGGLG-IWGYGSPAFIGSQVAKSESLVSDIDGDASFNMISTELSSASQAGTPVKIIISNEEQGM : 582
Pyr_oryzae : QHQMWTAQHFRWRHPRSMSTSGGLG-IWGYCSPASIGKWARSRALVSDIDGDASFNMISTELSSAAQFNIGVKVIVLSNEEQGM : 576
                            G  6G         Aa   a    p    i  GD s   6T E6         6   66nN 600         *         620         *         640         *         660         *         680
GDC-1(full : -FIESRFISGMEAEWNDIAWWDSKALVDVFGG-----SKTAKKFAVKTKDELDSSLIDPTFNAAECLQFWELYMSKEFAPRALIM : 562
GDC-2      : VTQWWQNLFYEDRYAHTHQVWPDSMKLAESSRVQ----GRRCVDPEDVVDSLKWLSIEGPALLEVVTDKKVPSMSMVPAGSALHS : 670
S_cerevisa : -YTLEKLIRGPRAQWNESQGSDHLSSLPTFG------AKDYETHRVATTGSWDKSTQSKSFNDNSKSRMISSVMSFSAPQMLVS : 551
SAlmonella : -YIWSRAIHGAAQRYWDIASWKSTQIPPAIN-A----AQQAECWRVTQAIQLAESLERLAR--PQRSSFISVSLSKADLPELLRT : 539
Z_mobilis_ : -YTIEFVMEHDG--PSWWIKMWWSAGLMEVFNGNGGYDSGAAKGLKAKTGGSLAEAIKVALAN-TDGPTLIECPIGREDCTEELVK : 550
S_cer-_ILV : VTQWWQSLFYEHRYSHTHQLWPDSIKLAEAMGLK----GLRVKKQEELDAKLKEFSSKGPVLLEVEYDKKVPSISVAGGSGDES : 663
Pyr_oryzae : VTQWWQNLFYEDRYSHTHQRWPDSMKLADASDVQ----HSRVSKPDDVGDALTWLSIEGPALLEVMTDKKVPSISMVPGGNGDHS : 657
              2                1   6                                                          6p         L

*         700
GDC-1(full : TAEASSRNSAKTE-------------- : 575
GDC-2      : SLVFDGEKSKSRRELMRERTSGLHG- : 695
S_cerevisa : QAKLTSAATSASQ-------------- : 563
SAlmonella : VTRALEARSGG---------------- : 550
Z_mobilis_ : SGKRVSAASSSKPVNKLL--------- : 568
S_cer-_ILV : SINFDPEVERQQTELRHKRTGGKH-- : 687
Pyr_oryzae : SITFDSSKSKQRRELMRARTNGLHG- : 682
```

FIG. 1D

A.
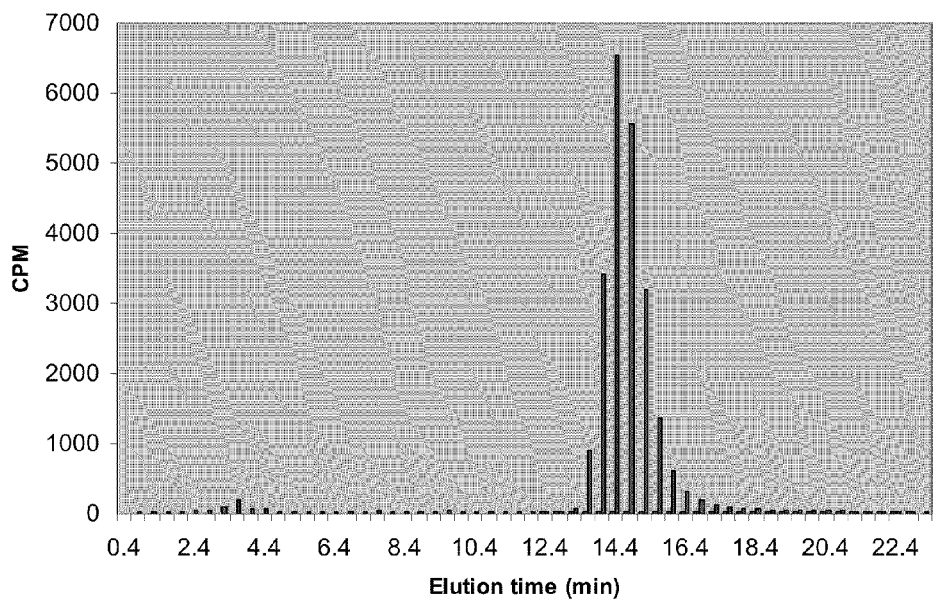
B.
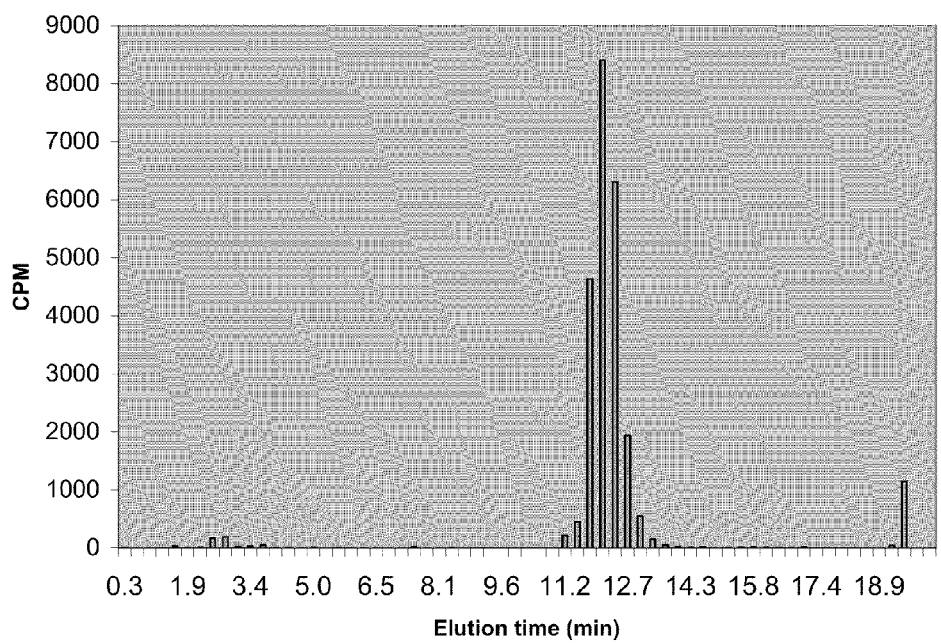
FIG. 2

SEQUENCE LISTING

```
<160> NUMBER OF SEQ ID NOS: 24

<210> SEQ ID NO 1
<211> LENGTH: 2210
<212> TYPE: DNA
<213> ORGANISM: Unknown
<220> FEATURE:
<221> NAME/KEY: CDS
<222> LOCATION: (224)...(1951)
<223> OTHER INFORMATION: Fungal isolate from soil sample

<400> SEQUENCE: 1
acgcggggtg cccacggaca acaattccct taggattatc tcctgtattg aatacactct      60
actttgcaac tttacctatt attcgacttt cttttagagg agcagcattg tcatcattac     120
ctgcccctcc atctgatacc taccttacat tgtcgccaac acacctataa gccataatat     180
accgactcaa agcaaaccac gcccattgtt tgattgttta atc atg gcc agc atc       235
                                                  Met Ala Ser Ile
                                                    1 aac atc agg gtg cag aat ctc gag caa ccc atg gac gtt gcc gag tat       283
Asn Ile Arg Val Gln Asn Leu Glu Gln Pro Met Asp Val Ala Glu Tyr
  5                  10                  15                  20 ctt ttt cgg cgt ctc cac gaa atc ggc att cgc tcc atc cac ggt ctt       331
Leu Phe Arg Arg Leu His Glu Ile Gly Ile Arg Ser Ile His Gly Leu
                 25                  30                  35 cca ggc gat tac aac ctt ctt gcc ctc gac tat ttg cca tca tgt ggc       379
Pro Gly Asp Tyr Asn Leu Leu Ala Leu Asp Tyr Leu Pro Ser Cys Gly
             40                  45                  50 ctg aga tgg gtt ggc agc gtc aac gaa ctc aat gct gct tat gct gct       427
Leu Arg Trp Val Gly Ser Val Asn Glu Leu Asn Ala Ala Tyr Ala Ala
         55                  60                  65 gat ggc tat gcc cgc gtc aag cag atg gga gct ctc atc acc act ttt       475
Asp Gly Tyr Ala Arg Val Lys Gln Met Gly Ala Leu Ile Thr Thr Phe
     70                  75                  80 gga gtg gga gag ctc tca gcc atc aat ggc gtt gcc ggt gcc ttt tcg       523
Gly Val Gly Glu Leu Ser Ala Ile Asn Gly Val Ala Gly Ala Phe Ser
 85                  90                  95                 100 gaa cac gtc cca gtc gtt cac att gtt ggc tgc cct tcc act gtc tcg       571
Glu His Val Pro Val Val His Ile Val Gly Cys Pro Ser Thr Val Ser
                105                 110                 115 cag cga aac ggc atg ctc ctc cac cac acg ctt gga aac ggc gac ttc       619
Gln Arg Asn Gly Met Leu Leu His His Thr Leu Gly Asn Gly Asp Phe
            120                 125                 130 aac atc ttt gcc aac atg agc gct caa atc tct tgc gaa gtg gcc aag       667
Asn Ile Phe Ala Asn Met Ser Ala Gln Ile Ser Cys Glu Val Ala Lys
        135                 140                 145 ctc acc aac cct gcc gaa att gcg acc cag atc gac cat gcc ctc cgc       715
Leu Thr Asn Pro Ala Glu Ile Ala Thr Gln Ile Asp His Ala Leu Arg
```

```
                150                 155                 160
gtt tgc ttc att cgt tct cgg ccc gtc tac atc atg ctt ccc acc gat        763
Val Cys Phe Ile Arg Ser Arg Pro Val Tyr Ile Met Leu Pro Thr Asp
165                 170                 175                 180 atg gtc cag gcc aaa gta gaa ggt gcc aga ctc aag gaa cca att gac        811
Met Val Gln Ala Lys Val Glu Gly Ala Arg Leu Lys Glu Pro Ile Asp
                185                 190                 195 ttg tcg gag cct cca aat gat ccc gag aaa gaa gca tac gtc gtt gac        859
Leu Ser Glu Pro Pro Asn Asp Pro Glu Lys Glu Ala Tyr Val Val Asp
        200                 205                 210 gtt gtc ctc aag tay ctc cgt gct gca aag aac ccc gtc atc ctt gtc        907
Val Val Leu Lys Tyr Leu Arg Ala Ala Lys Asn Pro Val Ile Leu Val
            215                 220                 225 gat gct tgt gct atc cgt cat cgt gtt ctt gat gag gtt cat gat ctc        955
Asp Ala Cys Ala Ile Arg His Arg Val Leu Asp Glu Val His Asp Leu
230                 235                 240 atc gaa aag aca aac ctc cct gtc ttt gtc act cct atg ggc aaa ggt       1003
Ile Glu Lys Thr Asn Leu Pro Val Phe Val Thr Pro Met Gly Lys Gly
245                 250                 255                 260 gct gtt aac gaa gaa cac ccg aca tat ggt ggt gtc tat gcc ggt gac       1051
Ala Val Asn Glu Glu His Pro Thr Tyr Gly Gly Val Tyr Ala Gly Asp
                265                 270                 275 ggc tca cat ccg cct caa gtt aag gac atg gtt gag tct tct gat ttg       1099
Gly Ser His Pro Pro Gln Val Lys Asp Met Val Glu Ser Ser Asp Leu
        280                 285                 290 ata ttg aca atc ggt gct ctc aag agc gac ttc aac act gct ggc ttc       1147
Ile Leu Thr Ile Gly Ala Leu Lys Ser Asp Phe Asn Thr Ala Gly Phe
            295                 300                 305 tct tac cgt acc tca cag ctg aac acg att gat cta cac agc gac cac       1195
Ser Tyr Arg Thr Ser Gln Leu Asn Thr Ile Asp Leu His Ser Asp His
310                 315                 320 tgc att gtc aaa tac tcg aca tat cca ggt gtc cag atg agg ggt gtg       1243
Cys Ile Val Lys Tyr Ser Thr Tyr Pro Gly Val Gln Met Arg Gly Val
325                 330                 335                 340 ctg cga caa gtg att aag cag ctc gat gca tct gag atc aac gct cag       1291
Leu Arg Gln Val Ile Lys Gln Leu Asp Ala Ser Glu Ile Asn Ala Gln
                345                 350                 355 cca gcg cca gtc gtc gag aat gaa gtt gcc aaa aac cga gat aac tca       1339
Pro Ala Pro Val Val Glu Asn Glu Val Ala Lys Asn Arg Asp Asn Ser
        360                 365                 370 ccc gtc att aca caa gct ttc ttc tgg ccg cgc gtg gga gag ttc ctg       1387
Pro Val Ile Thr Gln Ala Phe Phe Trp Pro Arg Val Gly Glu Phe Leu
            375                 380                 385 aag aag aac gac atc gtc att acc gag act gga aca gcc aac ttt ggc       1435
Lys Lys Asn Asp Ile Val Ile Thr Glu Thr Gly Thr Ala Asn Phe Gly
390                 395                 400 atc tgg gat act aag ttt ccc tct ggc gtt act gcg ctt tct cag gtc       1483
Ile Trp Asp Thr Lys Phe Pro Ser Gly Val Thr Ala Leu Ser Gln Val
405                 410                 415                 420 ctt tgg gga agc att ggt tgg tcc gtt ggt gcc tgc caa gga gcc gtt       1531
Leu Trp Gly Ser Ile Gly Trp Ser Val Gly Ala Cys Gln Gly Ala Val
                425                 430                 435 ctt gca gcc gcc gat gac aac agc gat cgc aga act atc ctc ttt gtt       1579
Leu Ala Ala Ala Asp Asp Asn Ser Asp Arg Arg Thr Ile Leu Phe Val
        440                 445                 450 ggt gat ggc tca ttc cag ctc act gct caa gaa ttg agc aca atg att       1627
Gly Asp Gly Ser Phe Gln Leu Thr Ala Gln Glu Leu Ser Thr Met Ile
            455                 460                 465 cgt ctc aag ctg aag ccc atc atc ttt gtc atc tgc aac gat ggc ttt       1675
```

-continued

```
Arg Leu Lys Leu Lys Pro Ile Ile Phe Val Ile Cys Asn Asp Gly Phe
    470                 475                 480 acc att gaa cga ttc att cac ggc atg gaa gcc gag tac aac gac atc          1723
Thr Ile Glu Arg Phe Ile His Gly Met Glu Ala Glu Tyr Asn Asp Ile
485                 490                 495                 500 gca aat tgg gac ttc aag gct ctg gtt gac gtc ttt ggc ggc tct aag          1771
Ala Asn Trp Asp Phe Lys Ala Leu Val Asp Val Phe Gly Gly Ser Lys
                505                 510                 515 acg gcc aag aag ttc gcc gtc aag acc aag gac gag ctg gac agc ctt          1819
Thr Ala Lys Lys Phe Ala Val Lys Thr Lys Asp Glu Leu Asp Ser Leu
            520                 525                 530 ctc aca gac cct acc ttt aac gcc gca gaa tgc ctc cag ttt gtc gag          1867
Leu Thr Asp Pro Thr Phe Asn Ala Ala Glu Cys Leu Gln Phe Val Glu
        535                 540                 545 cta tat atg ccc aaa gaa gat gct cct cga gca ttg atc atg act gca          1915
Leu Tyr Met Pro Lys Glu Asp Ala Pro Arg Ala Leu Ile Met Thr Ala
    550                 555                 560 gaa gct agc gcg agg aac aat gcc aag aca gag taa agtggactgt                1961
Glu Ala Ser Ala Arg Asn Asn Ala Lys Thr Glu  *
565                 570                 575 catgaaggcc gatttaccac ctcataaatt gtaatagacc tgatacacat agatcaaggc         2021
aggtaccgat cattaatcaa gcaggtttgg atgggaagg attttgaaaa tgaggaaacg          2081
atgggatgat atttggaata actggccatt attttgagta cttataaaca aatttgaagt         2141 tcaattttt ttcaaaaaaa aaaaaaaaaa aaaaaaaaaa aaaaaaaaaa aaaaaaaaaa          2201
aaaaaaaaa                                                                  2210

<210> SEQ ID NO 2
<211> LENGTH: 1725
<212> TYPE: DNA
<213> ORGANISM: Unknown
<220> FEATURE:
<221> NAME/KEY: CDS
<222> LOCATION: (1)...(1725)
<223> OTHER INFORMATION: Fungal isolate from soil sample

<400> SEQUENCE: 2 atg gcc agc atc aac atc agg gtg cag aat ctc gag caa ccc atg gac            48
Met Ala Ser Ile Asn Ile Arg Val Gln Asn Leu Glu Gln Pro Met Asp
1               5                  10                  15 gtt gcc gag tat ctt ttt cgg cgt ctc cac gaa atc ggc att cgc tcc            96
Val Ala Glu Tyr Leu Phe Arg Arg Leu His Glu Ile Gly Ile Arg Ser
                20                  25                  30 atc cac ggt ctt cca ggc gat tac aac ctt ctt gcc ctc gac tat ttg           144
Ile His Gly Leu Pro Gly Asp Tyr Asn Leu Leu Ala Leu Asp Tyr Leu
            35                  40                  45 cca tca tgt ggc ctg aga tgg gtt ggc agc gtc aac gaa ctc aat gct           192
Pro Ser Cys Gly Leu Arg Trp Val Gly Ser Val Asn Glu Leu Asn Ala
        50                  55                  60 gct tat gct gct gat ggc tat gcc cgc gtc aag cag atg gga gct ctc           240
Ala Tyr Ala Ala Asp Gly Tyr Ala Arg Val Lys Gln Met Gly Ala Leu
65                  70                  75                  80 atc acc act ttt gga gtg gga gag ctc tca gcc atc aat ggc gtt gcc           288
Ile Thr Thr Phe Gly Val Gly Glu Leu Ser Ala Ile Asn Gly Val Ala
                85                  90                  95 ggt gcc ttt tcg gaa cac gtc cca gtc gtt cac att gtt ggc tgc cct           336
Gly Ala Phe Ser Glu His Val Pro Val Val His Ile Val Gly Cys Pro
                100                 105                 110 tcc act gtc tcg cag cga aac ggc atg ctc ctc cac cac acg ctt gga           384
Ser Thr Val Ser Gln Arg Asn Gly Met Leu Leu His His Thr Leu Gly
```

-continued

```
              115                 120                 125
aac ggc gac ttc aac atc ttt gcc aac atg agc gct caa atc tct tgc        432
Asn Gly Asp Phe Asn Ile Phe Ala Asn Met Ser Ala Gln Ile Ser Cys
        130                 135                 140 gaa gtg gcc aag ctc acc aac cct gcc gaa att gcg acc cag atc gac        480
Glu Val Ala Lys Leu Thr Asn Pro Ala Glu Ile Ala Thr Gln Ile Asp
145                 150                 155                 160 cat gcc ctc cgc gtt tgc ttc att cgt tct cgg ccc gtc tac atc atg        528
His Ala Leu Arg Val Cys Phe Ile Arg Ser Arg Pro Val Tyr Ile Met
                165                 170                 175 ctt ccc acc gat atg gtc cag gcc aaa gta gaa ggt gcc aga ctc aag        576
Leu Pro Thr Asp Met Val Gln Ala Lys Val Glu Gly Ala Arg Leu Lys
            180                 185                 190 gaa cca att gac ttg tcg gag cct cca aat gat ccc gag aaa gaa gca        624
Glu Pro Ile Asp Leu Ser Glu Pro Pro Asn Asp Pro Glu Lys Glu Ala
        195                 200                 205 tac gtc gtt gac gtt gtc ctc aag tay ctc cgt gct gca aag aac ccc        672
Tyr Val Val Asp Val Val Leu Lys Tyr Leu Arg Ala Ala Lys Asn Pro
    210                 215                 220 gtc atc ctt gtc gat gct tgt gct atc cgt cat cgt gtt ctt gat gag        720
Val Ile Leu Val Asp Ala Cys Ala Ile Arg His Arg Val Leu Asp Glu
225                 230                 235                 240 gtt cat gat ctc atc gaa aag aca aac ctc cct gtc ttt gtc act cct        768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc        816
Met Gly Lys Gly Ala Val Asn Glu Glu His Pro Thr Tyr Gly Gly Val
            260                 265                 270 tat gcc ggt gac ggc tca cat ccg cct caa gtt aag gac atg gtt gag        864
Tyr Ala Gly Asp Gly Ser His Pro Pro Gln Val Lys Asp Met Val Glu
        275                 280                 285 tct tct gat ttg ata ttg aca atc ggt gct ctc aag agc gac ttc aac        912
Ser Ser Asp Leu Ile Leu Thr Ile Gly Ala Leu Lys Ser Asp Phe Asn
    290                 295                 300 act gct ggc ttc tct tac cgt acc tca cag ctg aac acg att gat cta        960
Thr Ala Gly Phe Ser Tyr Arg Thr Ser Gln Leu Asn Thr Ile Asp Leu
305                 310                 315                 320 cac agc gac cac tgc att gtc aaa tac tcg aca tat cca ggt gtc cag       1008
His Ser Asp His Cys Ile Val Lys Tyr Ser Thr Tyr Pro Gly Val Gln
                325                 330                 335 atg agg ggt gtg ctg cga caa gtg att aag cag ctc gat gca tct gag       1056
Met Arg Gly Val Leu Arg Gln Val Ile Lys Gln Leu Asp Ala Ser Glu
            340                 345                 350 atc aac gct cag cca gcg cca gtc gtc gag aat gaa gtt gcc aaa aac       1104
Ile Asn Ala Gln Pro Ala Pro Val Val Glu Asn Glu Val Ala Lys Asn
        355                 360                 365 cga gat aac tca ccc gtc att aca caa gct ttc ttc tgg ccg cgc gtg       1152
Arg Asp Asn Ser Pro Val Ile Thr Gln Ala Phe Phe Trp Pro Arg Val
    370                 375                 380 gga gag ttc ctg aag aag aac gac atc gtc att acc gag act gga aca       1200
Gly Glu Phe Leu Lys Lys Asn Asp Ile Val Ile Thr Glu Thr Gly Thr
385                 390                 395                 400 gcc aac ttt ggc atc tgg gat act aag ttt ccc tct ggc gtt act gcg       1248
Ala Asn Phe Gly Ile Trp Asp Thr Lys Phe Pro Ser Gly Val Thr Ala
                405                 410                 415 ctt tct cag gtc ctt tgg gga agc att ggt tgg tcc gtt ggt gcc tgc       1296
Leu Ser Gln Val Leu Trp Gly Ser Ile Gly Trp Ser Val Gly Ala Cys
            420                 425                 430 caa gga gcc gtt ctt gca gcc gcc gat gac aac agc gat cgc aga act       1344
Gln Gly Ala Val Leu Ala Ala Ala Asp Asp Asn Ser Asp Arg Arg Thr
```

```
Gln Gly Ala Val Leu Ala Ala Ala Asp Asp Asn Ser Asp Arg Arg Thr
            435                 440                 445 atc ctc ttt gtt ggt gat ggc tca ttc cag ctc act gct caa gaa ttg      1392
Ile Leu Phe Val Gly Asp Gly Ser Phe Gln Leu Thr Ala Gln Glu Leu
            450                 455                 460 agc aca atg att cgt ctc aag ctg aag ccc atc atc ttt gtc atc tgc      1440
Ser Thr Met Ile Arg Leu Lys Leu Lys Pro Ile Ile Phe Val Ile Cys
465                 470                 475                 480 aac gat ggc ttt acc att gaa cga ttc att cac ggc atg gaa gcc gag      1488
Asn Asp Gly Phe Thr Ile Glu Arg Phe Ile His Gly Met Glu Ala Glu
            485                 490                 495 tac aac gac atc gca aat tgg gac ttc aag gct ctg gtt gac gtc ttt      1536
Tyr Asn Asp Ile Ala Asn Trp Asp Phe Lys Ala Leu Val Asp Val Phe
            500                 505                 510 ggc ggc tct aag acg gcc aag aag ttc gcc gtc aag acc aag gac gag      1584
Gly Gly Ser Lys Thr Ala Lys Lys Phe Ala Val Lys Thr Lys Asp Glu
            515                 520                 525 ctg gac agc ctt ctc aca gac cct acc ttt aac gcc gca gaa tgc ctc      1632
Leu Asp Ser Leu Leu Thr Asp Pro Thr Phe Asn Ala Ala Glu Cys Leu
            530                 535                 540 cag ttt gtc gag cta tat atg ccc aaa gaa gat gct cct cga gca ttg      1680
Gln Phe Val Glu Leu Tyr Met Pro Lys Glu Asp Ala Pro Arg Ala Leu
545                 550                 555                 560 atc atg act gca gaa gct agc gcg agg aac aat gcc aag aca gag          1725
Ile Met Thr Ala Glu Ala Ser Ala Arg Asn Asn Ala Lys Thr Glu
            565                 570                 575

<210> SEQ ID NO 3
<211> LENGTH: 575
<212> TYPE: PRT
<213> ORGANISM: Unknown
<220> FEATURE:
<223> OTHER INFORMATION: Fungal isolate from soil sample

<400> SEQUENCE: 3

Met Ala Ser Ile Asn Ile Arg Val Gln Asn Leu Glu Gln Pro Met Asp
 1               5                  10                  15

Val Ala Glu Tyr Leu Phe Arg Arg Leu His Glu Ile Gly Ile Arg Ser
                20                  25                  30

Ile His Gly Leu Pro Gly Asp Tyr Asn Leu Leu Ala Leu Asp Tyr Leu
            35                  40                  45

Pro Ser Cys Gly Leu Arg Trp Val Gly Ser Val Asn Glu Leu Asn Ala
        50                  55                  60

Ala Tyr Ala Ala Asp Gly Tyr Ala Arg Val Lys Gln Met Gly Ala Leu
65                  70                  75                  80

Ile Thr Thr Phe Gly Val Gly Glu Leu Ser Ala Ile Asn Gly Val Ala
                85                  90                  95

Gly Ala Phe Ser Glu His Val Pro Val Val His Ile Val Gly Cys Pro
            100                 105                 110

Ser Thr Val Ser Gln Arg Asn Gly Met Leu Leu His Thr Leu Gly
        115                 120                 125

Asn Gly Asp Phe Asn Ile Phe Ala Asn Met Ser Ala Gln Ile Ser Cys
    130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
                165                 170                 175

Leu Pro Thr Asp Met Val Gln Ala Lys Val Glu Gly Ala Arg Leu Lys
```

```
                180                  185                  190
Glu Pro Ile Asp Leu Ser Glu Pro Pro Asn Asp Pro Glu Lys Glu Ala
            195                  200                  205

Tyr Val Asp Val Val Leu Lys Tyr Leu Arg Ala Ala Lys Asn Pro
        210                  215                  220

Val Ile Leu Val Asp Ala Cys Ala Ile Arg His Arg Val Leu Asp Glu
225                  230                  235                  240

Val His Asp Leu Ile Glu Lys Thr Asn Leu Pro Val Phe Val Thr Pro
                    245                  250                  255

Met Gly Lys Gly Ala Val Asn Glu Glu His Pro Thr Tyr Gly Gly Val
                260                  265                  270

Tyr Ala Gly Asp Gly Ser His Pro Pro Gln Val Lys Asp Met Val Glu
            275                  280                  285

Ser Ser Asp Leu Ile Leu Thr Ile Gly Ala Leu Lys Ser Asp Phe Asn
290                  295                  300

Thr Ala Gly Phe Ser Tyr Arg Thr Ser Gln Leu Asn Thr Ile Asp Leu
305                  310                  315                  320

His Ser Asp His Cys Ile Val Lys Tyr Ser Thr Tyr Pro Gly Val Gln
                325                  330                  335

Met Arg Gly Val Leu Arg Gln Val Ile Lys Gln Leu Asp Ala Ser Glu
                340                  345                  350

Ile Asn Ala Gln Pro Ala Pro Val Val Glu Asn Glu Val Ala Lys Asn
            355                  360                  365

Arg Asp Asn Ser Pro Val Ile Thr Gln Ala Phe Phe Trp Pro Arg Val
370                  375                  380

Gly Glu Phe Leu Lys Lys Asn Asp Ile Val Ile Thr Glu Thr Gly Thr
385                  390                  395                  400

Ala Asn Phe Gly Ile Trp Asp Thr Lys Phe Pro Ser Gly Val Thr Ala
                    405                  410                  415

Leu Ser Gln Val Leu Trp Gly Ser Ile Gly Trp Ser Val Gly Ala Cys
                420                  425                  430

Gln Gly Ala Val Leu Ala Ala Asp Asp Asn Ser Asp Arg Arg Thr
            435                  440                  445

Ile Leu Phe Val Gly Asp Gly Ser Phe Gln Leu Thr Ala Gln Glu Leu
450                  455                  460

Ser Thr Met Ile Arg Leu Lys Leu Lys Pro Ile Ile Phe Val Ile Cys
465                  470                  475                  480

Asn Asp Gly Phe Thr Ile Glu Arg Phe Ile His Gly Met Glu Ala Glu
                485                  490                  495

Tyr Asn Asp Ile Ala Asn Trp Asp Phe Lys Ala Leu Val Asp Val Phe
            500                  505                  510

Gly Gly Ser Lys Thr Ala Lys Lys Phe Ala Val Lys Thr Lys Asp Glu
            515                  520                  525

Leu Asp Ser Leu Leu Thr Asp Pro Thr Phe Asn Ala Ala Glu Cys Leu
            530                  535                  540

Gln Phe Val Glu Leu Tyr Met Pro Lys Glu Asp Ala Pro Arg Ala Leu
545                  550                  555                  560

Ile Met Thr Ala Glu Ala Ser Ala Arg Asn Asn Ala Lys Thr Glu
                565                  570                  575

<210> SEQ ID NO 4
<211> LENGTH: 835
<212> TYPE: DNA
<213> ORGANISM: Unknown
```

<220> FEATURE:
<221> NAME/KEY: CDS
<222> LOCATION: (3)...(596)
<223> OTHER INFORMATION: Fungal isolate from soil sample

<400> SEQUENCE: 4

```
ct ttc ttc tgg ccg cgc gtg gga gag ttc ctg aag aag aac gac atc         47
   Phe Phe Trp Pro Arg Val Gly Glu Phe Leu Lys Lys Asn Asp Ile
   1               5                  10                  15 gtc att acc gag act gga aca gcc aac ttt ggc atc tgg gat act aag        95
Val Ile Thr Glu Thr Gly Thr Ala Asn Phe Gly Ile Trp Asp Thr Lys
             20                  25                  30 ttt ccc tct ggc gtt act gcg ctt tct cag gtc ctt tgg gga agc att       143
Phe Pro Ser Gly Val Thr Ala Leu Ser Gln Val Leu Trp Gly Ser Ile
         35                  40                  45 ggt tgg tcc gtt ggt gcc tgc caa gga gcc gtt ctt gca gcc gcc gat       191
Gly Trp Ser Val Gly Ala Cys Gln Gly Ala Val Leu Ala Ala Ala Asp
     50                  55                  60 gac aac agc gat cgc aga act atc ctc ttt gtt ggt gat ggc tca ttc       239
Asp Asn Ser Asp Arg Arg Thr Ile Leu Phe Val Gly Asp Gly Ser Phe
 65                  70                  75 cag ctc act gct caa gaa ttg agc aca atg att cgt ctc aag ctg aag       287
Gln Leu Thr Ala Gln Glu Leu Ser Thr Met Ile Arg Leu Lys Leu Lys
 80                  85                  90                  95 ccc atc atc ttt gtc atc tgc aac gat ggc ttt acc att gaa cga ttc       335
Pro Ile Ile Phe Val Ile Cys Asn Asp Gly Phe Thr Ile Glu Arg Phe
             100                 105                 110 att cac ggc atg gaa gcc gag tac aac gac atc gca aat tgg gac ttc       383
Ile His Gly Met Glu Ala Glu Tyr Asn Asp Ile Ala Asn Trp Asp Phe
         115                 120                 125 aag gct ctg gtt gac gtc ttt ggc ggc tct aag acg gcc aag aag ttc       431
Lys Ala Leu Val Asp Val Phe Gly Gly Ser Lys Thr Ala Lys Lys Phe
     130                 135                 140 gcc gtc aag acc aag gac gag ctg gac agc ctt ctc aca gac cct acc       479
Ala Val Lys Thr Lys Asp Glu Leu Asp Ser Leu Leu Thr Asp Pro Thr
 145                 150                 155 ttt aac gcc gca gaa tgc ctc cag ttt gtc gag cta tat atg ccc aaa       527
Phe Asn Ala Ala Glu Cys Leu Gln Phe Val Glu Leu Tyr Met Pro Lys
160                 165                 170                 175 gaa gat gct cct cga gca ttg atc atg act gca gaa gct agc gcg agg       575
Glu Asp Ala Pro Arg Ala Leu Ile Met Thr Ala Glu Ala Ser Ala Arg
             180                 185                 190 aac aat gcc aag aca gag taa agtggactgt catgaaggcc gatttaccac         626
Asn Asn Ala Lys Thr Glu *
             195 ctcataaatt gtaatagacc tgatacacat agatcaaggc aggtaccgat cattaatcaa    686 gcaggtttgg atggggaagg attttgaaaa tgaggaaacg atgggatgat atttggaata    746 actggccatt attttgagta cttataaaca aatttgaagt tcaattttttt ttcaaaaaaa    806 aaaaaaaaaa aaaaaaaaaa aaaaaaaaa                                       835
```

<210> SEQ ID NO 5
<211> LENGTH: 591
<212> TYPE: DNA
<213> ORGANISM: Unknown
<220> FEATURE:
<221> NAME/KEY: CDS
<222> LOCATION: (1)...(591)
<223> OTHER INFORMATION: Fungal isolate from soil sample

<400> SEQUENCE: 5

| | | |
|---|---|---|
| ttc ttc tgg ccg cgc gtg gga gag ttc ctg aag aag aac gac atc gtc<br>Phe Phe Trp Pro Arg Val Gly Glu Phe Leu Lys Lys Asn Asp Ile Val<br>1               5                   10                  15 | | 48 |
| att acc gag act gga aca gcc aac ttt ggc atc tgg gat act aag ttt<br>Ile Thr Glu Thr Gly Thr Ala Asn Phe Gly Ile Trp Asp Thr Lys Phe<br>            20                  25                  30 | | 96 |
| ccc tct ggc gtt act gcg ctt tct cag gtc ctt tgg gga agc att ggt<br>Pro Ser Gly Val Thr Ala Leu Ser Gln Val Leu Trp Gly Ser Ile Gly<br>        35                  40                  45 | | 144 |
| tgg tcc gtt ggt gcc tgc caa gga gcc gtt ctt gca gcc gcc gat gac<br>Trp Ser Val Gly Ala Cys Gln Gly Ala Val Leu Ala Ala Ala Asp Asp<br>    50                  55                  60 | | 192 |
| aac agc gat cgc aga act atc ctc ttt gtt ggt gat ggc tca ttc cag<br>Asn Ser Asp Arg Arg Thr Ile Leu Phe Val Gly Asp Gly Ser Phe Gln<br>65                  70                  75                  80 | | 240 |
| ctc act gct caa gaa ttg agc aca atg att cgt ctc aag ctg aag ccc<br>Leu Thr Ala Gln Glu Leu Ser Thr Met Ile Arg Leu Lys Leu Lys Pro<br>                85                  90                  95 | | 288 |
| atc atc ttt gtc atc tgc aac gat ggc ttt acc att gaa cga ttc att<br>Ile Ile Phe Val Ile Cys Asn Asp Gly Phe Thr Ile Glu Arg Phe Ile<br>            100                 105                 110 | | 336 |
| cac ggc atg gaa gcc gag tac aac gac atc gca aat tgg gac ttc aag<br>His Gly Met Glu Ala Glu Tyr Asn Asp Ile Ala Asn Trp Asp Phe Lys<br>        115                 120                 125 | | 384 |
| gct ctg gtt gac gtc ttt ggc ggc tct aag acg gcc aag aag ttc gcc<br>Ala Leu Val Asp Val Phe Gly Gly Ser Lys Thr Ala Lys Lys Phe Ala<br>    130                 135                 140 | | 432 |
| gtc aag acc aag gac gag ctg gac agc ctt ctc aca gac cct acc ttt<br>Val Lys Thr Lys Asp Glu Leu Asp Ser Leu Leu Thr Asp Pro Thr Phe<br>145                 150                 155                 160 | | 480 |
| aac gcc gca gaa tgc ctc cag ttt gtc gag cta tat atg ccc aaa gaa<br>Asn Ala Ala Glu Cys Leu Gln Phe Val Glu Leu Tyr Met Pro Lys Glu<br>                165                 170                 175 | | 528 |
| gat gct cct cga gca ttg atc atg act gca gaa gct agc gcg agg aac<br>Asp Ala Pro Arg Ala Leu Ile Met Thr Ala Glu Ala Ser Ala Arg Asn<br>            180                 185                 190 | | 576 |
| aat gcc aag aca gag<br>Asn Ala Lys Thr Glu<br>        195 | | 591 |

<210> SEQ ID NO 6
<211> LENGTH: 197
<212> TYPE: PRT
<213> ORGANISM: Unknown
<220> FEATURE:
<223> OTHER INFORMATION: Fungal isolate from soil sample

<400> SEQUENCE: 6

Phe Phe Trp Pro Arg Val Gly Glu Phe Leu Lys Lys Asn Asp Ile Val
1               5                   10                  15

Ile Thr Glu Thr Gly Thr Ala Asn Phe Gly Ile Trp Asp Thr Lys Phe
            20                  25                  30

Pro Ser Gly Val Thr Ala Leu Ser Gln Val Leu Trp Gly Ser Ile Gly
        35                  40                  45

Trp Ser Val Gly Ala Cys Gln Gly Ala Val Leu Ala Ala Ala Asp Asp
    50                  55                  60

Asn Ser Asp Arg Arg Thr Ile Leu Phe Val Gly Asp Gly Ser Phe Gln
65                  70                  75                  80

Leu Thr Ala Gln Glu Leu Ser Thr Met Ile Arg Leu Lys Leu Lys Pro
                85                  90                  95

```
Ile Ile Phe Val Ile Cys Asn Asp Gly Phe Thr Ile Glu Arg Phe Ile
            100                 105                 110

His Gly Met Glu Ala Glu Tyr Asn Asp Ile Ala Asn Trp Asp Phe Lys
            115                 120                 125

Ala Leu Val Asp Val Phe Gly Gly Ser Lys Thr Ala Lys Lys Phe Ala
            130                 135                 140

Val Lys Thr Lys Asp Glu Leu Asp Ser Leu Leu Thr Asp Pro Thr Phe
145                 150                 155                 160

Asn Ala Ala Glu Cys Leu Gln Phe Val Glu Leu Tyr Met Pro Lys Glu
                165                 170                 175

Asp Ala Pro Arg Ala Leu Ile Met Thr Ala Glu Ala Ser Ala Arg Asn
                180                 185                 190

Asn Ala Lys Thr Glu
            195

<210> SEQ ID NO 7
<211> LENGTH: 678
<212> TYPE: DNA
<213> ORGANISM: Unknown
<220> FEATURE:
<221> NAME/KEY: CDS
<222> LOCATION: (1)...(678)
<223> OTHER INFORMATION: Fungal isolate from soil sample

<400> SEQUENCE: 7 aca tat cca ggt gtc cag atg agg ggt gtg ctg cga caa gtg att aag       48
Thr Tyr Pro Gly Val Gln Met Arg Gly Val Leu Arg Gln Val Ile Lys
 1               5                  10                  15 cag ctc gat gca tct gag atc aac gct cag cca gcg cca gtc gtc gag       96
Gln Leu Asp Ala Ser Glu Ile Asn Ala Gln Pro Ala Pro Val Val Glu
            20                  25                  30 aat gaa gtt gcc aaa aac cga gat aac tca ccc gtc att aca caa gct      144
Asn Glu Val Ala Lys Asn Arg Asp Asn Ser Pro Val Ile Thr Gln Ala
        35                  40                  45 ttc ttc tgg ccg cgc gtg gga gag ttc ctg aag aag aac gac atc gtc      192
Phe Phe Trp Pro Arg Val Gly Glu Phe Leu Lys Lys Asn Asp Ile Val
 50                  55                  60 att acc gag act gga aca gcc aac ttt ggc atc tgg gat act aag ttt      240
Ile Thr Glu Thr Gly Thr Ala Asn Phe Gly Ile Trp Asp Thr Lys Phe
 65                  70                  75                  80 ccc tct ggc gtt act gcg ctt tct cag gtc ctt tgg gga agc att ggt      288
Pro Ser Gly Val Thr Ala Leu Ser Gln Val Leu Trp Gly Ser Ile Gly
                85                  90                  95 tgg tcc gtt ggt gcc tgc caa gga gcc gtt ctt gca gcc gcc gat gac      336
Trp Ser Val Gly Ala Cys Gln Gly Ala Val Leu Ala Ala Ala Asp Asp
            100                 105                 110 aac agc gat cgc aga act atc ctc ttt gtt ggt gat ggc tca ttc cag      384
Asn Ser Asp Arg Arg Thr Ile Leu Phe Val Gly Asp Gly Ser Phe Gln
        115                 120                 125 ctc act gct caa gaa ttg agc aca atg att cgt ctc aag ctg aag ccc      432
Leu Thr Ala Gln Glu Leu Ser Thr Met Ile Arg Leu Lys Leu Lys Pro
130                 135                 140 atc atc ttt gtc atc tgc aac gat ggc ttt acc att gaa cga ttc att      480
Ile Ile Phe Val Ile Cys Asn Asp Gly Phe Thr Ile Glu Arg Phe Ile
145                 150                 155                 160 cac ggc atg gaa gcc gag tac aac gac atc gca aat tgg gac ttc aag      528
His Gly Met Glu Ala Glu Tyr Asn Asp Ile Ala Asn Trp Asp Phe Lys
                165                 170                 175 gct ctg gtt gac gtc ttt ggc ggc tct aag acg gcc aag aag ttc gcc      576
Ala Leu Val Asp Val Phe Gly Gly Ser Lys Thr Ala Lys Lys Phe Ala
```

```
Ala Leu Val Asp Val Phe Gly Gly Ser Lys Thr Ala Lys Lys Phe Ala
            180                 185                 190 gtc aag acc aag gac gag ctg gac agc ctt ctc aca gac cct acc ttt      624
Val Lys Thr Lys Asp Glu Leu Asp Ser Leu Leu Thr Asp Pro Thr Phe
            195                 200                 205 aac gcc gca gaa tgc ctc cag ttt gtc gag cta tat atg ccc aaa gaa      672
Asn Ala Ala Glu Cys Leu Gln Phe Val Glu Leu Tyr Met Pro Lys Glu
            210                 215                 220 gat gct                                                              678
Asp Ala
225
```

<210> SEQ ID NO 8
<211> LENGTH: 226
<212> TYPE: PRT
<213> ORGANISM: Unknown
<220> FEATURE:
<223> OTHER INFORMATION: Fungal isolate from soil sample

<400> SEQUENCE: 8

```
Thr Tyr Pro Gly Val Gln Met Arg Gly Val Leu Arg Gln Val Ile Lys
 1               5                  10                  15

Gln Leu Asp Ala Ser Glu Ile Asn Ala Gln Pro Ala Pro Val Val Glu
            20                  25                  30

Asn Glu Val Ala Lys Asn Arg Asp Asn Ser Pro Val Ile Thr Gln Ala
        35                  40                  45

Phe Phe Trp Pro Arg Val Gly Glu Phe Leu Lys Lys Asn Asp Ile Val
 50                  55                  60

Ile Thr Glu Thr Gly Thr Ala Asn Phe Gly Ile Trp Asp Thr Lys Phe
65                  70                  75                  80

Pro Ser Gly Val Thr Ala Leu Ser Gln Val Leu Trp Gly Ser Ile Gly
                85                  90                  95

Trp Ser Val Gly Ala Cys Gln Gly Ala Val Leu Ala Ala Ala Asp Asp
            100                 105                 110

Asn Ser Asp Arg Arg Thr Ile Leu Phe Val Gly Asp Gly Ser Phe Gln
        115                 120                 125

Leu Thr Ala Gln Glu Leu Ser Thr Met Ile Arg Leu Lys Leu Lys Pro
130                 135                 140

Ile Ile Phe Val Ile Cys Asn Asp Gly Phe Thr Ile Glu Arg Phe Ile
145                 150                 155                 160

His Gly Met Glu Ala Glu Tyr Asn Asp Ile Ala Asn Trp Asp Phe Lys
                165                 170                 175

Ala Leu Val Asp Val Phe Gly Gly Ser Lys Thr Ala Lys Lys Phe Ala
            180                 185                 190

Val Lys Thr Lys Asp Glu Leu Asp Ser Leu Leu Thr Asp Pro Thr Phe
        195                 200                 205

Asn Ala Ala Glu Cys Leu Gln Phe Val Glu Leu Tyr Met Pro Lys Glu
    210                 215                 220

Asp Ala
225
```

<210> SEQ ID NO 9
<211> LENGTH: 1636
<212> TYPE: DNA
<213> ORGANISM: Unknown
<220> FEATURE:
<221> NAME/KEY: CDS
<222> LOCATION: (1)...(1377)
<223> OTHER INFORMATION: Fungal isolate from soil sample

<400> SEQUENCE: 9

| | | | | | | | | | | | | | | | | |
|---|---|---|---|---|---|---|---|---|---|---|---|---|---|---|---|---|
| cga | aac | ggc | atg | ctc | ctc | cac | cac | acg | ctt | gga | aac | ggc | gac | ttc | aac | 48 |
| Arg | Asn | Gly | Met | Leu | Leu | His | His | Thr | Leu | Gly | Asn | Gly | Asp | Phe | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atc | ttt | gcc | aac | atg | agc | gct | caa | atc | tct | tgc | gaa | gtg | gcc | aag | ctc | 96 |
| Ile | Phe | Ala | Asn | Met | Ser | Ala | Gln | Ile | Ser | Cys | Glu | Val | Ala | Lys | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | aac | cct | gcc | gaa | att | gcg | acc | cag | atc | gac | cat | gcc | ctc | cgc | gtt | 144 |
| Thr | Asn | Pro | Ala | Glu | Ile | Ala | Thr | Gln | Ile | Asp | His | Ala | Leu | Arg | Val | |
| | 35 | | | | | 40 | | | | | 45 | | | | | |

| | | | | | | | | | | | | | | | | |
|---|---|---|---|---|---|---|---|---|---|---|---|---|---|---|---|---|
| tgc | ttc | att | cgt | tct | cgg | ccc | gtc | tac | atc | atg | ctt | ccc | acc | gat | atg | 192 |
| Cys | Phe | Ile | Arg | Ser | Arg | Pro | Val | Tyr | Ile | Met | Leu | Pro | Thr | Asp | Met | |
| 50 | | | | | 55 | | | | | 60 | | | | | | |

| | | | | | | | | | | | | | | | | |
|---|---|---|---|---|---|---|---|---|---|---|---|---|---|---|---|---|
| gtc | cag | gcc | aaa | gta | gaa | ggt | gcc | aga | ctc | aag | gaa | cca | att | gac | ttg | 240 |
| Val | Gln | Ala | Lys | Val | Glu | Gly | Ala | Arg | Leu | Lys | Glu | Pro | Ile | Asp | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tcg | gag | cct | cca | aat | gat | ccc | gag | aaa | gaa | gca | tac | gtc | gtt | gac | gtt | 288 |
| Ser | Glu | Pro | Pro | Asn | Asp | Pro | Glu | Lys | Glu | Ala | Tyr | Val | Val | Asp | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gtc | ctc | aag | tac | ctc | cgt | gct | gca | aag | aac | ccc | gtc | atc | ctt | gtc | gat | 336 |
| Val | Leu | Lys | Tyr | Leu | Arg | Ala | Ala | Lys | Asn | Pro | Val | Ile | Leu | Val | Asp | |
| | | 100 | | | | | 105 | | | | | 110 | | | | |

| | | | | | | | | | | | | | | | | |
|---|---|---|---|---|---|---|---|---|---|---|---|---|---|---|---|---|
| gct | tgt | gct | atc | cgt | cat | cgt | gtt | ctt | gat | gag | gtt | cat | gat | ctc | atc | 384 |
| Ala | Cys | Ala | Ile | Arg | His | Arg | Val | Leu | Asp | Glu | Val | His | Asp | Leu | Ile | |
| | | | 115 | | | | | 120 | | | | | 125 | | | |

| | | | | | | | | | | | | | | | | |
|---|---|---|---|---|---|---|---|---|---|---|---|---|---|---|---|---|
| gaa | aag | aca | aac | ctc | cct | gtc | ttt | gtc | act | cct | atg | ggc | aaa | ggt | gct | 432 |
| Glu | Lys | Thr | Asn | Leu | Pro | Val | Phe | Val | Thr | Pro | Met | Gly | Lys | Gly | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| gtt | aac | gaa | gaa | cac | ccg | aca | tat | ggt | ggt | gtc | tat | gcc | ggt | gac | ggc | 480 |
| Val | Asn | Glu | Glu | His | Pro | Thr | Tyr | Gly | Gly | Val | Tyr | Ala | Gly | Asp | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tca | cat | ccg | cct | caa | gtt | aag | gac | atg | gtt | gag | tct | tct | gat | ttg | ata | 528 |
| Ser | His | Pro | Pro | Gln | Val | Lys | Asp | Met | Val | Glu | Ser | Ser | Asp | Leu | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| ttg | aca | atc | ggt | gct | ctc | aag | agc | gac | ttc | aac | act | gct | ggc | ttc | tct | 576 |
| Leu | Thr | Ile | Gly | Ala | Leu | Lys | Ser | Asp | Phe | Asn | Thr | Ala | Gly | Phe | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | cgt | acc | tca | cag | ctg | aac | acg | att | gat | cta | cac | agc | gac | cac | tgc | 624 |
| Tyr | Arg | Thr | Ser | Gln | Leu | Asn | Thr | Ile | Asp | Leu | His | Ser | Asp | His | Cys | |
| | | 195 | | | | | 200 | | | | | 205 | | | | |

| | | | | | | | | | | | | | | | | |
|---|---|---|---|---|---|---|---|---|---|---|---|---|---|---|---|---|
| att | gtc | aaa | tac | tcg | aca | tat | cca | ggt | gtc | cag | atg | agg | ggt | gtg | ctg | 672 |
| Ile | Val | Lys | Tyr | Ser | Thr | Tyr | Pro | Gly | Val | Gln | Met | Arg | Gly | Val | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| cga | caa | gtg | att | aag | cag | ctc | gat | gca | tct | gag | atc | aac | gct | cag | cca | 720 |
| Arg | Gln | Val | Ile | Lys | Gln | Leu | Asp | Ala | Ser | Glu | Ile | Asn | Ala | Gln | Pro | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gcg | cca | gtc | gtc | gag | aat | gaa | gtt | gcc | aaa | aac | cga | gat | aac | tca | ccc | 768 |
| Ala | Pro | Val | Val | Glu | Asn | Glu | Val | Ala | Lys | Asn | Arg | Asp | Asn | Ser | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| gtc | att | aca | caa | gct | ttc | ttc | tgg | ccg | cgc | gtg | gga | gag | ttc | ctg | aag | 816 |
| Val | Ile | Thr | Gln | Ala | Phe | Phe | Trp | Pro | Arg | Val | Gly | Glu | Phe | Leu | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| aag | aac | gac | atc | gtc | att | acc | gag | act | gga | aca | gcc | aac | ttt | ggc | atc | 864 |
| Lys | Asn | Asp | Ile | Val | Ile | Thr | Glu | Thr | Gly | Thr | Ala | Asn | Phe | Gly | Ile | |
| | | 275 | | | | | 280 | | | | | 285 | | | | |

| | | | | | | | | | | | | | | | | |
|---|---|---|---|---|---|---|---|---|---|---|---|---|---|---|---|---|
| tgg | gat | act | aag | ttt | ccc | tct | ggc | gtt | act | gcg | ctt | tct | cag | gtc | ctt | 912 |
| Trp | Asp | Thr | Lys | Phe | Pro | Ser | Gly | Val | Thr | Ala | Leu | Ser | Gln | Val | Leu | |
| | 290 | | | | | 295 | | | | | 300 | | | | | |

```
tgg gga agc att ggt tgg tcc gtt ggt gcc tgc caa gga gcc gtt ctt      960
Trp Gly Ser Ile Gly Trp Ser Val Gly Ala Cys Gln Gly Ala Val Leu
305                 310                 315                 320 gca gcc gcc gat gac aac agc gat cgc aga act atc ctc ttt gtt ggt     1008
Ala Ala Ala Asp Asp Asn Ser Asp Arg Arg Thr Ile Leu Phe Val Gly
                325                 330                 335 gat ggc tca ttc cag ctc act gct caa gaa ttg agc aca atg att cgt     1056
Asp Gly Ser Phe Gln Leu Thr Ala Gln Glu Leu Ser Thr Met Ile Arg
            340                 345                 350 ctc aag ctg aag ccc atc atc ttt gtc atc tgc aac gat ggc ttt acc     1104
Leu Lys Leu Lys Pro Ile Ile Phe Val Ile Cys Asn Asp Gly Phe Thr
        355                 360                 365 att gaa cga ttc att cac ggc atg gaa gcc gag tac aac gac atc gca     1152
Ile Glu Arg Phe Ile His Gly Met Glu Ala Glu Tyr Asn Asp Ile Ala
    370                 375                 380 aat tgg gac ttc aag gct ctg gtt gac gtc ttt ggc ggc tct aag acg     1200
Asn Trp Asp Phe Lys Ala Leu Val Asp Val Phe Gly Gly Ser Lys Thr
385                 390                 395                 400 gcc aag aag ttc gcc gtc aag acc aag gac gag ctg gac agc ctt ctc     1248
Ala Lys Lys Phe Ala Val Lys Thr Lys Asp Glu Leu Asp Ser Leu Leu
                405                 410                 415 aca gac cct acc ttt aac gcc gca gaa tgc ctc cag ttt gtc gag cta     1296
Thr Asp Pro Thr Phe Asn Ala Ala Glu Cys Leu Gln Phe Val Glu Leu
            420                 425                 430 tat atg ccc aaa gaa gat gct cct cga gca ttg atc atg act gca gaa     1344
Tyr Met Pro Lys Glu Asp Ala Pro Arg Ala Leu Ile Met Thr Ala Glu
        435                 440                 445 gct agc gcg agg aac aat gcc aag aca gag taa agtggactgt catgaaggcc   1397
Ala Ser Ala Arg Asn Asn Ala Lys Thr Glu *
    450                 455 gatttaccac tcataaatt gtaatagacc tgatacacat agatcaaggc aggtaccgat    1457
cattaatcaa gcaggtttgg atggggaagg attttgaaaa tgaggaaacg atgggatgat   1517
atttggaata actggccatt attttgagta cttataaaca aatttgaagt tcaatttttt   1577
ttcaaaaaaa aaaaaaaaaa aaaaaaaaaa aaaaaaaaaa aaaaaaaaaa aaaaaaaa     1636

<210> SEQ ID NO 10
<211> LENGTH: 1374
<212> TYPE: DNA
<213> ORGANISM: Unknown
<220> FEATURE:
<221> NAME/KEY: CDS
<222> LOCATION: (1)...(1374)
<223> OTHER INFORMATION: Fungal isolate from soil sample

<400> SEQUENCE: 10 cga aac ggc atg ctc ctc cac cac acg ctt gga aac ggc gac ttc aac       48
Arg Asn Gly Met Leu Leu His His Thr Leu Gly Asn Gly Asp Phe Asn
1               5                   10                  15 atc ttt gcc aac atg agc gct caa atc tct tgc gaa gtg gcc aag ctc      96
Ile Phe Ala Asn Met Ser Ala Gln Ile Ser Cys Glu Val Ala Lys Leu
            20                  25                  30 acc aac cct gcc gaa att gcg acc cag atc gac cat gcc ctc cgc gtt     144
Thr Asn Pro Ala Glu Ile Ala Thr Gln Ile Asp His Ala Leu Arg Val
        35                  40                  45 tgc ttc att cgt tct cgg ccc gtc tac atc atg ctt ccc acc gat atg     192
Cys Phe Ile Arg Ser Arg Pro Val Tyr Ile Met Leu Pro Thr Asp Met
    50                  55                  60 gtc cag gcc aaa gta gaa ggt gcc aga ctc aag gaa cca att gac ttg     240
Val Gln Ala Lys Val Glu Gly Ala Arg Leu Lys Glu Pro Ile Asp Leu
65                  70                  75                  80
```

```
tcg gag cct cca aat gat ccc gag aaa gaa gca tac gtc gtt gac gtt      288
Ser Glu Pro Pro Asn Asp Pro Glu Lys Glu Ala Tyr Val Val Asp Val
                         85                  90                  95 gtc ctc aag tac ctc cgt gct gca aag aac ccc gtc atc ctt gtc gat      336
Val Leu Lys Tyr Leu Arg Ala Ala Lys Asn Pro Val Ile Leu Val Asp
             100                 105                 110 gct tgt gct atc cgt cat cgt gtt ctt gat gag gtt cat gat ctc atc      384
Ala Cys Ala Ile Arg His Arg Val Leu Asp Glu Val His Asp Leu Ile
         115                 120                 125 gaa aag aca aac ctc cct gtc ttt gtc act cct atg ggc aaa ggt gct      432
Glu Lys Thr Asn Leu Pro Val Phe Val Thr Pro Met Gly Lys Gly Ala
     130                 135                 140 gtt aac gaa gaa cac ccg aca tat ggt ggt gtc tat gcc ggt gac ggc      480
Val Asn Glu Glu His Pro Thr Tyr Gly Gly Val Tyr Ala Gly Asp Gly
145                 150                 155                 160 tca cat ccg cct caa gtt aag gac atg gtt gag tct tct gat ttg ata      528
Ser His Pro Pro Gln Val Lys Asp Met Val Glu Ser Ser Asp Leu Ile
                 165                 170                 175 ttg aca atc ggt gct ctc aag agc gac ttc aac act gct ggc ttc tct      576
Leu Thr Ile Gly Ala Leu Lys Ser Asp Phe Asn Thr Ala Gly Phe Ser
             180                 185                 190 tac cgt acc tca cag ctg aac acg att gat cta cac agc gac cac tgc      624
Tyr Arg Thr Ser Gln Leu Asn Thr Ile Asp Leu His Ser Asp His Cys
         195                 200                 205 att gtc aaa tac tcg aca tat cca ggt gtc cag atg agg ggt gtg ctg      672
Ile Val Lys Tyr Ser Thr Tyr Pro Gly Val Gln Met Arg Gly Val Leu
     210                 215                 220 cga caa gtg att aag cag ctc gat gca tct gag atc aac gct cag cca      720
Arg Gln Val Ile Lys Gln Leu Asp Ala Ser Glu Ile Asn Ala Gln Pro
225                 230                 235                 240 gcg cca gtc gtc gag aat gaa gtt gcc aaa aac cga gat aac tca ccc      768
Ala Pro Val Val Glu Asn Glu Val Ala Lys Asn Arg Asp Asn Ser Pro
                 245                 250                 255 gtc att aca caa gct ttc ttc tgg ccg cgc gtg gga gag ttc ctg aag      816
Val Ile Thr Gln Ala Phe Phe Trp Pro Arg Val Gly Glu Phe Leu Lys
             260                 265                 270 aag aac gac atc gtc att acc gag act gga aca gcc aac ttt ggc atc      864
Lys Asn Asp Ile Val Ile Thr Glu Thr Gly Thr Ala Asn Phe Gly Ile
         275                 280                 285 tgg gat act aag ttt ccc tct ggc gtt act gcg ctt tct cag gtc ctt      912
Trp Asp Thr Lys Phe Pro Ser Gly Val Thr Ala Leu Ser Gln Val Leu
     290                 295                 300 tgg gga agc att ggt tgg tcc gtt ggt gcc tgc caa gga gcc gtt ctt      960
Trp Gly Ser Ile Gly Trp Ser Val Gly Ala Cys Gln Gly Ala Val Leu
305                 310                 315                 320 gca gcc gcc gat gac aac agc gat cgc aga act atc ctc ttt gtt ggt     1008
Ala Ala Ala Asp Asp Asn Ser Asp Arg Arg Thr Ile Leu Phe Val Gly
                 325                 330                 335 gat ggc tca ttc cag ctc act gct caa gaa ttg agc aca atg att cgt     1056
Asp Gly Ser Phe Gln Leu Thr Ala Gln Glu Leu Ser Thr Met Ile Arg
             340                 345                 350 ctc aag ctg aag ccc atc atc ttt gtc atc tgc aac gat ggc ttt acc     1104
Leu Lys Leu Lys Pro Ile Ile Phe Val Ile Cys Asn Asp Gly Phe Thr
         355                 360                 365 att gaa cga ttc att cac ggc atg gaa gcc gag tac aac gac atc gca     1152
Ile Glu Arg Phe Ile His Gly Met Glu Ala Glu Tyr Asn Asp Ile Ala
     370                 375                 380 aat tgg gac ttc aag gct ctg gtt gac gtc ttt ggc ggc tct aag acg     1200
Asn Trp Asp Phe Lys Ala Leu Val Asp Val Phe Gly Gly Ser Lys Thr
```

```
                385                 390                 395                 400
gcc aag aag ttc gcc gtc aag acc aag gac gag ctg gac agc ctt ctc            1248
Ala Lys Lys Phe Ala Val Lys Thr Lys Asp Glu Leu Asp Ser Leu Leu
                405                 410                 415 aca gac cct acc ttt aac gcc gca gaa tgc ctc cag ttt gtc gag cta            1296
Thr Asp Pro Thr Phe Asn Ala Ala Glu Cys Leu Gln Phe Val Glu Leu
                420                 425                 430 tat atg ccc aaa gaa gat gct cct cga gca ttg atc atg act gca gaa            1344
Tyr Met Pro Lys Glu Asp Ala Pro Arg Ala Leu Ile Met Thr Ala Glu
                435                 440                 445 gct agc gcg agg aac aat gcc aag aca gag                                    1374
Ala Ser Ala Arg Asn Asn Ala Lys Thr Glu
        450                 455

<210> SEQ ID NO 11
<211> LENGTH: 458
<212> TYPE: PRT
<213> ORGANISM: Unknown
<220> FEATURE:
<223> OTHER INFORMATION: Fungal isolate from soil sample

<400> SEQUENCE: 11

Arg Asn Gly Met Leu His His Thr Leu Gly Asn Gly Asp Phe Asn
 1               5                  10                  15

Ile Phe Ala Asn Met Ser Ala Gln Ile Ser Cys Glu Val Ala Lys Leu
                20                  25                  30

Thr Asn Pro Ala Glu Ile Ala Thr Gln Ile Asp His Ala Leu Arg Val
            35                  40                  45

Cys Phe Ile Arg Ser Arg Pro Val Tyr Ile Met Leu Pro Thr Asp Met
        50                  55                  60

Val Gln Ala Lys Val Glu Gly Ala Arg Leu Lys Glu Pro Ile Asp Leu
 65                 70                  75                  80

Ser Glu Pro Pro Asn Asp Pro Glu Lys Glu Ala Tyr Val Val Asp Val
                85                  90                  95

Val Leu Lys Tyr Leu Arg Ala Ala Lys Asn Pro Val Ile Leu Val Asp
            100                 105                 110

Ala Cys Ala Ile Arg His Arg Val Leu Asp Glu Val His Asp Leu Ile
        115                 120                 125

Glu Lys Thr Asn Leu Pro Val Phe Val Thr Pro Met Gly Lys Gly Ala
    130                 135                 140

Val Asn Glu Glu His Pro Thr Tyr Gly Gly Val Tyr Ala Gly Asp Gly
145                 150                 155                 160

Ser His Pro Pro Gln Val Lys Asp Met Val Glu Ser Ser Asp Leu Ile
                165                 170                 175

Leu Thr Ile Gly Ala Leu Lys Ser Asp Phe Asn Thr Ala Gly Phe Ser
            180                 185                 190

Tyr Arg Thr Ser Gln Leu Asn Thr Ile Asp Leu His Ser Asp His Cys
        195                 200                 205

Ile Val Lys Tyr Ser Thr Tyr Pro Gly Val Gln Met Arg Gly Val Leu
    210                 215                 220

Arg Gln Val Ile Lys Gln Leu Asp Ala Ser Glu Ile Asn Ala Gln Pro
225                 230                 235                 240

Ala Pro Val Val Glu Asn Glu Val Ala Lys Asn Arg Asp Asn Ser Pro
                245                 250                 255

Val Ile Thr Gln Ala Phe Phe Trp Pro Arg Val Gly Glu Phe Leu Lys
            260                 265                 270
```

```
Lys Asn Asp Ile Val Ile Thr Glu Thr Gly Thr Ala Asn Phe Gly Ile
        275                 280                 285

Trp Asp Thr Lys Phe Pro Ser Gly Val Thr Ala Leu Ser Gln Val Leu
        290                 295                 300

Trp Gly Ser Ile Gly Trp Ser Val Gly Ala Cys Gln Gly Ala Val Leu
305                 310                 315                 320

Ala Ala Ala Asp Asp Asn Ser Asp Arg Arg Thr Ile Leu Phe Val Gly
                325                 330                 335

Asp Gly Ser Phe Gln Leu Thr Ala Gln Glu Leu Ser Thr Met Ile Arg
            340                 345                 350

Leu Lys Leu Lys Pro Ile Ile Phe Val Ile Cys Asn Asp Gly Phe Thr
        355                 360                 365

Ile Glu Arg Phe Ile His Gly Met Glu Ala Glu Tyr Asn Asp Ile Ala
        370                 375                 380

Asn Trp Asp Phe Lys Ala Leu Val Asp Val Phe Gly Gly Ser Lys Thr
385                 390                 395                 400

Ala Lys Lys Phe Ala Val Lys Thr Lys Asp Glu Leu Asp Ser Leu Leu
                405                 410                 415

Thr Asp Pro Thr Phe Asn Ala Ala Glu Cys Leu Gln Phe Val Glu Leu
            420                 425                 430

Tyr Met Pro Lys Glu Asp Ala Pro Arg Ala Leu Ile Met Thr Ala Glu
        435                 440                 445

Ala Ser Ala Arg Asn Asn Ala Lys Thr Glu
    450                 455

<210> SEQ ID NO 12
<211> LENGTH: 30
<212> TYPE: DNA
<213> ORGANISM: Unknown
<220> FEATURE:
<221> NAME/KEY: CDS
<222> LOCATION: (1)...(30)
<223> OTHER INFORMATION: Oligonucleotide for PCR amplicfication of GDC-1

<400> SEQUENCE: 12 tcc cag atg cca aag ttg gct gtt cca gtc                              30
Ser Gln Met Pro Lys Leu Ala Val Pro Val
  1               5                  10

<210> SEQ ID NO 13
<211> LENGTH: 2606
<212> TYPE: DNA
<213> ORGANISM: Unknown
<220> FEATURE:
<221> NAME/KEY: CDS
<222> LOCATION: (168)...(2258)
<223> OTHER INFORMATION: Fungal isolate from soil sample
<220> FEATURE:
<221> NAME/KEY: misc_feature
<222> LOCATION: 2370
<223> OTHER INFORMATION: n = A,T,C or G

<400> SEQUENCE: 13
caattgacga ggagtcgttg ttttcctctt tttctctctc tcccgcatcg cgcgcgtgga    60
ttgggccctt tttatctttt tctgcgatat cctcgactga gaacgacgac gacgagcacg   120
acgacgacga cacaggcgac gactgcgagg cagccccccac agccgcc atg atg ctc    176
                                                    Met Met Leu
                                                      1 cga agt cgc cag gcc tcc aag gcc ctg agg gcc ttg ggc cag gca cgg    224
Arg Ser Arg Gln Ala Ser Lys Ala Leu Arg Ala Leu Gly Gln Ala Arg
  5                  10                  15
```

-continued

| | |
|---|---|
| cac ttc acc tcg acg aca cag ccc gcc gcc gtg cag gcc ccg aga aag<br>His Phe Thr Ser Thr Thr Gln Pro Ala Ala Val Gln Ala Pro Arg Lys<br>20                   25                    30                   35 | 272 |
| gtc gcc tcc gga cag cgg aat caa gct acc gcc gcg acg gcc acc tct<br>Val Ala Ser Gly Gln Arg Asn Gln Ala Thr Ala Ala Thr Ala Thr Ser<br>                   40                    45                    50 | 320 |
| gcc gca ccc aat gtc cgc gcc acg ccg agt cct gcc ttc aat gcg gag<br>Ala Ala Pro Asn Val Arg Ala Thr Pro Ser Pro Ala Phe Asn Ala Glu<br>           55                    60                   65 | 368 |
| gag cag cag cag caa aaa cac agc cat gtc cag ccg ctg gtc aat ccc<br>Glu Gln Gln Gln Gln Lys His Ser His Val Gln Pro Leu Val Asn Pro<br>      70                    75                    80 | 416 |
| cag aag agc gac atg gat gag tcg ttc atc ggc aag acg ggc ggc gaa<br>Gln Lys Ser Asp Met Asp Glu Ser Phe Ile Gly Lys Thr Gly Gly Glu<br>85                   90                    95 | 464 |
| atc ttt cac gaa atg atg ctg aga caa ggc gtc aag cac atc ttt gga<br>Ile Phe His Glu Met Met Leu Arg Gln Gly Val Lys His Ile Phe Gly<br>100                   105                110                115 | 512 |
| tac ccc ggc ggc gcc atc ttg ccc gtc ttc gat gcc atc tac aac tca<br>Tyr Pro Gly Gly Ala Ile Leu Pro Val Phe Asp Ala Ile Tyr Asn Ser<br>                   120                125                130 | 560 |
| aaa cac ttc gac ttc atc ctg ccc aga cac gag cag ggc gcc ggc cac<br>Lys His Phe Asp Phe Ile Leu Pro Arg His Glu Gln Gly Ala Gly His<br>           135                    140                145 | 608 |
| atg gcc gag ggc tac gcc cgc gcg tcc ggc aag ccc ggc gtc gtc ctc<br>Met Ala Glu Gly Tyr Ala Arg Ala Ser Gly Lys Pro Gly Val Val Leu<br>                   150                155                160 | 656 |
| gtc acc tcg ggc ccc ggc gcc acc aac gtc gtg acc cca atg cag gac<br>Val Thr Ser Gly Pro Gly Ala Thr Asn Val Val Thr Pro Met Gln Asp<br>165                   170                175 | 704 |
| gcc ctg tcc gac ggc acg cca ctc gtc gtc ttt tgc ggc cag gtc ccg<br>Ala Leu Ser Asp Gly Thr Pro Leu Val Val Phe Cys Gly Gln Val Pro<br>180                   185                190                195 | 752 |
| acc tcg gcc atc ggc agc gat gcc ttc cag gag gcc gac gtc gtc ggc<br>Thr Ser Ala Ile Gly Ser Asp Ala Phe Gln Glu Ala Asp Val Val Gly<br>                   200                205                210 | 800 |
| atc tcc cgc gcc tgc acc aag tgg aac gtc atg gtc aag aac gtc gcg<br>Ile Ser Arg Ala Cys Thr Lys Trp Asn Val Met Val Lys Asn Val Ala<br>           215                    220                225 | 848 |
| gag ctg ccg cgg aga atc aac gag gcc ttt gag att gcc acg agc ggt<br>Glu Leu Pro Arg Arg Ile Asn Glu Ala Phe Glu Ile Ala Thr Ser Gly<br>      230                    235                240 | 896 |
| cgc ccc ggc ccc gtc ctc gtc gac ctg ccc aag gac gtc acc gcc ggc<br>Arg Pro Gly Pro Val Leu Val Asp Leu Pro Lys Asp Val Thr Ala Gly<br>245                   250                255 | 944 |
| atc ctg agg aga gcc atc ccc acg gag acg gcc ctg ccc gcg ctg ccg<br>Ile Leu Arg Arg Ala Ile Pro Thr Glu Thr Ala Leu Pro Ala Leu Pro<br>260                   265                270                275 | 992 |
| agc gcc gcc tcg cgc gcc gcc atg gag tcg agc cgg aaa cac ctc gag<br>Ser Ala Ala Ser Arg Ala Ala Met Glu Ser Ser Arg Lys His Leu Glu<br>                   280                285                290 | 1040 |
| cac acc atc aag cgc gtc gcc gac ctc gtc aac aag gcc aag cag cca<br>His Thr Ile Lys Arg Val Ala Asp Leu Val Asn Lys Ala Lys Gln Pro<br>               295                    300                305 | 1088 |
| gtc atc tac gcc ggc cag ggc atc atc cag tcc gag ggc ggg ccc gag<br>Val Ile Tyr Ala Gly Gln Gly Ile Ile Gln Ser Glu Gly Gly Pro Glu<br>           310                    315                320 | 1136 |
| ctc ctc aag gag ctg gcc gac aag gcc tcc atc ccc gtc acc acg acc<br>Leu Leu Lys Glu Leu Ala Asp Lys Ala Ser Ile Pro Val Thr Thr Thr | 1184 |

```
                    325                 330                 335
ctc cag ggc ctc ggc ggc ttc gac gag ctc gac gag aag tcg ctg cac      1232
Leu Gln Gly Leu Gly Gly Phe Asp Glu Leu Asp Glu Lys Ser Leu His
340                 345                 350                 355 atg ctc ggc atg cac ggc tcg gcc tac gcc aac atg gcc atg cag gag      1280
Met Leu Gly Met His Gly Ser Ala Tyr Ala Asn Met Ala Met Gln Glu
                    360                 365                 370 gcc gac ctc atc atc gcc ctc ggc gcg cgc ttc gac gac cgc gtc acc      1328
Ala Asp Leu Ile Ile Ala Leu Gly Ala Arg Phe Asp Asp Arg Val Thr
        375                 380                 385 ctc aac gtg gcc aag ttc gcg cct ggc gcg agg gcc gcc gcg gcc gag      1376
Leu Asn Val Ala Lys Phe Ala Pro Gly Ala Arg Ala Ala Ala Ala Glu
            390                 395                 400 aag cgc ggc ggc atc gtc cac ttc gag gtg atg ccc aag aac atc aac      1424
Lys Arg Gly Gly Ile Val His Phe Glu Val Met Pro Lys Asn Ile Asn
405                 410                 415 aag gtg gtg cag gcc acc gag gcc gtc gag ggc aac gtc ggc agc aac      1472
Lys Val Val Gln Ala Thr Glu Ala Val Glu Gly Asn Val Gly Ser Asn
420                 425                 430                 435 ctc aag ctc ctg ctg ccc gag gtg cag gcc aag acg atg gac gac cgc      1520
Leu Lys Leu Leu Leu Pro Glu Val Gln Ala Lys Thr Met Asp Asp Arg
                    440                 445                 450 aag gag tgg ttc ggc aag atc aac gag tgg aag aag aag tgg ccg ctg      1568
Lys Glu Trp Phe Gly Lys Ile Asn Glu Trp Lys Lys Lys Trp Pro Leu
                455                 460                 465 tcg cac tac gag cgt gcg gag cgc cac ggg ctc atc aag ccg cag acc      1616
Ser His Tyr Glu Arg Ala Glu Arg His Gly Leu Ile Lys Pro Gln Thr
            470                 475                 480 ctc atc gag gag ctg agc aag ctg acg gcg gac cgc aag gac aag acg      1664
Leu Ile Glu Glu Leu Ser Lys Leu Thr Ala Asp Arg Lys Asp Lys Thr
485                 490                 495 tac att gcc acc ggc gtc gga cag cac cag atg tgg acg gcc cag cac      1712
Tyr Ile Ala Thr Gly Val Gly Gln His Gln Met Trp Thr Ala Gln His
500                 505                 510                 515 ttc cgg tgg agg cac ccg cgc agc atg atc acg tcg ggt ggt ctc ggc      1760
Phe Arg Trp Arg His Pro Arg Ser Met Ile Thr Ser Gly Gly Leu Gly
                    520                 525                 530 act atg ggc ttc ggt ctg ccg gct gcc atc ggt gcc aag gtc gcg cag      1808
Thr Met Gly Phe Gly Leu Pro Ala Ala Ile Gly Ala Lys Val Ala Gln
                535                 540                 545 ccg gac gcc ctc gtc ttc gat atc gat ggc gac gcg tca ttt ggc atg      1856
Pro Asp Ala Leu Val Phe Asp Ile Asp Gly Asp Ala Ser Phe Gly Met
            550                 555                 560 acc ctg acg gag ctg gcc acg gcg gcg cag ttc aac att ggc gtc aag      1904
Thr Leu Thr Glu Leu Ala Thr Ala Ala Gln Phe Asn Ile Gly Val Lys
565                 570                 575 gtc att gtc ctc aac aac gag gag cag ggc atg gta acg cag tgg cag      1952
Val Ile Val Leu Asn Asn Glu Glu Gln Gly Met Val Thr Gln Trp Gln
580                 585                 590                 595 aac ctc ttc tac gag gac cgc tac gcg cac acg cac cag gtc aac cct      2000
Asn Leu Phe Tyr Glu Asp Arg Tyr Ala His Thr His Gln Val Asn Pro
                    600                 605                 610 gat ttc atg aag ctg gcc gag tcg atg cgc gtc cag ggc cgg cga tgc      2048
Asp Phe Met Lys Leu Ala Glu Ser Met Arg Val Gln Gly Arg Arg Cys
                615                 620                 625 gtg gac ccc gag gac gtg gtc gac agc ctg aag tgg ctg atc aac act      2096
Val Asp Pro Glu Asp Val Val Asp Ser Leu Lys Trp Leu Ile Asn Thr
            630                 635                 640 gac ggc ccg gcc ctg ctg gag gtt gtc acg gac aag aag gtg ccc gtc      2144
```

```
Asp Gly Pro Ala Leu Leu Glu Val Val Thr Asp Lys Lys Val Pro Val
        645                 650                 655 ctg ccc atg gtg ccg gcg ggc tcg gcc ctg cac gag ttt ttg gtg ttt        2192
Leu Pro Met Val Pro Ala Gly Ser Ala Leu His Glu Phe Leu Val Phe
660                 665                 670                 675 gac gga gaa aag gac aag aag cga cga gag ctg atg cgg gaa agg acc        2240
Asp Gly Glu Lys Asp Lys Lys Arg Arg Glu Leu Met Arg Glu Arg Thr
            680                 685                 690 tcg ggc ctg cac ggc tag ccgcagcaca cggggcggat tagcagcacc              2288
Ser Gly Leu His Gly  *
            695 cgacgacggg catccatcca tcaatcatct tctagtcatg ttcttttcat acctcttact      2348 ggcggagttt tgtgcagtta angcaaatcc gggcgcgaag cacaaaaagt tggaggagga      2408 gcagcgccga acggcggcgc ggtggtagca caggggtggc aatgtgacgg cgggtcgaag      2468 agcccgggca tggcagagta gggcggttgg ttcccatgag gcgagcgagc cgcgcgcggg      2528 cttgcggacg gacacaaaca aacaatgaat gaccattttt ccgagacgtg aaaaaaaaaa      2588 aaaaaaaaaa aaaaaaaa                                                   2606

<210> SEQ ID NO 14
<211> LENGTH: 2088
<212> TYPE: DNA
<213> ORGANISM: Unknown
<220> FEATURE:
<221> NAME/KEY: CDS
<222> LOCATION: (1)...(2088)
<223> OTHER INFORMATION: Fungal isolate from soil sample

<400> SEQUENCE: 14 atg atg ctc cga agt cgc cag gcc tcc aag gcc ctg agg gcc ttg ggc         48
Met Met Leu Arg Ser Arg Gln Ala Ser Lys Ala Leu Arg Ala Leu Gly
1               5                   10                  15 cag gca cgg cac ttc acc tcg acg aca cag ccc gcc gcc gtg cag gcc         96
Gln Ala Arg His Phe Thr Ser Thr Thr Gln Pro Ala Ala Val Gln Ala
            20                  25                  30 ccg aga aag gtc gcc tcc gga cag cgg aat caa gct acc gcc gcg acg        144
Pro Arg Lys Val Ala Ser Gly Gln Arg Asn Gln Ala Thr Ala Ala Thr
        35                  40                  45 gcc acc tct gcc gca ccc aat gtc cgc gcc acg ccg agt cct gcc ttc        192
Ala Thr Ser Ala Ala Pro Asn Val Arg Ala Thr Pro Ser Pro Ala Phe
    50                  55                  60 aat gcg gag gag cag cag cag caa aaa cac agc cat gtc cag ccg ctg        240
Asn Ala Glu Glu Gln Gln Gln Gln Lys His Ser His Val Gln Pro Leu
65                  70                  75                  80 gtc aat ccc cag aag agc gac atg gat gag tcg ttc atc ggc aag acg        288
Val Asn Pro Gln Lys Ser Asp Met Asp Glu Ser Phe Ile Gly Lys Thr
                85                  90                  95 ggc ggc gaa atc ttt cac gaa atg atg ctg aga caa ggc gtc aag cac        336
Gly Gly Glu Ile Phe His Glu Met Met Leu Arg Gln Gly Val Lys His
            100                 105                 110 atc ttt gga tac ccc ggc ggc gcc atc ttg ccc gtc ttc gat gcc atc        384
Ile Phe Gly Tyr Pro Gly Gly Ala Ile Leu Pro Val Phe Asp Ala Ile
        115                 120                 125 tac aac tca aaa cac ttc gac ttc atc ctg ccc aga cac gag cag ggc        432
Tyr Asn Ser Lys His Phe Asp Phe Ile Leu Pro Arg His Glu Gln Gly
    130                 135                 140 gcc ggc cac atg gcc gag ggc tac gcc cgc gcg tcc ggc aag ccc ggc        480
Ala Gly His Met Ala Glu Gly Tyr Ala Arg Ala Ser Gly Lys Pro Gly
145                 150                 155                 160
```

| | | |
|---|---|---|
| gtc gtc ctc gtc acc tcg ggc ccc ggc gcc acc aac gtc gtg acc cca<br>Val Val Leu Val Thr Ser Gly Pro Gly Ala Thr Asn Val Val Thr Pro<br>165 170 175 | | 528 |
| atg cag gac gcc ctg tcc gac ggc acg cca ctc gtc gtc ttt tgc ggc<br>Met Gln Asp Ala Leu Ser Asp Gly Thr Pro Leu Val Val Phe Cys Gly<br>180 185 190 | | 576 |
| cag gtc ccg acc tcg gcc atc ggc agc gat gcc ttc cag gag gcc gac<br>Gln Val Pro Thr Ser Ala Ile Gly Ser Asp Ala Phe Gln Glu Ala Asp<br>195 200 205 | | 624 |
| gtc gtc ggc atc tcc cgc gcc tgc acc aag tgg aac gtc atg gtc aag<br>Val Val Gly Ile Ser Arg Ala Cys Thr Lys Trp Asn Val Met Val Lys<br>210 215 220 | | 672 |
| aac gtc gcg gag ctg ccg cgg aga atc aac gag gcc ttt gag att gcc<br>Asn Val Ala Glu Leu Pro Arg Arg Ile Asn Glu Ala Phe Glu Ile Ala<br>225 230 235 240 | | 720 |
| acg agc ggt cgc ccc ggc ccc gtc ctc gtc gac ctg ccc aag gac gtc<br>Thr Ser Gly Arg Pro Gly Pro Val Leu Val Asp Leu Pro Lys Asp Val<br>245 250 255 | | 768 |
| acc gcc ggc atc ctg agg aga gcc atc ccc acg gag acg gcc ctg ccc<br>Thr Ala Gly Ile Leu Arg Arg Ala Ile Pro Thr Glu Thr Ala Leu Pro<br>260 265 270 | | 816 |
| gcg ctg ccg agc gcc gcc tcg cgc gcc gcc atg gag tcg agc cgg aaa<br>Ala Leu Pro Ser Ala Ala Ser Arg Ala Ala Met Glu Ser Ser Arg Lys<br>275 280 285 | | 864 |
| cac ctc gag cac acc atc aag cgc gtc gcc gac ctc gtc aac aag gcc<br>His Leu Glu His Thr Ile Lys Arg Val Ala Asp Leu Val Asn Lys Ala<br>290 295 300 | | 912 |
| aag cag cca gtc atc tac gcc ggc cag ggc atc atc cag tcc gag ggc<br>Lys Gln Pro Val Ile Tyr Ala Gly Gln Gly Ile Ile Gln Ser Glu Gly<br>305 310 315 320 | | 960 |
| ggg ccc gag ctc ctc aag gag ctg gcc gac aag gcc tcc atc ccc gtc<br>Gly Pro Glu Leu Leu Lys Glu Leu Ala Asp Lys Ala Ser Ile Pro Val<br>325 330 335 | | 1008 |
| acc acg acc ctc cag ggc ctc ggc ggc ttc gac gag ctc gac gag aag<br>Thr Thr Thr Leu Gln Gly Leu Gly Gly Phe Asp Glu Leu Asp Glu Lys<br>340 345 350 | | 1056 |
| tcg ctg cac atg ctc ggc atg cac ggc tcg gcc tac gcc aac atg gcc<br>Ser Leu His Met Leu Gly Met His Gly Ser Ala Tyr Ala Asn Met Ala<br>355 360 365 | | 1104 |
| atg cag gag gcc gac ctc atc atc gcc ctc ggc gcg cgc ttc gac gac<br>Met Gln Glu Ala Asp Leu Ile Ile Ala Leu Gly Ala Arg Phe Asp Asp<br>370 375 380 | | 1152 |
| cgc gtc acc ctc aac gtg gcc aag ttc gcg cct ggc gcg agg gcc gcc<br>Arg Val Thr Leu Asn Val Ala Lys Phe Ala Pro Gly Ala Arg Ala Ala<br>385 390 395 400 | | 1200 |
| gcg gcc gag aag cgc ggc ggc atc gtc cac ttc gag gtg atg ccc aag<br>Ala Ala Glu Lys Arg Gly Gly Ile Val His Phe Glu Val Met Pro Lys<br>405 410 415 | | 1248 |
| aac atc aac aag gtg gtg cag gcc acc gag gcc gtc gag ggc aac gtc<br>Asn Ile Asn Lys Val Val Gln Ala Thr Glu Ala Val Glu Gly Asn Val<br>420 425 430 | | 1296 |
| ggc agc aac ctc aag ctc ctg ctg ccc gag gtg cag gcc aag acg atg<br>Gly Ser Asn Leu Lys Leu Leu Leu Pro Glu Val Gln Ala Lys Thr Met<br>435 440 445 | | 1344 |
| gac gac cgc aag gag tgg ttc ggc aag atc aac gag tgg aag aag aag<br>Asp Asp Arg Lys Glu Trp Phe Gly Lys Ile Asn Glu Trp Lys Lys Lys<br>450 455 460 | | 1392 |
| tgg ccg ctg tcg cac tac gag cgt gcg gag cgc cac ggg ctc atc aag<br>Trp Pro Leu Ser His Tyr Glu Arg Ala Glu Arg His Gly Leu Ile Lys<br>465 470 475 480 | | 1440 |

-continued

```
ccg cag acc ctc atc gag gag ctg agc aag ctg acg gcg gac cgc aag    1488
Pro Gln Thr Leu Ile Glu Glu Leu Ser Lys Leu Thr Ala Asp Arg Lys
                485                 490                 495 gac aag acg tac att gcc acc ggc gtc gga cag cac cag atg tgg acg    1536
Asp Lys Thr Tyr Ile Ala Thr Gly Val Gly Gln His Gln Met Trp Thr
            500                 505                 510 gcc cag cac ttc cgg tgg agg cac ccg cgc agc atg atc acg tcg ggt    1584
Ala Gln His Phe Arg Trp Arg His Pro Arg Ser Met Ile Thr Ser Gly
        515                 520                 525 ggt ctc ggc act atg ggc ttc ggt ctg ccg gct gcc atc ggt gcc aag    1632
Gly Leu Gly Thr Met Gly Phe Gly Leu Pro Ala Ala Ile Gly Ala Lys
    530                 535                 540 gtc gcg cag ccg gac gcc ctc gtc ttc gat atc gat ggc gac gcg tca    1680
Val Ala Gln Pro Asp Ala Leu Val Phe Asp Ile Asp Gly Asp Ala Ser
545                 550                 555                 560 ttt ggc atg acc ctg acg gag ctg gcc acg gcg gcg cag ttc aac att    1728
Phe Gly Met Thr Leu Thr Glu Leu Ala Thr Ala Ala Gln Phe Asn Ile
                565                 570                 575 ggc gtc aag gtc att gtc ctc aac aac gag gag cag ggc atg gta acg    1776
Gly Val Lys Val Ile Val Leu Asn Asn Glu Glu Gln Gly Met Val Thr
            580                 585                 590 cag tgg cag aac ctc ttc tac gag gac cgc tac gcg cac acg cac cag    1824
Gln Trp Gln Asn Leu Phe Tyr Glu Asp Arg Tyr Ala His Thr His Gln
        595                 600                 605 gtc aac cct gat ttc atg aag ctg gcc gag tcg atg cgc gtc cag ggc    1872
Val Asn Pro Asp Phe Met Lys Leu Ala Glu Ser Met Arg Val Gln Gly
    610                 615                 620 cgg cga tgc gtg gac ccc gag gac gtg gtc gac agc ctg aag tgg ctg    1920
Arg Arg Cys Val Asp Pro Glu Asp Val Val Asp Ser Leu Lys Trp Leu
625                 630                 635                 640 atc aac act gac ggc ccg gcc ctg ctg gag gtt gtc acg gac aag aag    1968
Ile Asn Thr Asp Gly Pro Ala Leu Leu Glu Val Val Thr Asp Lys Lys
                645                 650                 655 gtg ccc gtc ctg ccc atg gtg ccg gcg ggc tcg gcc ctg cac gag ttt    2016
Val Pro Val Leu Pro Met Val Pro Ala Gly Ser Ala Leu His Glu Phe
            660                 665                 670 ttg gtg ttt gac gga gaa aag gac aag aag cga cga gag ctg atg cgg    2064
Leu Val Phe Asp Gly Glu Lys Asp Lys Lys Arg Arg Glu Leu Met Arg
        675                 680                 685 gaa agg acc tcg ggc ctg cac ggc                                    2088
Glu Arg Thr Ser Gly Leu His Gly
    690                 695
```

<210> SEQ ID NO 15
<211> LENGTH: 696
<212> TYPE: PRT
<213> ORGANISM: Unknown
<220> FEATURE:
<223> OTHER INFORMATION: Fungal isolate from soil sample

<400> SEQUENCE: 15

```
Met Met Leu Arg Ser Arg Gln Ala Ser Lys Ala Leu Arg Ala Leu Gly
1               5                   10                  15

Gln Ala Arg His Phe Thr Ser Thr Thr Gln Pro Ala Ala Val Gln Ala
            20                  25                  30

Pro Arg Lys Val Ala Ser Gly Arg Asn Gln Ala Thr Ala Ala Thr
        35                  40                  45

Ala Thr Ser Ala Ala Pro Asn Val Arg Ala Thr Pro Ser Pro Ala Phe
    50                  55                  60
```

-continued

```
Asn Ala Glu Glu Gln Gln Gln Lys His Ser His Val Gln Pro Leu
 65                  70                  75                  80

Val Asn Pro Gln Lys Ser Asp Met Asp Glu Ser Phe Ile Gly Lys Thr
                 85                  90                  95

Gly Gly Glu Ile Phe His Glu Met Met Leu Arg Gln Gly Val Lys His
                100                 105                 110

Ile Phe Gly Tyr Pro Gly Gly Ala Ile Leu Pro Val Phe Asp Ala Ile
                115                 120                 125

Tyr Asn Ser Lys His Phe Asp Phe Ile Leu Pro Arg His Glu Gln Gly
130                 135                 140

Ala Gly His Met Ala Glu Gly Tyr Ala Arg Ala Ser Gly Lys Pro Gly
145                 150                 155                 160

Val Val Leu Val Thr Ser Gly Pro Gly Ala Thr Asn Val Val Thr Pro
                165                 170                 175

Met Gln Asp Ala Leu Ser Asp Gly Thr Pro Leu Val Val Phe Cys Gly
                180                 185                 190

Gln Val Pro Thr Ser Ala Ile Gly Ser Asp Ala Phe Gln Glu Ala Asp
                195                 200                 205

Val Val Gly Ile Ser Arg Ala Cys Thr Lys Trp Asn Val Met Val Lys
                210                 215                 220

Asn Val Ala Glu Leu Pro Arg Arg Ile Asn Glu Ala Phe Glu Ile Ala
225                 230                 235                 240

Thr Ser Gly Arg Pro Gly Pro Val Leu Val Asp Leu Pro Lys Asp Val
                245                 250                 255

Thr Ala Gly Ile Leu Arg Arg Ala Ile Pro Thr Glu Thr Ala Leu Pro
                260                 265                 270

Ala Leu Pro Ser Ala Ala Ser Arg Ala Ala Met Glu Ser Ser Arg Lys
                275                 280                 285

His Leu Glu His Thr Ile Lys Arg Val Ala Asp Leu Val Asn Lys Ala
                290                 295                 300

Lys Gln Pro Val Ile Tyr Ala Gly Gln Gly Ile Ile Gln Ser Glu Gly
305                 310                 315                 320

Gly Pro Glu Leu Leu Lys Glu Leu Ala Asp Lys Ala Ser Ile Pro Val
                325                 330                 335

Thr Thr Thr Leu Gln Gly Leu Gly Gly Phe Asp Glu Leu Asp Glu Lys
                340                 345                 350

Ser Leu His Met Leu Gly Met His Gly Ser Ala Tyr Ala Asn Met Ala
                355                 360                 365

Met Gln Glu Ala Asp Leu Ile Ile Ala Leu Gly Ala Arg Phe Asp Asp
                370                 375                 380

Arg Val Thr Leu Asn Val Ala Lys Phe Ala Pro Gly Ala Arg Ala Ala
385                 390                 395                 400

Ala Ala Glu Lys Arg Gly Gly Ile Val His Phe Glu Val Met Pro Lys
                405                 410                 415

Asn Ile Asn Lys Val Val Gln Ala Thr Glu Ala Val Glu Gly Asn Val
                420                 425                 430

Gly Ser Asn Leu Lys Leu Leu Pro Glu Val Gln Ala Lys Thr Met
                435                 440                 445

Asp Asp Arg Lys Glu Trp Phe Gly Lys Ile Asn Glu Trp Lys Lys Lys
                450                 455                 460

Trp Pro Leu Ser His Tyr Glu Arg Ala Glu Arg His Gly Leu Ile Lys
465                 470                 475                 480

Pro Gln Thr Leu Ile Glu Glu Leu Ser Lys Leu Thr Ala Asp Arg Lys
```

```
                      485                 490                 495
Asp Lys Thr Tyr Ile Ala Thr Gly Val Gly Gln His Gln Met Trp Thr
                  500                 505                 510

Ala Gln His Phe Arg Trp Arg His Pro Arg Ser Met Ile Thr Ser Gly
              515                 520                 525

Gly Leu Gly Thr Met Gly Phe Gly Leu Pro Ala Ala Ile Gly Ala Lys
          530                 535                 540

Val Ala Gln Pro Asp Ala Leu Val Phe Asp Ile Asp Gly Asp Ala Ser
545                 550                 555                 560

Phe Gly Met Thr Leu Thr Glu Leu Ala Thr Ala Ala Gln Phe Asn Ile
                565                 570                 575

Gly Val Lys Val Ile Val Leu Asn Asn Glu Glu Gln Gly Met Val Thr
            580                 585                 590

Gln Trp Gln Asn Leu Phe Tyr Glu Asp Arg Tyr Ala His Thr His Gln
        595                 600                 605

Val Asn Pro Asp Phe Met Lys Leu Ala Glu Ser Met Arg Val Gln Gly
    610                 615                 620

Arg Arg Cys Val Asp Pro Glu Asp Val Asp Ser Leu Lys Trp Leu
625                 630                 635                 640

Ile Asn Thr Asp Gly Pro Ala Leu Leu Glu Val Val Thr Asp Lys Lys
                645                 650                 655

Val Pro Val Leu Pro Met Val Pro Ala Gly Ser Ala Leu His Glu Phe
            660                 665                 670

Leu Val Phe Asp Gly Glu Lys Asp Lys Lys Arg Arg Glu Leu Met Arg
        675                 680                 685

Glu Arg Thr Ser Gly Leu His Gly
    690                 695

<210> SEQ ID NO 16
<211> LENGTH: 563
<212> TYPE: PRT
<213> ORGANISM: Saccharomyces cerevisiae

<400> SEQUENCE: 16

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Arg Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Cys Thr
    130                 135                 140

Ala Pro Ala Glu Ile Asp Arg Cys Ile Arg Thr Thr Tyr Val Thr Gln
145                 150                 155                 160
```

-continued

```
Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Val Leu Ala
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Ser Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Val Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 17
```

<211> LENGTH: 550
<212> TYPE: PRT
<213> ORGANISM: Salmonella typhimurium

<400> SEQUENCE: 17

```
Met Gln Asn Pro Tyr Thr Val Ala Asp Tyr Leu Leu Asp Arg Leu Ala
 1               5                  10                  15

Gly Cys Gly Ile Gly His Leu Phe Gly Val Pro Gly Asp Tyr Asn Leu
             20                  25                  30

Gln Phe Leu Asp His Val Ile Asp His Pro Thr Leu Arg Trp Val Gly
         35                  40                  45

Cys Ala Asn Glu Leu Asn Ala Ala Tyr Ala Ala Asp Gly Tyr Ala Arg
 50                  55                  60

Met Ser Gly Ala Gly Ala Leu Leu Thr Thr Phe Gly Val Gly Glu Leu
 65                  70                  75                  80

Ser Ala Ile Asn Gly Ile Ala Gly Ser Tyr Ala Glu Tyr Val Pro Val
                 85                  90                  95

Leu His Ile Val Gly Ala Pro Cys Ser Ala Ala Gln Arg Gly Glu
             100                 105                 110

Leu Met His His Thr Leu Gly Asp Gly Asp Phe Arg His Phe Tyr Arg
             115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                 165                 170                 175

Ile Pro Pro Thr Gln Ala Leu Ala Leu Pro Val His Glu Ala Gln Ser
             180                 185                 190

Gly Val Glu Thr Ala Phe Arg Tyr His Ala Arg Gln Cys Leu Met Asn
         195                 200                 205

Ser Arg Arg Ile Ala Leu Leu Ala Asp Phe Leu Ala Gly Arg Phe Gly
210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                 245                 250                 255

Phe Val Gly Thr Tyr Ser Ala Gly Ala Ser Ser Lys Glu Val Arg Gln
             260                 265                 270

Ala Ile Glu Asp Ala Asp Arg Val Ile Cys Val Gly Thr Arg Phe Val
         275                 280                 285

Asp Thr Leu Thr Ala Gly Phe Thr Gln Gln Leu Pro Ala Glu Arg Thr
290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                 325                 330                 335

Cys Ala Phe Ala Pro Pro Thr Arg Ser Ala Gly Gln Pro Val Arg
             340                 345                 350

Ile Asp Lys Gly Glu Leu Thr Gln Glu Ser Phe Trp Gln Thr Leu Gln
         355                 360                 365

Gln Tyr Leu Lys Pro Gly Asp Ile Ile Leu Val Asp Gln Gly Thr Ala
370                 375                 380

Ala Phe Gly Ala Ala Ala Leu Ser Leu Pro Asp Gly Ala Glu Val Val
```

```
                385                 390                 395                 400
Leu Gln Pro Leu Trp Gly Ser Ile Gly Tyr Ser Leu Pro Ala Ala Phe
            405                 410                 415

Gly Ala Gln Thr Ala Cys Pro Asp Arg Arg Val Ile Leu Ile Ile Gly
            420                 425                 430

Asp Gly Ala Ala Gln Leu Thr Ile Gln Glu Met Gly Ser Met Leu Arg
            435                 440                 445

Asp Gly Gln Ala Pro Val Ile Leu Leu Leu Asn Asn Asp Gly Tyr Thr
            450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
            500                 505                 510

Glu Arg Leu Ala Arg Pro Gln Arg Leu Ser Phe Ile Glu Val Met Leu
            515                 520                 525

Pro Lys Ala Asp Leu Pro Glu Leu Leu Arg Thr Val Thr Arg Ala Leu
            530                 535                 540

Glu Ala Arg Asn Gly Gly
545                 550

<210> SEQ ID NO 18
<211> LENGTH: 568
<212> TYPE: PRT
<213> ORGANISM: Zymomonas mobilis

<400> SEQUENCE: 18

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala His Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Ala Lys Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Asp Glu Thr Leu Lys Phe Ile Ala Asn
        195                 200                 205
```

```
Arg Asp Lys Val Ala Val Leu Val Gly Ser Lys Leu Arg Ala Ala Gly
    210                 215                 220

Ala Glu Glu Ala Ala Val Lys Phe Thr Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
                260                 265                 270

Thr Met Lys Glu Ala Asp Ala Val Ile Ala Leu Ala Pro Val Phe Asn
            275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Arg Arg Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ser Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
    355                 360                 365

Glu Ile Ala Arg Gln Val Glu Ala Leu Leu Thr Pro Asn Thr Thr Val
370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
    435                 440                 445

Glu Val Ala Gln Met Val Arg Leu Lys Leu Pro Val Ile Ile Phe Leu
450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Ala Lys Gly Leu Lys Ala
            500                 505                 510

Lys Thr Gly Gly Glu Leu Ala Glu Ala Ile Lys Val Ala Leu Ala Asn
    515                 520                 525

Thr Asp Gly Pro Thr Leu Ile Glu Cys Phe Ile Gly Arg Glu Asp Cys
530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565
```

<210> SEQ ID NO 19
<211> LENGTH: 687
<212> TYPE: PRT
<213> ORGANISM: Saccharomyces cerevisiae

<400> SEQUENCE: 19

```
Met Ile Arg Gln Ser Thr Leu Lys Asn Phe Ala Ile Lys Arg Cys Phe
1               5                   10                  15
```

-continued

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
    210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285

Ile Asn Lys Ala Ala Asp Leu Ile Asn Leu Ala Lys Lys Pro Val Leu
    290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
        355                 360                 365

Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Ala Glu Gly Arg
385                 390                 395                 400

Gly Gly Ile Ile His Phe Glu Val Ser Pro Lys Asn Ile Asn Lys Val
                405                 410                 415

Val Gln Thr Gln Ile Ala Val Glu Gly Asp Ala Thr Thr Asn Leu Gly
            420                 425                 430

```
Lys Met Met Ser Lys Ile Phe Pro Val Lys Glu Arg Ser Glu Trp Phe
            435                 440                 445

Ala Gln Ile Asn Lys Trp Lys Lys Glu Tyr Pro Tyr Ala Tyr Met Glu
        450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
            500                 505                 510

Pro His Thr Phe Ile Thr Ser Gly Leu Gly Thr Met Gly Tyr Gly
            515                 520                 525

Leu Pro Ala Ala Ile Gly Ala Gln Val Ala Lys Pro Glu Ser Leu Val
        530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
        595                 600                 605

Ala Glu Ala Met Gly Leu Lys Gly Leu Arg Val Lys Lys Gln Glu Glu
        610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Gly Lys His
        675                 680                 685

<210> SEQ ID NO 20
<211> LENGTH: 686
<212> TYPE: PRT
<213> ORGANISM: Magnaporthe grisea

<400> SEQUENCE: 20

Met Leu Arg Thr Val Gly Arg Lys Ala Leu Arg Gly Ser Ser Lys Gly
1               5                   10                  15

Cys Ser Arg Thr Ile Ser Thr Leu Lys Pro Ala Thr Ala Thr Ile Ala
            20                  25                  30

Lys Pro Gly Ser Arg Thr Leu Ser Thr Pro Ala Thr Ala Thr Ala Thr
        35                  40                  45

Ala Pro Arg Thr Lys Pro Ser Ala Ser Phe Asn Ala Arg Arg Asp Pro
    50                  55                  60

Gln Pro Leu Val Asn Pro Arg Ser Gly Glu Ala Asp Glu Ser Phe Ile
65                  70                  75                  80

Gly Lys Thr Gly Gly Glu Ile Phe His Glu Met Met Leu Arg Gln Asn
                85                  90                  95

Val Lys His Ile Phe Gly Tyr Pro Gly Gly Ala Ile Leu Pro Val Phe
            100                 105                 110

Asp Ala Ile Tyr Asn Ser Lys His Ile Asp Phe Val Leu Pro Lys His
        115                 120                 125
```

```
Glu Gln Gly Ala Gly His Met Ala Glu Gly Tyr Ala Arg Ala Ser Gly
    130                 135                 140

Lys Pro Gly Val Val Leu Val Thr Ser Gly Pro Gly Ala Thr Asn Val
145                 150                 155                 160

Ile Thr Pro Met Ala Asp Ala Leu Ala Asp Gly Thr Pro Leu Val Val
                165                 170                 175

Phe Ser Gly Gln Val Val Thr Ser Asp Ile Gly Ser Asp Ala Phe Gln
            180                 185                 190

Glu Ala Asp Val Ile Gly Ile Ser Arg Ser Cys Thr Lys Trp Asn Val
        195                 200                 205

Met Val Lys Ser Ala Asp Glu Leu Pro Arg Arg Ile Asn Glu Ala Phe
    210                 215                 220

Glu Ile Ala Thr Ser Gly Arg Pro Gly Pro Val Leu Val Asp Pro Ala
225                 230                 235                 240

Lys Asp Val Thr Ala Ser Val Leu Arg Arg Ala Ile Pro Thr Glu Thr
                245                 250                 255

Ser Ile Pro Ser Ile Ser Ala Ala Ala Arg Ala Val Gln Glu Ala Gly
            260                 265                 270

Arg Lys Gln Leu Glu His Ser Ile Lys Arg Val Ala Asp Leu Val Asn
        275                 280                 285

Ile Ala Lys Lys Pro Val Ile Tyr Ala Gly Gln Gly Val Ile Leu Ser
    290                 295                 300

Glu Gly Gly Val Glu Leu Leu Lys Ala Leu Ala Asp Lys Ala Ser Ile
305                 310                 315                 320

Pro Val Thr Thr Thr Leu His Gly Leu Gly Ala Phe Asp Glu Leu Asp
                325                 330                 335

Glu Lys Ala Leu His Met Leu Gly Met His Gly Ser Ala Tyr Ala Asn
            340                 345                 350

Met Ser Met Gln Glu Ala Asp Leu Ile Ile Ala Leu Gly Gly Arg Phe
        355                 360                 365

Asp Asp Arg Val Thr Gly Ser Ile Pro Lys Phe Ala Pro Ala Ala Lys
    370                 375                 380

Leu Ala Ala Ala Glu Gly Arg Gly Gly Ile Val His Phe Glu Ile Met
385                 390                 395                 400

Pro Lys Asn Ile Asn Lys Val Val Gln Ala Thr Glu Ala Ile Glu Gly
                405                 410                 415

Asp Val Ala Ser Asn Leu Lys Leu Leu Leu Pro Lys Ile Glu Gln Arg
            420                 425                 430

Ser Met Thr Asp Arg Lys Glu Trp Phe Asp Gln Ile Lys Glu Trp Lys
        435                 440                 445

Glu Lys Trp Pro Leu Ser His Tyr Glu Arg Ala Glu Arg Ser Gly Leu
    450                 455                 460

Ile Lys Pro Gln Thr Leu Ile Glu Glu Leu Ser Asn Leu Thr Ala Asp
465                 470                 475                 480

Arg Lys Asp Met Thr Tyr Ile Thr Thr Gly Val Gly Gln His Gln Met
                485                 490                 495

Trp Thr Ala Gln His Phe Arg Trp Arg His Pro Arg Ser Met Ile Thr
            500                 505                 510

Ser Gly Gly Leu Gly Thr Met Gly Tyr Gly Leu Pro Ala Ala Ile Gly
        515                 520                 525

Ala Lys Val Ala Arg Pro Asp Ala Leu Val Ile Asp Ile Asp Gly Asp
    530                 535                 540
```

```
Ala Ser Phe Asn Met Thr Leu Thr Glu Leu Ser Thr Ala Ala Gln Phe
545                 550                 555                 560

Asn Ile Gly Val Lys Val Ile Val Leu Asn Asn Glu Glu Gln Gly Met
                565                 570                 575

Val Thr Gln Trp Gln Asn Leu Phe Tyr Glu Asp Arg Tyr Ser His Thr
            580                 585                 590

His Gln Arg Asn Pro Asp Phe Met Lys Leu Ala Asp Ala Met Asp Val
        595                 600                 605

Gln His Arg Arg Val Ser Lys Pro Asp Asp Val Gly Asp Ala Leu Thr
    610                 615                 620

Trp Leu Ile Asn Thr Asp Gly Pro Ala Leu Leu Glu Val Met Thr Asp
625                 630                 635                 640

Lys Lys Val Pro Val Leu Pro Met Val Pro Gly Gly Asn Gly Leu His
                645                 650                 655

Glu Phe Ile Thr Phe Asp Ala Ser Lys Asp Lys Gln Arg Arg Glu Leu
            660                 665                 670

Met Arg Ala Arg Thr Asn Gly Leu His Gly Arg Thr Ala Val
        675                 680                 685

<210> SEQ ID NO 21
<211> LENGTH: 1728
<212> TYPE: DNA
<213> ORGANISM: Unknown
<220> FEATURE:
<223> OTHER INFORMATION: Fungal isolate from soil sample
<220> FEATURE:
<221> NAME/KEY: CDS
<222> LOCATION: (1)...(1728)

<400> SEQUENCE: 21 atg gcc agc atc aac atc agg gtg cag aat ctc gag caa ccc atg gac     48
Met Ala Ser Ile Asn Ile Arg Val Gln Asn Leu Glu Gln Pro Met Asp
1               5                   10                  15 gtt gcc gag tat ctt ttc cgg cgt ctc cac gaa atc ggc att cgc tcc     96
Val Ala Glu Tyr Leu Phe Arg Arg Leu His Glu Ile Gly Ile Arg Ser
            20                  25                  30 atc cac ggt ctt cca ggc gat tac aac cct ctt gcc ctc gac tat ttg    144
Ile His Gly Leu Pro Gly Asp Tyr Asn Pro Leu Ala Leu Asp Tyr Leu
        35                  40                  45 cca tca tgt ggc ctg aga tgg gtt ggc agc gtc aac gaa ctc aat gct    192
Pro Ser Cys Gly Leu Arg Trp Val Gly Ser Val Asn Glu Leu Asn Ala
    50                  55                  60 gct tat gct gct gat ggc tat gcc cgc gtc aag cag atg gga gct ctc    240
Ala Tyr Ala Ala Asp Gly Tyr Ala Arg Val Lys Gln Met Gly Ala Leu
65                  70                  75                  80 atc acc act ttt gga gtg gga gag ctc tca gcc atc aat ggc gtt gcc    288
Ile Thr Thr Phe Gly Val Gly Glu Leu Ser Ala Ile Asn Gly Val Ala
                85                  90                  95 ggt gcc ttt tcg gaa cac gtc cca gtc gtt cac att gtt ggc tgc cct    336
Gly Ala Phe Ser Glu His Val Pro Val Val His Ile Val Gly Cys Pro
            100                 105                 110 tcc act gcc tcg cag cga aac ggc atg ctc ctc cac cac acg ctt gga    384
Ser Thr Ala Ser Gln Arg Asn Gly Met Leu Leu His His Thr Leu Gly
        115                 120                 125 aac ggc gac ttc aac atc ttt gcc aac atg agc gct caa atc tct tgc    432
Asn Gly Asp Phe Asn Ile Phe Ala Asn Met Ser Ala Gln Ile Ser Cys
    130                 135                 140 gaa gtg gcc aag ctc acc aac cct gcc gaa att gcg acc cag atc gac    480
Glu Val Ala Lys Leu Thr Asn Pro Ala Glu Ile Ala Thr Gln Ile Asp
145                 150                 155                 160
```

```
cat gcc ctc cgc gtt tgc ttc att cgt tct cgg ccc gtc tac atc atg      528
His Ala Leu Arg Val Cys Phe Ile Arg Ser Arg Pro Val Tyr Ile Met
            165                 170                 175 ctt ccc acc gat atg gtc cag gcc aaa gta gaa ggt gcc aga ctc aag      576
Leu Pro Thr Asp Met Val Gln Ala Lys Val Glu Gly Ala Arg Leu Lys
        180                 185                 190 gaa cca att gac ttg tcg gag cct cca aat gat ccc gag aaa gaa gca      624
Glu Pro Ile Asp Leu Ser Glu Pro Pro Asn Asp Pro Glu Lys Glu Ala
            195                 200                 205 tac gtc gtt gac gtt gtc ctc aag tac ctc cgt gct gca aag aac ccc      672
Tyr Val Val Asp Val Val Leu Lys Tyr Leu Arg Ala Ala Lys Asn Pro
        210                 215                 220 gtc atc ctt gtc gat gct tgt gct atc cgt cat cgt gtt ctt gat gag      720
Val Ile Leu Val Asp Ala Cys Ala Ile Arg His Arg Val Leu Asp Glu
225                 230                 235                 240 gtt cat gat ctc atc gaa aag aca aac ctc ccc gtc ttt gtc act cct      768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc      816
Met Gly Lys Gly Ala Val Asn Glu Glu His Pro Thr Tyr Gly Gly Val
            260                 265                 270 tat gcc ggt gac ggc tca cat ccg cct caa gtt aag gac atg gtt gag      864
Tyr Ala Gly Asp Gly Ser His Pro Pro Gln Val Lys Asp Met Val Glu
        275                 280                 285 tct tct gat ttg ata ttg aca atc ggt gct ctc aag agc gac ttc aac      912
Ser Ser Asp Leu Ile Leu Thr Ile Gly Ala Leu Lys Ser Asp Phe Asn
            290                 295                 300 act gct ggc ttc tct tac cgt acc tca cag ctg aac acg att gat cta      960
Thr Ala Gly Phe Ser Tyr Arg Thr Ser Gln Leu Asn Thr Ile Asp Leu
305                 310                 315                 320 cac agc gac cac tgc att gtc aaa tac tcg aca tat cca ggt gtc cag     1008
His Ser Asp His Cys Ile Val Lys Tyr Ser Thr Tyr Pro Gly Val Gln
                325                 330                 335 atg agg ggt gtg ctg cga caa gtg att aag cag ctc gat gca tct gag     1056
Met Arg Gly Val Leu Arg Gln Val Ile Lys Gln Leu Asp Ala Ser Glu
            340                 345                 350 atc aac gct cag cca gcg cca gtc gtc gag aat gaa gtt gcc aaa aac     1104
Ile Asn Ala Gln Pro Ala Pro Val Val Glu Asn Glu Val Ala Lys Asn
        355                 360                 365 cga gat aac tca ccc gtc att aca caa gct ttc ttc tgg ccg cgc gtg     1152
Arg Asp Asn Ser Pro Val Ile Thr Gln Ala Phe Phe Trp Pro Arg Val
            370                 375                 380 gga gag ttc ctg aag aag aac gac atc gtc att acc gag act gga aca     1200
Gly Glu Phe Leu Lys Lys Asn Asp Ile Val Ile Thr Glu Thr Gly Thr
385                 390                 395                 400 gcc aac ttt ggc atc tgg gat act aag ttt ccc tct ggc gtt act gcg     1248
Ala Asn Phe Gly Ile Trp Asp Thr Lys Phe Pro Ser Gly Val Thr Ala
                405                 410                 415 ctt tct cag gtc ctt tgg gga agc att ggt tgg tcc gtt ggt gcc tgc     1296
Leu Ser Gln Val Leu Trp Gly Ser Ile Gly Trp Ser Val Gly Ala Cys
            420                 425                 430 caa gga gcc gtt ctt gca gcc gcc gat gac aac agc gat cgc aga act     1344
Gln Gly Ala Val Leu Ala Ala Ala Asp Asp Asn Ser Asp Arg Arg Thr
        435                 440                 445 atc ctc ttt gtt ggt gat ggc tca ttc cag ctc act gct caa gaa ttg     1392
Ile Leu Phe Val Gly Asp Gly Ser Phe Gln Leu Thr Ala Gln Glu Leu
            450                 455                 460 agc aca atg att cgt ctc aag ctg aag ccc atc atc ttt gtc atc tgc     1440
Ser Thr Met Ile Arg Leu Lys Leu Lys Pro Ile Ile Phe Val Ile Cys
```

```
                465                 470                 475                 480
aac gat ggc ttt acc att gaa cga ttc att cac ggc atg gaa gcc gag          1488
Asn Asp Gly Phe Thr Ile Glu Arg Phe Ile His Gly Met Glu Ala Glu
                        485                 490                 495 tac aac gac atc gca aat tgg gac ttc aag gct ctg gtt gac gtc ttt          1536
Tyr Asn Asp Ile Ala Asn Trp Asp Phe Lys Ala Leu Val Asp Val Phe
                500                 505                 510 ggc ggc tct aag acg gcc aag aag ttc gcc gtc aag acc aag gac gag          1584
Gly Gly Ser Lys Thr Ala Lys Lys Phe Ala Val Lys Thr Lys Asp Glu
            515                 520                 525 ctg gac agc ctt ctc aca gac cct acc ttt aac gcc gca gaa tgc ctc          1632
Leu Asp Ser Leu Leu Thr Asp Pro Thr Phe Asn Ala Ala Glu Cys Leu
        530                 535                 540 cag ttt gtc gag cta tat atg ccc aaa gaa gat gct cct cga gca ttg          1680
Gln Phe Val Glu Leu Tyr Met Pro Lys Glu Asp Ala Pro Arg Ala Leu
545                 550                 555                 560 atc atg acg gca gaa gct agc gcg agg aac aat gcc aag aca gag taa          1728
Ile Met Thr Ala Glu Ala Ser Ala Arg Asn Asn Ala Lys Thr Glu  *
                565                 570                 575

<210> SEQ ID NO 22
<211> LENGTH: 575
<212> TYPE: PRT
<213> ORGANISM: Unknown
<220> FEATURE:
<223> OTHER INFORMATION: Fungal isolate from soil sample

<400> SEQUENCE: 22

Met Ala Ser Ile Asn Ile Arg Val Gln Asn Leu Glu Gln Pro Met Asp
 1               5                  10                  15

Val Ala Glu Tyr Leu Phe Arg Arg Leu His Glu Ile Gly Ile Arg Ser
            20                  25                  30

Ile His Gly Leu Pro Gly Asp Tyr Asn Pro Leu Ala Leu Asp Tyr Leu
        35                  40                  45

Pro Ser Cys Gly Leu Arg Trp Val Gly Ser Val Asn Glu Leu Asn Ala
    50                  55                  60

Ala Tyr Ala Ala Asp Gly Tyr Ala Arg Val Lys Gln Met Gly Ala Leu
65                  70                  75                  80

Ile Thr Thr Phe Gly Val Gly Glu Leu Ser Ala Ile Asn Gly Val Ala
                85                  90                  95

Gly Ala Phe Ser Glu His Val Pro Val Val His Ile Val Gly Cys Pro
            100                 105                 110

Ser Thr Ala Ser Gln Arg Asn Gly Met Leu Leu His His Thr Leu Gly
        115                 120                 125

Asn Gly Asp Phe Asn Ile Phe Ala Asn Met Ser Ala Gln Ile Ser Cys
    130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
                165                 170                 175

Leu Pro Thr Asp Met Val Gln Ala Lys Val Glu Gly Ala Arg Leu Lys
            180                 185                 190

Glu Pro Ile Asp Leu Ser Glu Pro Asn Asp Pro Glu Lys Glu Ala
        195                 200                 205

Tyr Val Val Asp Val Leu Lys Tyr Leu Arg Ala Ala Lys Asn Pro
    210                 215                 220

Val Ile Leu Val Asp Ala Cys Ala Ile Arg His Arg Val Leu Asp Glu
```

```
                225                 230                 235                 240
Val His Asp Leu Ile Glu Lys Thr Asn Leu Pro Val Phe Val Thr Pro
                    245                 250                 255
Met Gly Lys Gly Ala Val Asn Glu Glu His Pro Thr Tyr Gly Gly Val
                260                 265                 270
Tyr Ala Gly Asp Gly Ser His Pro Pro Gln Val Lys Asp Met Val Glu
            275                 280                 285
Ser Ser Asp Leu Ile Leu Thr Ile Gly Ala Leu Lys Ser Asp Phe Asn
        290                 295                 300
Thr Ala Gly Phe Ser Tyr Arg Thr Ser Gln Leu Asn Thr Ile Asp Leu
305                 310                 315                 320
His Ser Asp His Cys Ile Val Lys Tyr Ser Thr Tyr Pro Gly Val Gln
                325                 330                 335
Met Arg Gly Val Leu Arg Gln Val Ile Lys Gln Leu Asp Ala Ser Glu
                340                 345                 350
Ile Asn Ala Gln Pro Ala Pro Val Glu Asn Glu Val Ala Lys Asn
            355                 360                 365
Arg Asp Asn Ser Pro Val Ile Thr Gln Ala Phe Phe Trp Pro Arg Val
370                 375                 380
Gly Glu Phe Leu Lys Lys Asn Asp Ile Val Ile Thr Glu Thr Gly Thr
385                 390                 395                 400
Ala Asn Phe Gly Ile Trp Asp Thr Lys Phe Pro Ser Gly Val Thr Ala
                405                 410                 415
Leu Ser Gln Val Leu Trp Gly Ser Ile Gly Trp Ser Val Gly Ala Cys
            420                 425                 430
Gln Gly Ala Val Leu Ala Ala Asp Asp Asn Ser Asp Arg Arg Thr
        435                 440                 445
Ile Leu Phe Val Gly Asp Gly Ser Phe Gln Leu Thr Ala Gln Glu Leu
    450                 455                 460
Ser Thr Met Ile Arg Leu Lys Leu Lys Pro Ile Ile Phe Val Ile Cys
465                 470                 475                 480
Asn Asp Gly Phe Thr Ile Glu Arg Phe Ile His Gly Met Glu Ala Glu
                485                 490                 495
Tyr Asn Asp Ile Ala Asn Trp Asp Phe Lys Ala Leu Val Asp Val Phe
            500                 505                 510
Gly Gly Ser Lys Thr Ala Lys Lys Phe Ala Val Lys Thr Lys Asp Glu
        515                 520                 525
Leu Asp Ser Leu Leu Thr Asp Pro Thr Phe Asn Ala Ala Glu Cys Leu
    530                 535                 540
Gln Phe Val Glu Leu Tyr Met Pro Lys Glu Asp Ala Pro Arg Ala Leu
545                 550                 555                 560
Ile Met Thr Ala Glu Ala Ser Ala Arg Asn Asn Ala Lys Thr Glu
                565                 570                 575

<210> SEQ ID NO 23
<211> LENGTH: 1728
<212> TYPE: DNA
<213> ORGANISM: Unknown
<220> FEATURE:
<223> OTHER INFORMATION: Fungal isolate from soil sample
<220> FEATURE:
<221> NAME/KEY: CDS
<222> LOCATION: (1)...(1728)

<400> SEQUENCE: 23 atg gcc agc atc aac atc agg gtg cag aat ctc gag caa ccc atg gac        48
```

```
Met Ala Ser Ile Asn Ile Arg Val Gln Asn Leu Glu Gln Pro Met Asp
1               5                   10                  15 gtt gcc gag tat ctt ttc cgg cgt ctc cac gaa atc ggc att cgc tcc        96
Val Ala Glu Tyr Leu Phe Arg Arg Leu His Glu Ile Gly Ile Arg Ser
                20                  25                  30 atc cac ggt ctt cca ggc gat tac aac ctt ctt gcc ctc gac tat ttg       144
Ile His Gly Leu Pro Gly Asp Tyr Asn Leu Leu Ala Leu Asp Tyr Leu
            35                  40                  45 cca tca tgt ggc ctg aga tgg gtt ggc agc gtc aac gaa ctc aat gct       192
Pro Ser Cys Gly Leu Arg Trp Val Gly Ser Val Asn Glu Leu Asn Ala
        50                  55                  60 gct tat gct gct gat ggc tat gcc cgc gtc aag cag atg gga gct ctc       240
Ala Tyr Ala Ala Asp Gly Tyr Ala Arg Val Lys Gln Met Gly Ala Leu
65                  70                  75                  80 atc acc act ttt gga gtg gga gag ctc tca gcc atc aat ggc gtt gcc       288
Ile Thr Thr Phe Gly Val Gly Glu Leu Ser Ala Ile Asn Gly Val Ala
                85                  90                  95 ggt gcc ttt tcg gaa cac gtc cca gtc gtt cac att gtt ggc tgc cct       336
Gly Ala Phe Ser Glu His Val Pro Val Val His Ile Val Gly Cys Pro
            100                 105                 110 tcc act gcc tcg cag cga aac ggc atg ctc ctc cac cac acg ctt gga       384
Ser Thr Ala Ser Gln Arg Asn Gly Met Leu Leu His His Thr Leu Gly
        115                 120                 125 aac ggc gac ttc aac atc ttt gcc aac atg agc gct caa atc tct tgc       432
Asn Gly Asp Phe Asn Ile Phe Ala Asn Met Ser Ala Gln Ile Ser Cys
130                 135                 140 gaa gtg gcc aag ctc acc aac cct gcc gaa att gcg acc cag atc gac       480
Glu Val Ala Lys Leu Thr Asn Pro Ala Glu Ile Ala Thr Gln Ile Asp
145                 150                 155                 160 cat gcc ctc cgc gtt tgc ttc att cgt tct cgg ccc gtc tac atc atg       528
His Ala Leu Arg Val Cys Phe Ile Arg Ser Arg Pro Val Tyr Ile Met
                165                 170                 175 ctt ccc acc gat atg gtc cag gcc aaa gta gaa ggt gcc aga ctc aag       576
Leu Pro Thr Asp Met Val Gln Ala Lys Val Glu Gly Ala Arg Leu Lys
            180                 185                 190 gaa cca att gac ttg tcg gag cct cca aat gat ccc gag aaa gaa gca       624
Glu Pro Ile Asp Leu Ser Glu Pro Pro Asn Asp Pro Glu Lys Glu Ala
        195                 200                 205 tac gtc gtt gac gtt gtc ctc aag tac ctc cgt gct gca aag aac ccc       672
Tyr Val Val Asp Val Val Leu Lys Tyr Leu Arg Ala Ala Lys Asn Pro
210                 215                 220 gtc atc ctt gtc gat gct tgt gct atc cgt cat cgt gtt ctt gat gag       720
Val Ile Leu Val Asp Ala Cys Ala Ile Arg His Arg Val Leu Asp Glu
225                 230                 235                 240 gtt cat gat ctc atc gaa aag aca aac ctc ccc gtc ttt gtc act cct       768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc       816
Met Gly Lys Gly Ala Val Asn Glu Glu His Pro Thr Tyr Gly Gly Val
            260                 265                 270 tat gcc ggt gac ggc tca cat ccg cct caa gtt aag gac atg gtt gag       864
Tyr Ala Gly Asp Gly Ser His Pro Pro Gln Val Lys Asp Met Val Glu
        275                 280                 285 tct tct gat ttg ata ttg aca atc ggt gct ctc aag agc gac ttc aac       912
Ser Ser Asp Leu Ile Leu Thr Ile Gly Ala Leu Lys Ser Asp Phe Asn
290                 295                 300 act gct ggc ttc tct tac cgt acc tca cag ctg aac acg att gat cta       960
Thr Ala Gly Phe Ser Tyr Arg Thr Ser Gln Leu Asn Thr Ile Asp Leu
305                 310                 315                 320
```

| | | | | | | | | | | | | | | | |
|---|---|---|---|---|---|---|---|---|---|---|---|---|---|---|---|
| cac | agc | gac | cac | tgc | att | gtc | aaa | tac | tcg | aca | tat | cca | ggt | gtc | cag | 1008
| His | Ser | Asp | His | Cys | Ile | Val | Lys | Tyr | Ser | Thr | Tyr | Pro | Gly | Val | Gln |
| | | | 325 | | | | | 330 | | | | | | 335 | |

| | | | | | | | | | | | | | | | |
|---|---|---|---|---|---|---|---|---|---|---|---|---|---|---|---|
| atg | agg | ggt | gtg | ctg | cga | caa | gtg | att | aag | cag | ctc | gat | gca | tct | gag | 1056
| Met | Arg | Gly | Val | Leu | Arg | Gln | Val | Ile | Lys | Gln | Leu | Asp | Ala | Ser | Glu |
| | | | 340 | | | | | 345 | | | | | 350 | | |

| | | | | | | | | | | | | | | | |
|---|---|---|---|---|---|---|---|---|---|---|---|---|---|---|---|
| atc | aac | gct | cag | cca | gcg | cca | gtc | gtc | gag | aat | gaa | gtt | gcc | aaa | aac | 1104
| Ile | Asn | Ala | Gln | Pro | Ala | Pro | Val | Val | Glu | Asn | Glu | Val | Ala | Lys | Asn |
| | | | 355 | | | | | 360 | | | | | 365 | | |

| | | | | | | | | | | | | | | | |
|---|---|---|---|---|---|---|---|---|---|---|---|---|---|---|---|
| cga | gat | aac | tca | ccc | gtc | att | aca | caa | gct | ttc | ttc | tgg | ccg | cgc | gtg | 1152
| Arg | Asp | Asn | Ser | Pro | Val | Ile | Thr | Gln | Ala | Phe | Phe | Trp | Pro | Arg | Val |
| | | 370 | | | | | 375 | | | | | 380 | | | |

| | | | | | | | | | | | | | | | |
|---|---|---|---|---|---|---|---|---|---|---|---|---|---|---|---|
| gga | gag | ttc | ctg | aag | aag | aac | gac | atc | gtc | att | acc | gag | act | gga | aca | 1200
| Gly | Glu | Phe | Leu | Lys | Lys | Asn | Asp | Ile | Val | Ile | Thr | Glu | Thr | Gly | Thr |
| 385 | | | | | 390 | | | | | 395 | | | | | 400 |

| | | | | | | | | | | | | | | | |
|---|---|---|---|---|---|---|---|---|---|---|---|---|---|---|---|
| gcc | aac | ttt | ggc | atc | tgg | gat | act | aag | ttt | ccc | tct | ggc | gtt | act | gcg | 1248
| Ala | Asn | Phe | Gly | Ile | Trp | Asp | Thr | Lys | Phe | Pro | Ser | Gly | Val | Thr | Ala |
| | | | | 405 | | | | | 410 | | | | | 415 | |

| | | | | | | | | | | | | | | | |
|---|---|---|---|---|---|---|---|---|---|---|---|---|---|---|---|
| ctt | tct | cag | gtc | ctt | tgg | gga | agc | att | ggt | tgg | tcc | gtt | ggt | gcc | tgc | 1296
| Leu | Ser | Gln | Val | Leu | Trp | Gly | Ser | Ile | Gly | Trp | Ser | Val | Gly | Ala | Cys |
| | | | 420 | | | | | 425 | | | | | 430 | | |

| | | | | | | | | | | | | | | | |
|---|---|---|---|---|---|---|---|---|---|---|---|---|---|---|---|
| caa | gga | gcc | gtt | ctt | gca | gcc | gcc | gat | gac | aac | agc | gat | cgc | aga | act | 1344
| Gln | Gly | Ala | Val | Leu | Ala | Ala | Ala | Asp | Asp | Asn | Ser | Asp | Arg | Arg | Thr |
| | | | 435 | | | | | 440 | | | | | 445 | | |

| | | | | | | | | | | | | | | | |
|---|---|---|---|---|---|---|---|---|---|---|---|---|---|---|---|
| atc | ctc | ttt | gtt | ggt | gat | ggc | tca | ttc | cag | ctc | act | gct | caa | gaa | ttg | 1392
| Ile | Leu | Phe | Val | Gly | Asp | Gly | Ser | Phe | Gln | Leu | Thr | Ala | Gln | Glu | Leu |
| | | | 450 | | | | | 455 | | | | | 460 | | |

| | | | | | | | | | | | | | | | |
|---|---|---|---|---|---|---|---|---|---|---|---|---|---|---|---|
| agc | aca | atg | att | cgt | ctc | aag | ctg | aag | ccc | atc | atc | ttt | gtc | atc | tgc | 1440
| Ser | Thr | Met | Ile | Arg | Leu | Lys | Leu | Lys | Pro | Ile | Ile | Phe | Val | Ile | Cys |
| 465 | | | | | 470 | | | | | 475 | | | | | 480 |

| | | | | | | | | | | | | | | | |
|---|---|---|---|---|---|---|---|---|---|---|---|---|---|---|---|
| aac | gat | ggc | ttt | acc | att | gaa | cga | ttc | att | cac | ggc | atg | gaa | gcc | gag | 1488
| Asn | Asp | Gly | Phe | Thr | Ile | Glu | Arg | Phe | Ile | His | Gly | Met | Glu | Ala | Glu |
| | | | | 485 | | | | | 490 | | | | | 495 | |

| | | | | | | | | | | | | | | | |
|---|---|---|---|---|---|---|---|---|---|---|---|---|---|---|---|
| tac | aac | gac | atc | gca | aat | tgg | gac | ttc | aag | gct | ctg | gtt | gac | gtc | ttt | 1536
| Tyr | Asn | Asp | Ile | Ala | Asn | Trp | Asp | Phe | Lys | Ala | Leu | Val | Asp | Val | Phe |
| | | | 500 | | | | | 505 | | | | | 510 | | |

| | | | | | | | | | | | | | | | |
|---|---|---|---|---|---|---|---|---|---|---|---|---|---|---|---|
| ggc | ggc | tct | aag | acg | gcc | aag | aag | ttc | gcc | gtc | aag | acc | aag | gac | gag | 1584
| Gly | Gly | Ser | Lys | Thr | Ala | Lys | Lys | Phe | Ala | Val | Lys | Thr | Lys | Asp | Glu |
| | | | 515 | | | | | 520 | | | | | 525 | | |

| | | | | | | | | | | | | | | | |
|---|---|---|---|---|---|---|---|---|---|---|---|---|---|---|---|
| ctg | gac | agc | ctt | ctc | aca | gac | cct | acc | ttt | aac | gcc | gca | gaa | tgc | ctc | 1632
| Leu | Asp | Ser | Leu | Leu | Thr | Asp | Pro | Thr | Phe | Asn | Ala | Ala | Glu | Cys | Leu |
| | | 530 | | | | | 535 | | | | | 540 | | | |

| | | | | | | | | | | | | | | | |
|---|---|---|---|---|---|---|---|---|---|---|---|---|---|---|---|
| cag | ttt | gtc | gag | cta | tat | atg | ccc | aaa | gaa | gat | gct | cct | cga | gca | ttg | 1680
| Gln | Phe | Val | Glu | Leu | Tyr | Met | Pro | Lys | Glu | Asp | Ala | Pro | Arg | Ala | Leu |
| 545 | | | | | 550 | | | | | 555 | | | | | 560 |

| | | | | | | | | | | | | | | | |
|---|---|---|---|---|---|---|---|---|---|---|---|---|---|---|---|
| atc | atg | acg | gca | gaa | gct | agc | gcg | agg | aac | aat | gcc | aag | aca | gag | taa | 1728
| Ile | Met | Thr | Ala | Glu | Ala | Ser | Ala | Arg | Asn | Asn | Ala | Lys | Thr | Glu | * |
| | | | | 565 | | | | | 570 | | | | | 575 | |

<210> SEQ ID NO 24
<211> LENGTH: 575
<212> TYPE: PRT
<213> ORGANISM: Unknown
<220> FEATURE:
<223> OTHER INFORMATION: Fungal isolate from soil sample

<400> SEQUENCE: 24

Met Ala Ser Ile Asn Ile Arg Val Gln Asn Leu Glu Gln Pro Met Asp
 1               5                   10                  15

Val Ala Glu Tyr Leu Phe Arg Arg Leu His Glu Ile Gly Ile Arg Ser
            20                  25                  30

```
Ile His Gly Leu Pro Gly Asp Tyr Asn Leu Leu Ala Leu Asp Tyr Leu
         35                  40                  45

Pro Ser Cys Gly Leu Arg Trp Val Gly Ser Val Asn Glu Leu Asn Ala
 50                  55                  60

Ala Tyr Ala Ala Asp Gly Tyr Ala Arg Val Lys Gln Met Gly Ala Leu
 65                  70                  75                  80

Ile Thr Thr Phe Gly Val Gly Glu Leu Ser Ala Ile Asn Gly Val Ala
                 85                  90                  95

Gly Ala Phe Ser Glu His Val Pro Val His Ile Val Gly Cys Pro
                100                 105                 110

Ser Thr Ala Ser Gln Arg Asn Gly Met Leu Leu His Thr Leu Gly
        115                 120                 125

Asn Gly Asp Phe Asn Ile Phe Ala Asn Met Ser Ala Gln Ile Ser Cys
        130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
                165                 170                 175

Leu Pro Thr Asp Met Val Gln Ala Lys Val Glu Gly Ala Arg Leu Lys
                180                 185                 190

Glu Pro Ile Asp Leu Ser Glu Pro Asn Asp Pro Glu Lys Glu Ala
        195                 200                 205

Tyr Val Val Asp Val Val Leu Lys Tyr Leu Arg Ala Ala Lys Asn Pro
        210                 215                 220

Val Ile Leu Val Asp Ala Cys Ala Ile Arg His Arg Val Leu Asp Glu
225                 230                 235                 240

Val His Asp Leu Ile Glu Lys Thr Asn Leu Pro Val Phe Val Thr Pro
                245                 250                 255

Met Gly Lys Gly Ala Val Asn Glu Glu His Pro Thr Tyr Gly Gly Val
        260                 265                 270

Tyr Ala Gly Asp Gly Ser His Pro Pro Gln Val Lys Asp Met Val Glu
        275                 280                 285

Ser Ser Asp Leu Ile Leu Thr Ile Gly Ala Leu Lys Ser Asp Phe Asn
290                 295                 300

Thr Ala Gly Phe Ser Tyr Arg Thr Ser Gln Leu Asn Thr Ile Asp Leu
305                 310                 315                 320

His Ser Asp His Cys Ile Val Lys Tyr Ser Thr Tyr Pro Gly Val Gln
                325                 330                 335

Met Arg Gly Val Leu Arg Gln Val Ile Lys Gln Leu Asp Ala Ser Glu
        340                 345                 350

Ile Asn Ala Gln Pro Ala Pro Val Glu Asn Glu Val Ala Lys Asn
        355                 360                 365

Arg Asp Asn Ser Pro Val Ile Thr Gln Ala Phe Phe Trp Pro Arg Val
        370                 375                 380

Gly Glu Phe Leu Lys Lys Asn Asp Ile Val Ile Thr Glu Thr Gly Thr
385                 390                 395                 400

Ala Asn Phe Gly Ile Trp Asp Thr Lys Phe Pro Ser Gly Val Thr Ala
                405                 410                 415

Leu Ser Gln Val Leu Trp Gly Ser Ile Gly Trp Ser Val Gly Ala Cys
        420                 425                 430

Gln Gly Ala Val Leu Ala Ala Ala Asp Asp Asn Ser Asp Arg Arg Thr
        435                 440                 445
```

-continued

```
Ile Leu Phe Val Gly Asp Gly Ser Phe Gln Leu Thr Ala Gln Glu Leu
        450                 455                 460

Ser Thr Met Ile Arg Leu Lys Leu Lys Pro Ile Ile Phe Val Ile Cys
465                 470                 475                 480

Asn Asp Gly Phe Thr Ile Glu Arg Phe Ile His Gly Met Glu Ala Glu
                485                 490                 495

Tyr Asn Asp Ile Ala Asn Trp Asp Phe Lys Ala Leu Val Asp Val Phe
                500                 505                 510

Gly Gly Ser Lys Thr Ala Lys Lys Phe Ala Val Lys Thr Lys Asp Glu
            515                 520                 525

Leu Asp Ser Leu Leu Thr Asp Pro Thr Phe Asn Ala Ala Glu Cys Leu
        530                 535                 540

Gln Phe Val Glu Leu Tyr Met Pro Lys Glu Asp Ala Pro Arg Ala Leu
545                 550                 555                 560

Ile Met Thr Ala Glu Ala Ser Ala Arg Asn Asn Ala Lys Thr Glu
                565                 570                 575
```

METHODS TO CONFER HERBICIDE RESISTANCE

CROSS-REFERENCE TO RELATED APPLICATIONS

This application is a continuation-in-part of U.S. application Ser. No. 10/797,270, filed Mar. 10, 2004 now abandoned, which claims the benefit of U.S. Provisional Application Ser. No. 60/453, 148, filed Mar. 10, 2003, the contents of which are herein incorporated by reference in their entirety.

FIELD OF THE INVENTION

Methods to confer herbicide resistance to cells, particularly glyphosate resistance, are provided. These methods are especially useful with plant and bacterial cells.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases may have a high tolerance to glyphosate.

Plant cells resistant to glyphosate toxicity can be produced by transforming plant cells to express glyphosate-resistant EPSP synthases. A mutated EPSP synthase from *Salmonella typhimurium* strain CT7 confers glyphosate resistance in bacterial cells, and confers glyphosate resistance on plant cells (U.S. Pat. Nos. 4,535,060, 4,769,061, and 5,094,945). Thus, there is a precedent for the use of glyphosate-resistant bacterial EPSP synthases to confer glyphosate resistance upon plant cells.

An alternative method to generate target genes resistant to a toxin (such as an herbicide) is to identify and develop enzymes that result in detoxification of the toxin to an inactive or less active form. This can be accomplished by identifying enzymes that encode resistance to the toxin in a toxin-sensitive test organism, such as a bacterium.

Castle et al. (WO 02/36782 A2) describe proteins (glyphosate N-acetyltransferases) that are described as modifying glyphosate by acetylation of a secondary amine to yield N-acetylglyphosate.

Barry et al. (U.S. Pat. No. 5,463,175) describes genes encoding an oxidoreductase (GOX), and states that GOX proteins degrade glyphosate by removing the phosphonate residue to yield amino methyl phosphonic acid (AMPA). This suggests that glyphosate resistance can also be conferred, at least partially, by removal of the phosphonate group from glyphosate. However, the resulting compound (AMPA) appears to provide reduced but measurable toxicity upon plant cells. Barry describes the effect of AMPA accumulation on plant cells as resulting in effects including chlorosis of leaves, infertility, stunted growth, and death. Barry (U.S. Pat. No. 6,448,476) describes plant cells expressing an AMPA-N-acetyltransferase (phnO) to detoxify AMPA.

Phosphonates, such as glyphosate, can also be degraded by cleavage of C—P bond by a C—P lyase. Wacket et al. (1987) *J. Bacteriol.* 169:710-717) described strains that utilize glyphosate as a sole phosphate source. Kishore et al. (1987) *J. Biol. Chem.* 262:12164-12168 and Shinabarger et al. (1986) *J. Bacteriol.* 168:702-707 describe degradation of glyphosate by C—P Lyase to yield glycine and inorganic phosphate.

While several strategies are available for detoxification of toxins, such as the herbicide glyphosate, as described above, new activities capable of degrading glyphosate are useful. Novel genes and genes conferring glyphosate resistance by novel mechanisms of action would be of additional usefulness. Single genes conferring glyphosate resistance by formation of non-toxic products would be especially useful.

Further, genes conferring resistance to other herbicides, such as the sulfonylureas or imidazolinones, are useful. The sulfonylurea and imidazolinine herbicides are widely used in agriculture because of their efficacy at low use rates against a broad spectrum of weeds, lack of toxicity to mammals, and favorable environmental profile (Saari et al. (1994) p. 83-139 in: *Herbicide Resistance in Plants: Biology and Biochemistry*. S. Powles and J. Holtum eds. Lewis Publishers, Inc., Boca Raton, Fla.). These herbicides act by inhibiting acetohydroxyacid synthase (AHAS, also known as acetolactate synthase) and thereby preventing the biosynthesis of the branched-chain amino acids valine, leucine and isoleucine.

Current methods of herbicide tolerance confer upon a plant tolerance to herbicides with a particular target or mode of action. However, repeated and extensive use of herbicides with a single mode of action can result in the selection of tolerant weed species (Saari et al., supra). Crop plants which are resistant to more than one class of herbicides (with different modes of action) provide growers with flexibility in weed control options and are useful in preventing/managing the emergence of resistant weed populations. Plants containing a single trait that conferred tolerance to more than one class of herbicide would be particularly desirable. Thus, genes encoding resistance to more than one class of herbicide are useful.

Thus, methods that result in degradation of herbicides to non-toxic forms are desired. Further, methods that achieve sufficient degradation to allow cells to grow in otherwise toxic concentrations of herbicide ("herbicide resistance") are desired. Methods that confer "herbicide resistance" through the expression of a single protein would be preferred, since expression of a single protein in a cell such as a plant cell is technically less complex than the expression of multiple proteins. Further, in some instances, methods for conferring herbicide resistance that are compatible with, and/or improve the efficacy of other methods of conferring herbicide resistance, are desirable.

SUMMARY OF INVENTION

Compositions and methods for conferring herbicide resistance to bacteria, plants, plant cells, tissues and seeds are provided. In particular, herbicide resistance is conferred by expression of proteins with homology to decarboxylase enzymes. In one embodiment, the herbicide is a glyphosate herbicide. In addition, the expressed protein may result in increased tolerance of the cell to more than one herbicide. Compositions comprise transformed bacteria, plants, plant cells, tissues, and seeds.

Decarboxylase enzymes that could be useful in conferring herbicide resistance include, but are not limited to, a pyruvate decarboxylase, a benzoylformate decarboxylase, an oxalyl-CoA decarboxylase, a 2-oxoglutarate decarboxylase, an indolepyruvate decarboxylase, a 5-guanidino-2-oxopentanoate decarboxylase, a phenylglyoxylate dehydrogenase (acylating), a pyruvate dehydrogenase (cytochrome), a pyruvate oxidase, a pyruvate dehydrogenase (lipoamide), an oxoglutarate dehydrogenase (lipoamide), a transketolase, a formaldehyde transketolase, an acetoin-ribose-5-phosphate transaldolase, a tartronate-semialdehyde synthase, a phosphoketolase, a fructose-6-phosphate phosphoketolase, a benzoin aldolase, a 2-hydroxy-3-oxoadipate synthase, an acetolactate synthase, an 1-deoxy-C-xylulose 5-phosphate synthase, and a sulfoacetaldehyde lyase.

DESCRIPTION OF FIGURES

FIGS. 1A-1D show an alignment of GDC-1 (SEQ ID NO:22) and GDC-2 (SEQ ID NO:15) to pyruvate decarboxylase of *Saccharomyces cerevesiae* (SEQ ID NO:16), a putative indole-3-pyruvate decarboxylase from *Salmonella typhimurium* (SEQ ID NO:17), pyruvate decarboxylase (EC 4.1.1.1) from *Zymomonas mobilis* (SEQ ID NO:18), acetolactate synthase from *Saccharomyces cerevesiae* (SEQ ID NO:19), and acetolactate synthase from *Magnaporthe grisea* (SEQ ID NO:20). The alignment shows the most highly conserved amino acid residues highlighted in black, and highly conserved amino acid residues highlighted in gray.

FIG. 2A shows growth of GDC-1 expressing cells at various concentrations of glyphosate as compared to vector and media only controls at 42 hours. FIG. 2B shows growth of GDC-2 expressing cells at various concentrations of glyphosate as compared to vector and media only controls at 42 hours. Growth was measured by absorbance at 600 nm.

DETAILED DESCRIPTION

The present invention is drawn to compositions and methods for conferring resistance to an herbicide in a cell, particularly in a plant cell or a bacterial cell. The methods involve transforming the cell with a nucleotide sequence encoding an herbicide resistance gene. In particular, the methods of the invention are useful for preparing plant and bacterial cells that show increased tolerance to the herbicide glyphosate. Thus, compositions include transformed plants, plant cells, plant tissues and seeds as well as transformed bacterial cells.

Definitions

"Glyphosate" includes any herbicidal form of N-phosphonomethylglycine (including any salt thereof) and other forms that result in the production of the glyphosate anion in planta.

"Glyphosate (or herbicide) resistance-conferring decarboxylase" or "GDC" includes a DNA segment that encodes all or part of a glyphosate (or herbicide) resistance protein. This includes DNA segments that are capable of expressing a protein that confers glyphosate (herbicide) resistance to a cell.

An "herbicide resistance protein" or an "herbicide resistance protein molecule" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein.

A "glyphosate resistance protein", includes a protein that confers upon a cell the ability to tolerate a higher concentration of glyphosate than cells that do not express the protein, or to tolerate a certain concentration of glyphosate for a longer time than cells that do not express the protein. By "tolerate" or "tolerance" is intended either to survive, or to carry out essential cellular functions such as protein synthesis and respiration in a manner that is not readily discernable from untreated cells.

By "decarboxylase" is intended a protein, or gene encoding a protein, whose catalytic mechanism can include cleavage and release of a carboxylic acid. This includes enzymes that liberate $CO_2$, such as pyruvate decarboxlyases, acetolactate synthases, and orthinine decarboxylases, as well as enzymes that liberate larger carboxylic acids, as illustrated in Table 1. "Decarboxylase" includes proteins that utilize thiamine pyrophoshate as a cofactor in enzymatic catalysis. Many such decarbolyases also utilize other cofactors, such as FAD.

By "TPP-binding domain" is intended a region of conserved amino acids present in enzymes that are capable of utilizing TPP as a cofactor.

"Plant tissue" includes all known forms of plants, including undifferentiated tissue (e.g. callus), suspension culture cells, protoplasts, plant cells including leaf cells, root cells, and phloem cells, plant seeds, pollen, propagules, embryos and the like.

"Plant expression cassette" includes DNA constructs that are capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

"Signal sequence" includes sequences that are known or suspected to result in co-translational or post-translational peptide transport across the cell membrane. In eukaryotes, this typically involves secretion into the Golgi apparatus, with some resulting glycosylation.

"Leader sequence" includes any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

"Plant transformation vector" includes DNA molecules that are necessary for efficient transformation of a plant cell. Such a molecule may consist of one or more plant expression cassettes, and may be organized into more than one 'vector' DNA molecules. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451).

"Vector" refers to a nucleic acid construct designed for transfer between different host cells. "Expression vector" refers to a vector that has ability to incorporate, integrate and express heterologous DNA sequences or fragments in a foreign cell.

"Transgenic plants" or "transformed plants" or "stably transformed plants or cells or tissues" refers to plants that have incorporated or integrated exogenous or endogenous nucleic acid sequences or DNA fragments or chimeric nucleic acid sequences or fragments.

"Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences (also termed as "control sequences") are necessary for the expression of a DNA sequence of interest.

Various aspects of the invention are described in further detail in the following subsections.

Decarboxylases

Decarboxylation is a general class of chemical reactions, generally defined as a reaction that results in cleavage of a carbon-carbon bond, resulting in the liberation of a new carbon, often in the form of carbon dioxide ($CO_2$). A thorough description of the biochemical mechanism of decarboxylation is provided in the following references, herein incorporated by reference (Jorday (1999) *FEBS letters* 457:298-301; Pohl (1997) *Adv. Biochem. Eng. Biotechnol* 58:15-43).

Decarboxylases are also capable of performing condensation reactions (reactions that combine two compounds). Typically such reactions are known in the art as carboligation reactions, and typically result in production of hydroxy ketones. Decarboxylases in general, including pyruvate decarboxylases and acetolactate synthases, are known to be able to perform carboligation reactions on a wide variety of substrates (for review, see Ward and Singh (2000) *Current Opinions in Biotechnology* 11:520-526, and Ohta and Sugai (2000) "Enzyme-mediated Decarboxylation Reactions in organic synthesis" in *Stereoselective Biocatalysis*, Patel, R. N., ed, Marcel Deckker, Inc., references therein).

Many decarboxylation enzymes utilize the cofactor thiamine pyrophosphate (referred to herein as "TPP"). TPP facilitates many enzyme reactions, typically those involving transfer of aldehyde groups from a donor molecule to an acceptor molecule. A well-known example of a decarboxylation reaction involving TPP as a cofactor is the conversion of pyruvate to acetaldehyde and $CO_2$ by the enzyme pyruvate decarboxylase. Acetolactate synthases are another example of a class of decarboxylating enzymes that utilize TPP as a cofactor. Examples of other reactions that utilize TPP as a cofactor include dehydrogenations, such as the reaction catalyzed by pyruvate dehydrogenase, and α-ketoglutarate dehydrogenase.

Thus, the coenzyme TPP is a valuable cofactor, important for catalytic processes. Analysis of amino acid sequences of known TPP-utilizing enzymes has allowed the identification of amino acid regions common to each class of TPP-utilizing proteins. Enzymes that are capable of utilizing TPP as a cofactor share several regions of amino acid conservation, referred to herein as "TPP-binding domains". These regions are often referred to as the N-terminal domain, central domain, and C-terminal domain, in reference to their position within the amino acid sequence (see for example, Hawkins et al. (1989) *FEBS Letters* 255:77-82; Arjunan et al. (1996) *J. Mol. Biol.* 256:590-600; Barilan et al. (2001) *Biochemistry* 40:11946-11954). Thus, pyruvate decarboxylase, pyruvate dehydrogenase, α-ketoglutarate dehydrogenase, and acetolactate synthase each contain TPP-binding domains. Further, the amino acid conservation shared by TPP-binding proteins can be identified by comparison of the amino acid sequence of a new protein with the amino acid sequence of known TPP-binding proteins.

Aside from the presence of conserved domains, decarboxylase enzymes can also share significant amino acid homology in regions of their amino acid sequence other than the conserved domains. Thus, a high degree of amino acid conservation is suggestive of similar functional role.

Co-pending U.S. Application entitled "GDC-1 Genes Conferring Herbicide Resistance", filed concurrently herewith, and incorporated herein by reference, describes the identification of a gene sequence referred to therein as GDC-1. The sequence of GDC-1 encodes an herbicide resistance protein, conferring resistance to the herbicide glyphosate. Co-pending U.S. Application entitled "GDC-2 Genes Conferring Herbicide Resistance", filed concurrently herewith, and incorporated herein by reference, describes the identification of a gene sequence referred to therein as GDC-2. The sequence of GDC-2 encodes an herbicide resistance protein, conferring resistance to the herbicide glyphosate. GDC-1 and GDC-2 contain TPP-binding domains. While not being bound by any particular mechanism of action, the homology of the protein sequences of GDC-1 and GDC-2 herbicide tolerance-conferring genes to TPP-binding decarboxylases, as well as biochemical data provided herein, suggests that GDC-1 and/or GDC-2 encode herbicide tolerance by reactions involving the cofactor TPP.

Thus, by identifying genes encoding proteins with a high homology to known decarboxylases, one is likely to identify previously unknown decarboxylases. Many of these decarboxylases may be capable of functioning to detoxify herbicides such as glyphosate.

Having provided that proteins containing TPP-binding domains are capable of conferring resistance to glyphosate, it is understood that one skilled in the art could measure the decarboxylation activity of any of these proteins, for example by incubating a purified, semi-purified, or crude extract containing the glyphosate tolerance-conferring protein with glyphosate, and assaying for the products of glyphosate degradation. Examples of methods to measure such activity in both GDC-1 and GDC-2 are provided in the Example section.

Herbicide Resistance Proteins

Preferred herbicide resistance proteins for use in the methods of the present invention are decarboxylase enzymes. Examples of decarboxylase enzymes that may be used are provided in Table 1. In one embodiment the GDC-1 coding sequence, as disclosed in co-pending U.S. Application entitled "GDC-1 Genes Conferring Herbicide Resistance", filed concurrently herewith, is the herbicide resistance protein. In another embodiment, the GDC-2 coding sequence, as disclosed in co-pending U.S. Application entitled "GDC-2 Genes Conferring Herbicide Resistance", filed concurrently herewith, is the herbicide resistance protein.

Methods of the invention also encompass variant nucleic acid molecules that are sufficiently identical to the sequences provided for representative decarboxylase enzymes. "Variants" of the herbicide resistance-encoding nucleotide sequences include those sequences that encode the decarboxylase proteins disclosed herein but that differ conservatively because of the degeneracy of the genetic code, as well as those that are sufficiently identical as described below. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the decarboxylase proteins disclosed in the present invention as discussed below. Variant proteins for use in the methods of the present invention are biologically active, that is they retain the desired biological activity of the native protein, that is, herbicide resistance activity. By "retains herbicide resistance activity" is intended that the variant will have at least about 30%, preferably at least about 50%, more preferably at least about 70%, even more preferably at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The term "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to herbicide resistance-encoding nucleic acid molecules used in methods of the invention. BLAST protein searches can be performed with the BLASTX program, score=50, wordlength=3, to obtain amino acid sequences homologous to herbicide resistance protein molecules expressed using the methods of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994). *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identify between multiple proteins. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) supra. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The skilled artisan will further appreciate that changes can be introduced by mutation into the nucleotide sequences used in the methods of the invention, thereby leading to changes in the amino acid sequence of the encoded herbicide resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Methods using such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer herbicide resistance activity to identify mutants that retain activity. Following mutagenesis, the encoded protein can be expressed recombinantly, and the activity of the protein can be determined using standard assay techniques.

The methods of the invention also encompass nucleic acid molecules comprising nucleotide sequences encoding partial-length herbicide resistance proteins. Nucleic acid molecules that are fragments of the herbicide resistance-encoding nucleotide sequences are also encompassed by the present invention. By "fragment" is intended a portion of the nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600 nucleotides, or up to the number of nucleotides present in a full-length herbicide resistance-encoding nucleotide sequence (for example, 2210 nucleotides for SEQ ID NO:1) depending upon the intended use. Fragments of the nucleotide sequences will encode protein fragments that retain the biological activity of the native herbicide resistance protein. By "retains herbicide resistance activity" is intended that the fragment will have at least about 30%, preferably at least about 50%, more preferably at least about 70%, even more preferably at least about 80% of the herbicide resistance activity of the native herbicide resistance protein. Methods for measuring herbicide resistance activity are well known in the art. See, for example, U.S. Pat. Nos. 4,535,060, and 5,188,642, each of which are herein incorporated by reference in their entirety.

A fragment of an herbicide resistance encoding nucleotide sequence that encodes a biologically active portion of a protein of the invention will encode at least about 15, 25, 30, 50, 75, 100, 125, 150, 175, 200, 250, 300, 350, 400, 450, 500, or 550 contiguous amino acids, or up to the total number of amino acids present in a full-length herbicide resistance protein for use with methods of the invention (for example, 575 amino acids for SEQ ID NO: 3).

Altered or Improved Variants

It is recognized that DNA sequence of an herbicide resistance gene may be altered by various methods, and that these alterations may result in DNA sequences encoding proteins with amino acid sequences different that that encoded by an herbicide resistance gene. This protein may be altered in various ways including amino acid substitutions, deletions, truncations, and insertions. Methods for such manipulations are generally known in the art. For example, amino acid sequence variants of the herbicide resistance protein can be prepared by mutations in the DNA. This may also be accomplished by one of several forms of mutagenesis and/or in directed evolution. In some aspects, the changes encoded in the amino acid sequence will not substantially affecting function of the protein. Such variants will possess the desired herbicide resistance activity. However, it is understood that the ability of an herbicide resistance gene to confer herbicide resistance may be improved by one use of such techniques upon the compositions of this invention. For example, one may express an herbicide resistance gene in host cells that exhibit high rates of base misincorporation during DNA replication, such as XL-1 Red (Stratagene). After propagation in such strains, one can isolate the herbicide resistance DNA (for example by preparing plasmid DNA, or by amplifying by PCR and cloning the resulting PCR fragment into a vector), culture the herbicide resistance mutations in a non-mutagenic strain, and identify mutated herbicide resistance genes with improved resistance to herbicide, for example by growing cells in increasing concentrations of herbicide such as glyphosate, and testing for clones that confer an ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

TABLE 1

Listing of enzyme classes in Expasy database listing TPP as a cofactor

| EC Number | Enzyme Classification | Cofactors other than TPP (if any) | Exemplary GENBANK Accession No. |
|---|---|---|---|
| 1.2.1.58 | Phenylglyoxylate dehydrogenase (acylating) | FAD | AJ428571 |
| 1.2.2.2 | Pyruvate dehydrogenase (cytochrome) | | AAC73958 |

TABLE 1-continued

Listing of enzyme classes in Expasy
database listing TPP as a cofactor

| EC Number | Enzyme Classification | Cofactors other than TPP (if any) | Exemplary GENBANK Accession No. |
| --- | --- | --- | --- |
| 1.2.3.3 | Pyruvate oxidase | FAD | X04105 L39074 |
| 1.2.4.1 | Pyruvate dehydrogenase (lipoamide) | | U09865 |
| 1.2.4.2 | Oxoglutarate dehydrogenase (lipoamide) | | X91877 |
| 1.2.4.4 | 3-methyl-2-oxobutanoate dehydrogenase (lipoamide) | | M97391 |
| 2.2.1.1 | Transketolase | | Z73234 |
| 2.2.1.3 | Formaldehyde transketolase | | X02424 |
| 2.2.1.4 | Acetoin--ribose-5-phosphate transaldolase | | ND |
| 4.1.1.1 | Pyruvate decarboxylase | | U00967 |
| 4.1.1.7 | Benzoylformate decarboxylase | | J05293 |
| 4.1.1.8 | Oxalyl-CoA decarboxylase | | M77128 |
| 4.1.1.47 | Tartronate-semialdehyde synthase | | L03845 |
| 4.1.1.71 | 2-oxoglutarate decarboxylase | | M21787 |
| 4.1.1.74 | Indolepyruvate decarboxylase | Mg++ | L26240 D90214 |
| 4.1.1.75 | 5-guanidino-2-oxopentanoate decarboxylase | Divalent Cation | ND |
| 4.1.2.9 | Phosphoketolase | | AJ309011 |
| 4.1.2.22 | Fructose-6-phosphate phosphoketolase | | AJ293946 |
| 4.1.2.38 | Benzoin aldolase | | U04048 |
| 4.1.3.15 | 2-hydroxy-3-oxoadipate synthase | | ND |
| 4.1.3.18 | Acetolactate synthase | | L04470 |
| 4.1.3.37 | 1-deoxy-D-xylulose 5-phosphate synthase | | AF035440 |
| 4.4.1.12 | Sulfoacetaldehyde lyase | | AF305552 |

The sequences obtained through the Genbank accession numbers are herein incorporated by reference in their entirety.

Methods of Identifying/Isolating Herbicide Resistance Genes

Herbicide resistance genes may be identified by isolating DNA or cDNA from an organism, preferably an organism that is capable of growing in herbicidal or antibiotic concentrations of an herbicide. A library of clones (DNA or cDNA clones) can be transformed into a test organism, such as a bacterium. For example, *E. coli* may function as a test organism. The individual clones can be then grown on media containing the herbicide or antibiotic, at a concentration at which the test organism does not grow, or grows noticeably slower or to a noticeably lower density than cells grown in media lacking the herbicide. The clones conferring tolerance of the test cells to the herbicide ("positive clones") can then be identified. The DNA sequences of the positive clones are analyzed, and compared to databases of known proteins such as the Genbank 'nr' database. Finally, those positive clones with homology to known decarboxylases, or minimally having amino acid homology to a TPP-binding domain, can be identified.

Alternatively, sets of DNA sequences of genes or gene fragments may be screened, such as the Genbank database, or the Genbank EST database, and genes likely to encode decarboxylases or likely to have TPP-binding domains may be identified. Then, the genes could be cloned into a vector in such a way that the gene is expressed in a test cell, such as an *E. coli* cell. Finally, the cells expressing the genes could be tested at various concentrations of an herbicide, and those conferring resistance to an herbicide, such as glyphosate, could be identified.

A known sequence of a TPP-binding protein may be used to generate DNA probes. Then these DNA probes can be utilized to screen a library (libraries) composed of cloned DNA, or cloned cDNA from one or more organisms by methods known in the art for identifying homologous gene sequences. The homologous genes (if needed) can be engineered to be expressed in a test cell (such as an *E. coli* cell). Clones conferring increased tolerance to an herbicide may be identified and sequenced.

Alternatively, proteins having TPP-binding characteristics may be purified, for example, by covalently attaching TPP to a solid matrix, such as a bead, and adsorbing crude or partially purified protein extracts to the bead, washing the bead, and eluting the TPP-binding protein, for example by varying salt, pH, or other conditions that cause the TPP molecule to no longer bind the TPP-binding domain. The protein purified in this way can identify gene(s) likely to have herbicide resistance properties by obtaining a partial amino acid sequence of the protein, for example by performing amino-terminal amino acid sequencing. Upon knowing a sufficient portion of the amino acid sequence, the gene encoding this protein may be cloned by methods known in the art.

Genes containing such TPP-binding domains can also be identified directly, for example by phage display or cell surface display technologies. Phage display methods are based on expressing recombinant proteins or peptides fused to a phage coat protein. Such phage are then used to perform binding assays, and phage containing inserts conferring binding ability (such as by expression of a TPP-binding domain) are retained, and can be propagated using traditional phage bacteriology techniques. Bacterial display is a modification of phage display based on expressing recombinant proteins fused to sorting signals that direct their incorporation on the cell surface. Methods for phage display and bacterial display are well known in the art. For example, see Benhar (2001) *Biotechnol. Adv.* 19:1-33, or Hartley (2002) *J. Recept. Signal Transduct. Res.* 22:373-92, and references within.

In addition, having provided that TPP-binding proteins are capable of conferring herbicide resistance, and it being understood that many TPP-binding proteins are known to exist, and that additional TPP-binding enzymes may be identified by virtue of their amino acid homology, additional herbicide-resistance encoding proteins may be identified by testing one or all of the subset of known TPP-binding proteins by one or all of the assays described, in order to assess the herbicide resistance-conferring ability of the protein.

Alternatively, the DNA sequence of any of the known classes of TPP-binding proteins may be used to identify novel related proteins, which are also likely to bind TPP as a consequence of their catalytic role. Thus, having identified TPP-binding proteins by this way, the herbicide resistance conferring ability of such genes may be assessed.

Additionally, corresponding herbicide resistance sequences can be identified by using methods such as PCR, hybridization, and the like. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001. See also Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of herbicide resistance encoding nucleotide disclosed herein or a fragment or variant thereof. Preparation of probes for hybridization is generally known in the art and is disclosed in Sambrook and Russell, 2001, herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning. A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Transformation of Cells

Transformation of bacterial cells is accomplished by one of several techniques known in the art, not limited to electroporation, or chemical transformation (see for example Ausubel (ed.), Current Protocols in Molecular Biology, John Wiley and Sons, Inc. (1994)). Markers conferring resistance to toxic substances are useful in identifying transformed cells (having taken up and expressed the test DNA) from non-transformed cells (those not containing or not expressing the test DNA). By engineering the herbicide resistance gene to be (1) expressed from a bacterial promoter known to stimulate transcription in the organism to be tested, (2) properly translated to generate an intact herbicide resistance peptide, and (3) placing the cells in an otherwise toxic concentration of herbicide, one can identify cells that have been transformed with DNA by virtue of their resistance to herbicide.

Transformation of plant cells can be accomplished in similar fashion. First, one engineers the herbicide resistance gene in a way that allows its expression in plant cells. The organization of such constructs is well known in the art.

The herbicide resistance sequences used in the methods of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the herbicide resistance sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression. In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc. Many types of vectors can be used to transform plant cells for achieving herbicide resistance.

In general, plant transformation methods involve transferring heterologous DNA into target plant cells (e.g. immature or mature embryos, suspension cultures, undifferentiated callus, protoplasts, etc.), followed by applying a maximum threshold level of appropropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plantlets are found in Ayres and Park (1994) *Critical Reviews in Plant Science* 13:219-239, and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles including aerosol beam transformation (U.S. Published Application No. 20010026941; U.S. Pat. No. 4,945,050; International Publication No. WO 91/00915; U.S. Published Application No. 20020150066), and various other non-particle direct-mediated methods (e.g. Hiei et al. (1994) *The Plant Journal* 6: 271-282; Ishida et al. (1996) *Nature Biotechnology* 14: 745-750; Ayres and Park (1994) *Critical Reviews in Plant Science* 13: 219-239; Bommineni and Jauhar (1997) *Maydica* 42: 107-120) to transfer DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Following integration of heterologous foreign DNA into plant cells, one then applies a maximum threshold level of herbicide in the medium to kill the untransformed cells and separate and proliferate the putatively transformed cells that survive from this selection treatment by transferring regularly to a fresh medium. By continuous passage and challenge with herbicide, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001). PCR is carried out using oligonucleotide primers specific to the gene of interest or *Agrobacterium* vector background, etc.

Southern Analysis: Plant transformation is confirmed by Southern blot analysis of genomic DNA (Sambrook and Russell, 2001). In general, total DNA is extracted from the transformant, digested with appropriate restriction enzymes, fractionated in an agarose gel and transferred to a nitrocellulose or nylon membrane The membrane or "blot" then is probed with, for example, radiolabeled $^{32}$P target DNA fragment to confirm the integration of introduced gene in the plant genome according to standard techniques (Sambrook and Russell, 2001. *Molecular Cloning: A Laboratory Manual*. Cold Spring Harbor Laboratory Press, Cold Spring Harbor, N.Y.

Northern Analysis: RNA is isolated from specific tissues of transformant, fractionated in a formaldehyde agarose gel, blotted onto a nylon filter according to standard procedures that are routinely used in the art (Sambrook, J., and Russell, D. W. 2001. *Molecular Cloning: A Laboratory Manual*, Cold Spring Harbor Laboratory Press, Cold Spring Harbor, N.Y.) Expression of RNA encoded by the herbicide resistance gene is then tested by hybridizing the filter to a radioactive probe derived from an herbicide resistance gene, by methods known in the art (Sambrook and Russell, 2001)

Western blot and Biochemical assays: Western blot and biochemical assays and the like may be carried out on the transgenic plants to confirm the determine the presence of protein encoded by the herbicide resistance gene by standard procedures (Sambrook, J., and Russell, D. W. 2001. *Molecular Cloning: A Laboratory Manual*, Cold Spring Harbor Laboratory Press, Cold Spring Harbor, N.Y.) using antibodies that bind to one or more epitopes present on the herbicide resistance protein.

Herbicide Resistant Plants

In another aspect of the invention, one may generate transgenic plants expressing an herbicide resistance gene that are more resistant to high concentrations of herbicide than non-transformed plants. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing an herbicide resistance gene may be isolated by common methods described in the art, for example by transformation of callus, selection of transformed callus, and regeneration of fertile plants from such transgenic callus. In such process, an herbicide resistance gene may be used as selectable marker. Alternatively, one may use any gene as a selectable marker so long as its expression in plant cells confers ability to identify or select for transformed cells. Genes known to function effectively as selectable markers in plant transformation are well known in the art.

The following examples are offered by way of illustration and not by way of limitation.

EXPERIMENTAL

Example 1

GDC-1 and GDC-2 Confer Glyphosate Resistance Upon Cells

Starter cultures of *E. coli* containing GDC-1 (full), GDC-2, or vector alone were grown overnight in LB media, diluted 1:1000 into 3 ml M9 minimal media containing 0, 2, 5, 10, 20 and 30 mM glyphosate and grown at 37° C. Each strain was grown in triplicate at each concentration. $OD_{600}$ was measured at 0, 7, 24, and 28 hours after inoculation. Table 2 shows the $OD_{600}$ obtained for each construct at 28 hours after inoculation.

TABLE 2

| | Growth of clones in glyphosate | | | | | |
|---|---|---|---|---|---|---|
| Glyphosate | Vector | | GDC-1 | | GDC-2 | |
| concentration | Mean | S.D | Mean | S.D. | Mean | S.D. |
| 0 | 0.052 | 0.001 | 0.049 | 0.006 | 0.050 | 0.001 |
| 2 | 0.038 | 0.001 | 0.056 | 0.000 | 0.054 | 0.001 |
| 5 | 0.038 | 0.001 | 0.055 | 0.001 | 0.056 | 0.001 |
| 10 | 0.038 | 0.000 | 0.057 | 0.001 | 0.056 | 0.001 |
| 20 | 0.038 | 0.000 | 0.058 | 0.001 | 0.058 | 0.001 |

Example 2

GDC-1 and GDC-2 are Both TPP-Binding Decarboxylases

Searches of DNA and protein sequence databases, as well as sequence analysis of the GDC-1 and GDC-2 proteins show that they are homologous to pyruvate decarboxylase and acetolactate synthases. See, respectively, co-pending U.S. Application Publication No. 20060021093, entitled "GDC-1 Genes Conferring Herbicide Resistance", and co-pending U.S. Application entitled "GDC-2 Genes Conferring Herbicide Resistance", both filed Jul. 20, 2005 and are herein incorporated by reference in their entirety. These searches reveal that both both GDC-1 and GDC-2 contain amino acid regions which are conserved among TPP-binding proteins, including pyruvate decarboxylases and acetolactate synthases. An alignment of GDC-1 and GDC-2 with other known TPP-binding proteins is shown in FIG. 1.

Example 3

Engineering GDC-1 and GDC-2 for Expression in *E. coli*

*E. coli* strains expressing GDC-1 and GDC-2 were engineered into a customized expression vector, pAX481. pAX481 contains the pBR322 origin of replication, a chloramphenicol acetyl transferase gene (for selection and maintenance of the plasmid), the lacI gene, the Ptac promoter and the rrnB transcriptional terminator. The GDC-1 and GDC-2 open reading frames were amplified by PCR, using a high fidelity DNA polymerase, as known in the art. The oligonucleotides for PCR amplification of GDC-1 and GDC-2 were designed to place the ATG start site of the genes at the proper distance from the ribosome binding site of pAX481.

The GDC-1 PCR products were cloned into the expression vector pAX481 and transformed into *E. coli* XL1 Blue MRF' to yield the plasmid pAX472. The GDC-2 PCR product was cloned into the expression vector pAX481 and transformed into *E. coli* XL1 Blue MRF' to yield the plasmid pAX473. Postive clones were identified by standard methods known in the art. The sequences of pAX472 and pAX473 were confirmed by DNA sequence analysis as known in the art.

Example 4

GDC-1 and GDC-2 Do Not Complement an aroA Mutation in *E. coli*

The *E. coli* aroA gene codes for EPSP synthase, the target enzyme for glyphosate. EPSP synthase catalyzes the sixth step in the biosynthesis of aromatic amino acids in microbes and plants. aroA mutants that lack an EPSP synthase do not grow on minimal media that lacks aromatic amino acids (Pittard and Wallace (1966) *J. Bacteriol.* 91:1494-508), but can grow in rich media, such as LB. However, genes encoding EPSPS activity can restore ability to grow on glyphosate upon aroA mutant *E. coli* strains. Thus, a test for genetic complementation of an aroA mutant is a highly sensitive method to test if a gene is capable of functioning as an EPSPS in *E. coli*. Such tests for gene function by genetic complementation are known in the art.

A deletion of the aroA gene was created in *E. coli* XL-1 MRF' (Stratagene) by PCR/recombination methods known in the art and outlined by Datsenko and Wanner, (2000) *Proc. Natl. Acad. Sci. USA* 97:6640-6645. This system is based on the Red system that allows for chromosomal disruptions of targeted sequences. A large portion (1067 nt of the 1283 nt) of the aroA coding region was disrupted by the engineered deletion. The presence of the deletion was confirmed by PCR with several sets of oligonucleotides, and by the appearance of an aroA phenotype in the strain, referred to herein as 'ΔaroA'. ΔaroA grows on LB media (which contains all amino acids) and grows on M63 media supplemented with phenylalanine, tryptophan, and tyrosine, but does not grow on M63 minimal media (which lacks aromatic amino acids). These results indicate that ΔaroA exhibits an aroA phenotype.

The ability of an EPSPS to complement the mutant phenotype of ΔaroA was confirmed. Clone pAX482, an *E. coli* expression vector containing the wild-type *E. coli* aroA gene, was transformed into ΔaroA, and transformed cells were selected. These cells (containing a functional aroA gene residing on a plasmid) were then plated on LB media, M63, and M63 with amino acid supplements. Where the ΔaroA mutant strain grew only on LB and M63 supplemented with aromatic amino acids, ΔaroA cells containing the functional aroA gene on a plasmid grew on all three media types.

In order to determine if GDC-1 or GDC-2 could confer complementation, plasmid pAX472, the expression vector containing GDC-1, and pAX473, the expression vector containing GDC-2 were transformed into ΔaroA and plated on the same three types of media. Cells transformed with either pAX472 or pAX473 were able to grow on M63 media supplemented with phenylalanine, tryptophan, and tyrosine and LB media but they were not able to grow on M63 alone. Thus, neither GDC-1 nor GDC-2 are capable of complementing the aroA mutation, and thus neither GDC-1 nor GDC-2 is an EPSP synthase.

Example 5

Purification of GDC-1 Expressed as a 6×His-Tagged Protein in *E. coli*

The GDC-1 coding region (1,728 nucleotides, SEQ ID NO:21) was amplified by PCR using ProofStart™ DNA polymerase. Oligonucleotides used to prime PCR were designed to introduce restriction enzyme recognition sites near the 5' and 3' ends of the resulting PCR product. The resulting PCR product was digested with BamH I and Sal I. BamH I cleaved the PCR product at the 5' end, and Sal I cleaved the PCR product at the 3' end. The digested product was cloned into the 6×His-tag expression vector pQE-30 (Qiagen), prepared by digestion with BamH I and Sal I. The resulting clone, pAX623, contained GDC-1 in the same translational reading frame as, and immediately C-terminal to, the 6×His tag of pQE-30. General strategies for generating such clones, and for expressing proteins containing 6×His-tag are well known in the art.

The ability of this clone to confer glyphosate resistance was confirmed by plating cells of pAX623 onto M63 media containing 5 mM glyphosate. pAX623 containing cells gave rise to colonies, where cells containing the vector alone gave no colonies.

GDC-1 protein from pAX623-containing cells was isolated by expression of GDC-1-6×His-tagged protein in *E. coli*, and the resulting protein purified using Ni-NTA Superflow Resin (Qiagen) as per manufacturer's instructions.

Example 6

Assay of GDC-1 Pyruvate Decarboxylase Activity 100 ng of GDC-1 protein was tested for activity in a standard pyruvate decarboxylase assay (Gounaris et al. (1971) *J. of Biol. Chem.* 246:1302-1309). This assay is a coupled reaction where in the first step the pyruvate decarboxylase (PDC) converts pyruvate to acetaldehyde and $CO_2$. The acetaldehyde produced in this reaction is a substrate for alcohol dehydrogenase, which converts acetaldehyde and β-NADH to ethanol and β-NAD. Thus, PDC activity is detected by virtue of utilization of β-NADH as decrease in absorbance at 340 nM in a spectrophotometer. GDC-1 as well as a control enzyme (pyruvate decarboxylase, Sigma) were tested in this assay. GDC-1 showed activity as a pyruvate decarboxylase, and the reaction rate correlated with the concentration of pyruvate in the assay.

Example 7

Assay of GDC-1 Ability to Modify Glyphosate

The ability of GDC-1 to modify glyphosate in vitro was tested by incubating GDC-1 with a mixture of radiolabeled and non-labeled glyphosate, and analyzing the reaction products by HPLC.

100 ng of GDC-1 purified protein was incubated with 20,000 cpm of $C^{14}$ labeled glyphosate ($NaOOCCH_2NH^{14}CH_2PO_3H_2$; Sigma catalog #G7014), mixed with unlabelled glyphosate to a final concentration of 2 mM in a reaction buffer of 200 mM Na-Citrate, pH 6.0, 1 mM TPP, 2 mM $MgCl_2$. Reaction was allowed to proceed 60 minutes, then 5 μl was applied to HPLC column (Dionex AminoPac PA10 analytical (and guard) column, anion exchange resin; Dionex Corporation). The column was equilibrated with 150 mM sodium hydroxide. Fractions were eluted with a sodium acetate gradient of 150-300 mM sodium acetate. Single drop (40 uL) fractions were collected, and the radioactivity present in each fraction determined using a 96-well scintillation counter. Analysis of the resulting data shows that GDC-1 converts a portion of the labeled glyphosate to a product with an elution time of approximately 19 minutes (FIG. 2B). Control experiments lacking purified GDC-1 show no peak at this elution time.

Example 8

Purification of GDC-2 Expressed as a 6×His-tagged Protein in E. coli

The GDC-2 coding region (2,088 nucleotides, SEQ ID NO:14) was amplified by PCR using ProofStart™ DNA polymerase (Qiagen). Oligonucleotides used to prime PCR were designed to introduce restriction enzyme recognition sites near the 5' and 3' ends of the resulting PCR product. The resulting PCR product was digested with BamH I and Hind III. BamH I cleaved the PCR product at the 5' end, and Sal I cleaved the PCR product at the 3' end. The digested product was cloned into the 6×His-tag expression vector pQE-30 (Qiagen), prepared by digestion with BamH I and Hind III. The resulting clone, pAX624, contained GDC-2 in the same translational reading frame as, and immediately C-terminal to, the 6×His tag of pQE-30. General strategies for generating such clones, and for expressing proteins containing 6×His-tag are well known in the art.

The ability of this clone to confer glyphosate resistance was confirmed by plating cells of pAX624 onto M63 media containing 5 mM glyphosate. pAX624 containing cells gave rise to colonies, where cells containing the vector alone gave no colonies.

GDC-2 protein (SEQ ID NO: 15) from pAX624-containing cells was isolated by expression of GDC-2-6×His-tagged protein in E. coli, and the resulting protein purified using Ni-NTA Superflow Resin (Qiagen) as per manufacturer's instructions.

Example 9

Assay of GDC-2 Acetolactate Synthase Activity

Acetolactate synthases are decarboxylating enzymes that condense two pyruvate molecules to form acetolactate with the release of a $CO_2$ moiety from one of the pyruvate substrates. In the detection of the enzymatic reaction described by Pang and Duggleby (Pang and Duggleby (1999) Biochemistry 18:5222-5231), the product acetolactate is converted to acetoin by incubation with 1% $H_2SO_4$ for 15 minutes at 60° C. followed by neutralization with KOH. The acetoin is then detected as described by Westerfeld (Westerfeld (1945) J. Biol. Chem. 161:495-502), using 0.15% creatine and 1.5% alpha-naphthol (dissolved in 2.5 N NaOH). The red colored reaction product is quantified by absorbance at 525 nm.

Samples containing either 5 μg or 10 μg of GDC-2 were incubated in 50 mM pyruvate, 1 mM thymine pyrophosphate, 10 mM $MgCl_2$, 0.01 mM Flavin adenine dinucleotide (FAD), 100 mM potassium phosphate buffer pH 7.0 (total reaction volume of 50 μl) for 2 hours at 37° C. The reaction was stopped by the addition of 1 μl of 50% sulfuric acid ($H_2SO_4$) and incubated at 60° C. for 15 minutes. The reaction was neutralized by the addition of 30 μl of 1 N KOH followed by the addition of 10 μl of 1.5% creatine and 10 μl of 15% alpha-napthol dissolved in 2.5 N NaOH. The red colored reaction product was quantified by absorbance at 525 nm.

TABLE 3

| Acetolactate synthase activity | |
| --- | --- |
| Amount GDC-2 (μg) | Absorbance 525 nm |
| 0 μg (control) | 0.0 |
| 5 μg | 1.99 |
| 10 μg | 3.13 |

Example 10

Engineering GDC-1 for Plant Transformation

The GDC-1 open reading frame (ORF, SEQ ID NO:21) was amplified by PCR from a full-length cDNA template. Hind III restriction sites were added to each end of the ORF during PCR. Additionally, the nucleotide sequence ACC was added immediately 5' to the start codon of the gene to increase translational efficiency (Kozak (1987) Nucleic Acids Research 15:8125-8148; and Joshi (1987) Nucleic Acids Research 15:6643-6653). The PCR product was cloned and sequenced, using techniques well known in the art, to ensure that no mutations were introduced during PCR.

The plasmid containing the GDC-1 PCR product was partially digested with Hind III and the 1.7 kb Hind III fragment containing the intact ORF was isolated. (GDC-1 contains an internal Hind III site in addition to the sites added by PCR.) This fragment was cloned into the Hind III site of plasmid pAX200, a plant expression vector containing the rice actin promoter (McElroy et al. (1991) Molecular General Genetics 231:150-160) and the PinII terminator (An et al. (1989) The Plant Cell 1:115-122). The promoter—gene—terminator fragment from this intermediate plasmid was subcloned into Xho I site of plasmid pSB11 (Japan Tobacco, Inc.) to form the plasmid pAX810. pAX810 is organized such that the 3.45 kb DNA fragment containing the promoter—GDC-1—terminator construct may be excised from pAX810 by double digestion with KpnI and XbaI for transformation into plants using aerosol beam injection. The structure of pAX810 was verified by restriction digests and gel electrophoresis and by sequencing across the various cloning junctions.

Plasmid pAX810 was mobilized into Agrobacterium tumifaciens strain LBA4404 which also harbored the plasmid pSB 1 (Japan Tobacco, Inc.), using triparental mating procedures well known in the art, and plating on media containing spectinomycin. Plasmid pAX810 carries spectinomycin resistance but is a narrow host range plasmid and cannot replicate in *Agrobacterium*. Spectinomycin resistant colonies arise when pAX810 integrates into the broad host range plasmid pSB1 through homologous recombination. The cointegrate product of pSB1 and pAX810 recombination (pAX204) was verified by Southern hybridization (data not shown). The *Agrobacterium* strain harboring pAX204 was used to transform maize by the PureIntro method (Japan Tobacco).

Example 11

Engineering GDC-2 for Plant Transformation

The GDC-2 open reading frame (ORF) was amplified by polymerase chain reactions from a full-length cDNA template. Hind III restriction sites were added to each end of the ORF during PCR. Additionally, the nucleotide sequence ACC was added immediately 5' to the start codon of the gene to increase translational efficiency (Kozak (1987) 15:8125-8148; Joshi (1987) *Nucleic Acids Research* 15:6643-6653). The PCR product was cloned and sequenced, using techniques well known in the art, to ensure that no mutations were introduced during PCR.

The plasmid containing the GDC-2 PCR product was digested with Hind III and the fragment containing the intact ORF was isolated. This fragment was cloned into the Hind III site of plasmid pAX200, a plant expression vector containing the Rice Actin promoter (McElroy et al. (1991) *Molecular General Genetics* 231:150-160) and the PinII terminator (An et al. (1989) *The Plant Cell* 1:115-122). PAX811 is organized such that the 3.91 kb DNA fragment containing the promoter—GDC-2—terminator construct may be excised from pAX811 by double digestion with Kpn I and Pme I and used for transformation into plants by aerosol beam injection. The structure of pAX811 was verified by restriction digests and gel electrophoresis and by sequencing across the various cloning junctions.

Plasmid pAX810 was mobilized into *Agrobacterium tumifaciens* strain LBA4404 which also harbored the plasmid pSB1 (Japan Tobacco, Inc.), using triparental mating procedures well known in the art, and plating on media containing spectinomycin. Plasmid pAX811 carries spectinomycin resistance but is a narrow host range plasmid and cannot replicate in *Agrobacterium*. Spectinomycin resistant colonies arise when pAX811 integrates into the broad host range plasmid pSB1 through homologous recombination. The cointegrate product of pSB1 and pAX811 recombination (pAX205) was verified by Southern hybridization (data not shown). The *Agrobacterium* strain harboring pAX205 was used to transform maize by the PureIntro method (Japan Tobacco).

Example 12

Transformation of GDC-1 and GDC-2 into Plant Cells

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D). However, media and salts other than DN62A55 are suitable and are known in the art. Embryos are incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express GDC-1, GDC-2 or GDC-1 and GDC-2 in plant cells are accelerated into plant tissue using an aerosol beam accelerator, using conditions essentially as described in PCT Publication No. WO/0138514. After beaming, embryos are incubated for 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 13

Transformation of GDC-1 and GDC-2 into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for conferring resistance to glyphosate in a cell, comprising transforming said cell with a DNA construct, said construct comprising a promoter that drives expression in said cell, operably linked to a nucleotide sequence encoding an amino acid sequence having at least 95% sequence identity with the amino acid sequence of SEQ ID NO:3, 22, or 24.

2. The method of claim 1, wherein expression of said amino acid sequence having at least 95% sequence identity with the amino acid sequence of SEQ ID NO:3, 22, or 24 results in increased tolerance of the cell to glyphosate.

3. The method of claim 1, wherein said cell is a plant cell.

4. A transformed plant cell, said cell comprising a DNA construct, said construct comprising a promoter that drives expression in a plant cell operably linked with a nucleotide sequence that encodes an amino acid sequence having at least 95% sequence identity with the amino acid sequence of SEQ ID NO:3, 22, or 24.

5. A plant regenerated from the plant cell of claim 4, wherein said plant is resistant to glyphosate.

6. A transformed seed comprising the plant cell of claim 4.

7. A plant having stably incorporated into its genome a DNA construct comprising a promoter that drives expression in a plant cell operably linked with a nucleotide sequence that encodes an amino acid sequence having at least 95% sequence identity with the amino acid sequence of SEQ ID NO:3, 22, or 24.

8. The plant of claim 7, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

* * * * *